United States Patent
Emtage et al.

(10) Patent No.: US 12,280,119 B2
(45) Date of Patent: Apr. 22, 2025

(54) CHIMERIC TRANSMEMBRANE PROTEINS AND USES THEREOF

(71) Applicant: KITE PHARMA, INC., Santa Monica, CA (US)

(72) Inventors: Peter Emtage, Lafayette, CA (US); Rosa Vincent, New York City, NY (US)

(73) Assignee: KITE PHARMA, INC., Foster City, CA (US)

( * ) Notice: Subject to any disclaimer, the term of this patent is extended or adjusted under 35 U.S.C. 154(b) by 1054 days.

(21) Appl. No.: 17/040,009

(22) PCT Filed: Mar. 21, 2019

(86) PCT No.: PCT/US2019/023424
§ 371 (c)(1),
(2) Date: Sep. 21, 2020

(87) PCT Pub. No.: WO2019/183389
PCT Pub. Date: Sep. 26, 2019

(65) Prior Publication Data
US 2021/0015864 A1 Jan. 21, 2021

Related U.S. Application Data

(60) Provisional application No. 62/647,498, filed on Mar. 23, 2018.

(51) Int. Cl.
*A61K 38/19* (2006.01)
*A61K 39/00* (2006.01)
*A61K 47/62* (2017.01)
*A61K 47/65* (2017.01)
*C07K 14/55* (2006.01)
*C07K 14/705* (2006.01)
*C07K 14/715* (2006.01)
*C07K 14/725* (2006.01)

(52) U.S. Cl.
CPC .......... *A61K 47/65* (2017.08); *A61K 39/4611* (2023.05); *A61K 39/4631* (2023.05); *A61K 39/464412* (2023.05); *C07K 14/55* (2013.01); *C07K 14/7051* (2013.01); *C07K 14/70578* (2013.01); *C07K 14/7155* (2013.01)

(58) Field of Classification Search
None
See application file for complete search history.

(56) References Cited

FOREIGN PATENT DOCUMENTS

| WO | 2010020766 A2 | | 2/2010 |
| WO | WO 2011123683 | * | 6/2011 |
| WO | 2011123683 A2 | | 10/2011 |
| WO | 2016022671 A1 | | 2/2016 |
| WO | 2017201432 A2 | | 11/2017 |

OTHER PUBLICATIONS

Ju et al, Structure-Function Analysis of Human Interleukin-2, the Journal of Biological Chemistry, 1987, pp. 5723-5731.*
Wang et al, Structural Biology of Shared Cytokine Receptors, Annu Rev Immunol. 2009 ; pp. 1-35.*
Teege et al, Tuning IL-2 signaling by ADP-ribosylation of CD25, Scientific Reports, 2015, pp. 1-7.*
Gaffen, S, Signaling Domains of the Interleukin 2 Receptor, Cytokine, vol. 14, No. 2 (Apr. 21), 2001: pp. 63-77.*
Kim, "Tumor Therapy Applying Membrane-bound Form of Cytokines," Immune Network, vol. 9, No. 5, (2009), pp. 158-168.

* cited by examiner

Primary Examiner — Maria Marvich
(74) Attorney, Agent, or Firm — Barnes & Thornburg LLP

(57) ABSTRACT

Provided herein are chimeric transmembrane proteins, nucleic acids encoding these chimeric transmembrane proteins, and mammalian cells containing these nucleic acids, and methods of making and using these mammalian cells.

7 Claims, 3 Drawing Sheets

Specification includes a Sequence Listing.

CHIMERIC TRANSMEMBRANE PROTEINS AND USES THEREOF

CROSS-REFERENCE TO RELATED APPLICATION

This application is the U.S. National Stage of International Patent Application No. PCT/US2019/023424, filed Mar. 21, 2019, which was published in English under PCT Article 21 (2), and which claims priority to U.S. Provisional Patent Application Ser. No. 62/647,498, filed on Mar. 23, 2018; the entire contents of which are herein incorporated by reference.

REFERENCE TO SEQUENCE LISTING

The Sequence Listing submitted Mar. 10, 2025 as a text file named "Revised CDL600_ST25" created on Mar. 10, 2025, and having a size of 84,708 bytes is hereby incorporated by reference pursuant to 37 C.F.R. § 1.52(e)(5).

TECHNICAL FIELD

The present disclosure relates to the field of biotechnology, and more specifically, to single-chain and multi-chain chimeric antigen receptors.

BACKGROUND

Interleukin-2 receptor is expressed on the cell surface (either temporary or permanent) in almost all hematopoietic cells including lymphoid linages T, B, and NK cells, as well as myeloid ones like macrophages, monocytes, and neutrophils. Upon binding to IL-2, the interleukin-2 receptor transduces a signal into the cell via activation of the Janus kinases—JAK1 and JAK3. The phosphorylation of the cytoplasmic domain of the ∂-chain of the interleukin-2 receptor enables homodimer formation of STAT-3 and STAT-5 factors. Homodimers of STAT-3 and STAT-5 migrate to the nucleus and enhance transcription of IL-2-dependent genes (Zlatko Dembic, Chapter 6, Cytokines of the Immune System, Academic Press, 2015, pages 143-239).

While many improvements have been made to generate a secondary proliferative signal in second generation chimeric antigen receptor (CAR) T-cells (through the inclusion of co-stimulatory signaling domains such as CD28 and 4-1 BB in chimeric antigen receptors), this signal remains antigen-dependent often does not have sufficient co-stimulatory activity in solid tumors that have low tumor associated antigen levels.

In another attempt to provide sufficient co-stimulatory activity in CAR T-cells, co-administration of cytokines belonging to the common gamma (γc) chain receptor family have been used. However, prolonged usage of recombinant, pro-proliferative cytokines, such as IL-2, is often associated with severe side effects, limiting the duration and dosage of administration. In view of the above, alternative, improved methods of providing a co-stimulatory signal to CAR T-cells are desired.

SUMMARY

The present disclosure is based, at least in part, on the discovery that a chimeric transmembrane protein including an extracellular IL-2 domain, an extracellular sushi domain of an alpha chain of an interleukin-2 receptor, and a transmembrane domain of an alpha chain of an interleukin-2 receptor provide for antigen-independent co-stimulation of a chimeric antigen receptor (CAR) T-cell. In view of this discovery, provided herein are chimeric antigen receptors that include an extracellular IL-2 domain, an extracellular sushi domain from an alpha chain of interleukin-2 receptor, and a transmembrane domain of an alpha chain of interleukin-2 receptor. Also provided are nucleic acids encoding these chimeric transmembrane proteins, vectors including any of these nucleic acids, and mammalian cells that include any of these nucleic acids or vectors. Also provided herein are methods of treating a cancer, methods of inducing cell death in a cancer cell (e.g., apoptosis and/or necrosis), and methods of decreasing the risk of developing a metastasis or an additional metastasis in a subject in need thereof that include administering any of the mammalian cells described herein to the subject.

Provided herein are chimeric transmembrane proteins that include: an extracellular IL-2 domain; an extracellular sushi domain from an alpha chain of interleukin-2 receptor; and a transmembrane domain of an alpha chain of interleukin-2 receptor. In some embodiments of any of the chimeric transmembrane proteins described herein, the extracellular IL-2 domain includes a sequence of a wildtype IL-2 protein. In some embodiments of any of the chimeric transmembrane proteins described herein, the wildtype IL-2 protein is a wildtype human IL-2 protein. In some embodiments of any of the chimeric transmembrane proteins described herein, the wildtype human IL-2 protein includes a sequence of SEQ ID NO: 1. In some embodiments of any of the chimeric transmembrane proteins described herein, the extracellular IL-2 domain includes a sequence that is at least 80% identical to the sequence of a wildtype IL-2 protein. In some embodiments of any of the chimeric transmembrane proteins described herein, the extracellular IL-2 domain includes a sequence that is at least 95% identical to the sequence of a wildtype IL-2 protein. In some embodiments of any of the chimeric transmembrane proteins described herein, the wildtype IL-2 protein is a wildtype human IL-2 protein. In some embodiments of any of the chimeric transmembrane proteins described herein, the wildtype human IL-2 protein is SEQ ID NO: 1. In some embodiments of any of the chimeric transmembrane proteins described herein, the extracellular IL-2 domain is a sequence of a wildtype IL-2 protein having one or both of (i) one to ten amino acids removed from the N-terminus of the sequence of the wildtype IL-2 protein, and (ii) one to ten amino acids removed from the C-terminus of the sequence of the wildtype IL-2 protein. In some embodiments of any of the chimeric transmembrane proteins described herein, the wildtype IL-2 protein is a human wildtype IL-2 protein. In some embodiments of any of the chimeric transmembrane proteins described herein, the human wildtype IL-2 protein is SEQ ID NO: 1.

In some embodiments of any of the chimeric transmembrane proteins described herein, the chimeric transmembrane protein further includes a linker sequence positioned between the extracellular IL-2 domain and the extracellular sushi domain. In some embodiments of any of the chimeric transmembrane proteins described herein, the linker sequence is 2 amino acids to about 50 amino acids (e.g., 4 amino acids to about 40 amino acids). In some embodiments of any of the chimeric transmembrane proteins described herein, the linker sequence is a naturally-occurring amino acid sequence. In some embodiments of any of the chimeric transmembrane proteins described herein, the linker sequence is not a naturally-occurring amino acid sequence. In some embodiments of any of the chimeric transmembrane proteins described herein, the linker sequence includes a sequence of SEQ ID NO: 2. In some embodiments of any of the chimeric transmembrane proteins described herein, the linker sequence consists of a sequence of SEQ ID NO: 2.

Some embodiments of any of the chimeric transmembrane proteins described herein further include an additional linker sequence positioned between the extracellular sushi domain and the transmembrane domain. In some embodiments of any of the chimeric transmembrane proteins described herein, the additional linker sequence is 2 amino acids to about 50 amino acids (e.g., 4 amino acids to about 40 amino acids). In some embodiments of any of the chimeric transmembrane proteins described herein, the additional linker sequence is a naturally-occurring amino acid sequence. In some embodiments of any of the chimeric transmembrane proteins described herein, the additional linker sequence is not a naturally-occurring amino acid sequence. In some embodiments of any of the chimeric transmembrane proteins described herein, the linker sequence includes a sequence of SEQ ID NO: 2. In some embodiments of any of the chimeric transmembrane proteins described herein, the linker sequence consists of a sequence of SEQ ID NO: 2.

In some embodiments of any of the chimeric transmembrane proteins described herein, the extracellular sushi domain includes a sushi domain from a wildtype alpha chain of interleukin-2 receptor. In some embodiments of any of the chimeric transmembrane proteins described herein, the wildtype alpha chain of interleukin-2 receptor is wildtype human alpha chain of interleukin-2 receptor. In some embodiments of any of the chimeric transmembrane proteins described herein, the extracellular sushi domain of the wildtype human alpha chain of interleukin-2 receptor includes one or both of the sequence of SEQ ID NO: 3 and SEQ ID NO: 4. In some embodiments of any of the chimeric transmembrane proteins described herein, the extracellular sushi domain is at least 80% identical to a sequence of an extracellular sushi domain of a wildtype alpha chain of interleukin-2 receptor. In some embodiments of any of the chimeric transmembrane proteins described herein, the extracellular sushi domain is at least 95% identical to the sequence of the extracellular sushi domain of a wildtype alpha chain of interleukin-2 receptor. In some embodiments of any of the chimeric transmembrane proteins described herein, the wildtype alpha chain of interleukin-2 receptor is a wildtype human alpha chain of interleukin-2 receptor. In some embodiments of any of the chimeric transmembrane proteins described herein, the extracellular sushi domain of the wildtype human alpha chain of interleukin-2 receptor includes one or both of the sequences of SEQ ID NO: 3 and SEQ ID NO: 4. In some embodiments of any of the chimeric transmembrane proteins described herein, the extracellular sushi domain is a sequence of an extracellular sushi domain of a wildtype alpha chain of interleukin-2 receptor having one or both of (i) one to five amino acids removed from the N-terminus of the sequence of the extracellular sushi domain of the wildtype alpha chain of interleukin-2 receptor, and (ii) one to five amino acids removed from the C-terminus of the sequence of the extracellular sushi domain of the wildtype alpha chain of interleukin-2 receptor. In some embodiments of any of the chimeric transmembrane proteins described herein, the wildtype alpha chain of interleukin-2 receptor is a wildtype human alpha chain of interleukin-2 receptor. In some embodiments of any of the chimeric transmembrane proteins described herein, the sequence of the extracellular sushi domain of the wildtype human alpha chain of interleukin-2 receptor includes one or both of the sequence of SEQ ID NO: 3 or SEQ ID NO: 4.

In some embodiments of any of the chimeric transmembrane proteins described herein, the transmembrane domain includes a transmembrane domain from a wildtype alpha chain of interleukin-2 receptor. In some embodiments of any of the chimeric transmembrane proteins described herein, the wildtype alpha chain of interleukin-2 receptor is wildtype human alpha chain of interleukin-2 receptor. In some embodiments of any of the chimeric transmembrane proteins described herein, the transmembrane domain of the wildtype human alpha chain of interleukin-2 receptor includes a sequence of SEQ ID NO: 5. In some embodiments of any of the chimeric transmembrane proteins described herein, the transmembrane domain is at least 80% identical to a sequence of a transmembrane domain of a wildtype alpha chain of interleukin-2 receptor. In some embodiments of any of the chimeric transmembrane proteins described herein, the transmembrane domain is at least 95% identical to the sequence of the transmembrane domain of a wildtype alpha chain of interleukin-2 receptor. In some embodiments of any of the chimeric transmembrane proteins described herein, the wildtype alpha chain of interleukin-2 receptor is a wildtype human alpha chain of interleukin-2 receptor. In some embodiments of any of the chimeric transmembrane proteins described herein, the transmembrane domain of the wildtype human alpha chain of interleukin-2 receptor is SEQ ID NO: 5. In some embodiments of any of the chimeric transmembrane proteins described herein, the transmembrane domain is a sequence of a transmembrane domain of a wildtype alpha chain of interleukin-2 receptor having one or both of (i) one to ten amino acids removed from the N-terminus of the sequence of the transmembrane domain of the wildtype alpha chain of interleukin-2 receptor, and (ii) one to ten amino acids removed from the C-terminus of the sequence of the transmembrane domain of the wildtype alpha chain of interleukin-2 receptor. In some embodiments of any of the chimeric transmembrane proteins described herein, the wildtype alpha chain of interleukin-2 receptor is a wildtype human alpha chain of interleukin-2 receptor. In some embodiments of any of the chimeric transmembrane proteins described herein, the sequence of the transmembrane domain of the wildtype human alpha chain of interleukin-2 receptor is SEQ ID NO: 5.

In some embodiments of any of the chimeric transmembrane proteins described herein, the chimeric transmembrane protein further includes an intracellular domain of an alpha chain of interleukin-2 receptor. In some embodiments of any of the chimeric transmembrane proteins described herein, the intracellular domain includes a sequence of an intracellular domain of a wildtype alpha chain of interleukin-2 receptor. In some embodiments of any of the chimeric transmembrane proteins described herein, the wildtype alpha chain of interleukin-2 receptor is a wildtype human alpha chain of interleukin-2 receptor. In some embodiments of any of the chimeric transmembrane proteins described herein, the intracellular domain of the wildtype alpha chain of interleukin-2 receptor includes a sequence of SEQ ID NO: 6. In some embodiments of any of the chimeric transmembrane proteins described herein, the intracellular domain includes a sequence that is at least 80% identical to a sequence of an intracellular domain of a wildtype alpha chain of interleukin-2 receptor. In some embodiments of any of the chimeric transmembrane proteins described herein, the intracellular domain includes a sequence that is at least 95% identical to the sequence of the intracellular domain of the wildtype alpha chain of interleukin-2 receptor. In some embodiments of any of the chimeric transmembrane proteins described herein, the wildtype alpha chain of interleukin-2 receptor is a wildtype human alpha chain of interleukin-2 receptor. In some embodiments of any of the chimeric transmembrane proteins described herein, the sequence of the intracellular domain of the wildtype human alpha chain of interleukin-2 receptor is SEQ ID NO: 6. In some embodiments of any of the chimeric transmembrane proteins described herein, the intracellular domain is a sequence of an intracellular domain of a wildtype alpha chain of interleukin-2 receptor having one or both of (i) one to ten amino acids removed from the N-terminus of the sequence of the intracellular domain of the wildtype alpha chain of interleukin-2 receptor, and (ii) one to ten amino acids removed from the C-terminus of the sequence of the intracellular domain of the wildtype alpha chain of interleukin-2 receptor. In some embodiments of any of the chimeric transmembrane proteins described herein, the wildtype alpha chain of interleukin-2 receptor is a wildtype human alpha chain of interleukin-2 receptor. In some embodiments of any of the chimeric transmembrane proteins described herein, the sequence of the intracellular domain of the wildtype human alpha chain of interleukin-2 receptor is SEQ ID NO: 6.

Also provided are nucleic acids encoding any of the chimeric transmembrane proteins described herein. Also provided are vectors that include any of the nucleic acids encoding any of the chimeric transmembrane proteins described herein. Some embodiments of any of the vectors described herein, further include a promoter sequence operably linked to the nucleic acid encoding any of the chimeric transmembrane proteins described herein, and optionally, an enhancer sequence operably linked to the nucleic acid encoding any of the chimeric transmembrane proteins described herein. Some embodiments of any of the vectors described herein further include a poly(A) sequence operably linked to the nucleic acid encoding any of the chimeric transmembrane proteins described herein. Some embodiments of any of the vectors described herein further include a sequence encoding a chimeric antigen receptor. In some embodiments of any of the vectors described herein, the chimeric antigen receptor binds specifically to a tumor antigen. In some embodiments of any of the vectors described herein, the tumor antigen is selected from the group of: glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin. In some embodiments of any of the vectors described herein, the tumor antigen is glypican-3. In includes one or more co-stimulatory signaling domains selected from the group consisting of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12. In some embodiments of any of the vectors described herein, the vector is a lentiviral or adenoviral vector.

Also provided herein are mammalian cells that include any of the nucleic acids encoding any of the chimeric transmembrane proteins described herein or any of the vectors described herein. In some embodiments of any of the mammalian cells described herein, the mammalian cell is an immune cell. In some embodiments of any of the mammalian cells described herein, the immune cell is selected from the group of: a CD4+ T cell, a CD8+ T cell, a B cell, a monocyte, a natural killer cell, a dendritic cell, a macrophage, a regulatory T cell, and a helper T cell. In some embodiments of any of the mammalian cells described herein, the mammalian cell was previously obtained from a subject or is a daughter cell of a mammalian cell that was previously obtained from the subject. In some embodiments of any of the mammalian cells described herein, the mammalian cell is a human cell.

Also provided herein are pharmaceutical compositions that include any of the vectors described herein and a pharmaceutically acceptable carrier. Also provided herein are pharmaceutical compositions that include any of the mammalian cells described herein.

Also provided herein are sets of vectors that include: a first vector that is any of the vectors described herein that include any of the nucleic acids encoding any of the chimeric transmembrane proteins described herein; and a second vector that includes a sequence encoding a chimeric antigen receptor. In some embodiments of any of the sets of vectors described herein, the chimeric antigen receptor binds specifically to a tumor antigen. In some embodiments of any of the sets of vectors described herein, the tumor antigen is selected from the group of: glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin. In some embodiments of any of the sets of vectors described herein, the tumor antigen is glypican-3. In some embodiments of any of the sets of vectors described herein, the chimeric antigen receptor includes one or more co-stimulatory signaling domains selected from the group consisting of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12. In some embodiments of any of the sets of vectors described herein, one or both of the first vector and the second vector is a lentiviral or adenoviral vector. In some embodiments of any of the sets of vectors described herein, the second vector further includes a promoter operably linked to the sequence encoding the chimeric antigen receptor, and optionally, an enhancer operably linked to the sequence encoding the chimeric antigen receptor. In some embodiments of any of the sets of vectors described herein, the second vector further includes a poly(A) sequence operably linked to the sequence encoding the chimeric antigen receptor.

Also provided herein are mammalian cells that include any of the sets of vectors described herein. In some embodiments of any of the mammalian cells described herein, the mammalian cell is an immune cell. In some embodiments of any of the mammalian cells described herein, the immune cell is selected from the group of: a CD4+ T cell, a CD8+ T cell, a B cell, a monocyte, a natural killer cell, a dendritic cell, a macrophage, a regulatory T cell, and a helper T cell. In some embodiments of any of the mammalian cells described herein, the mammalian cell was previously obtained from a subject or is a daughter cell of a mammalian cell that was previously obtained from the subject. In some embodiments of any of the mammalian cells described herein, the mammalian cell is a human cell.

Also provided herein are pharmaceutical compositions that include any of the sets of vectors described herein and a pharmaceutically acceptable carrier. Also provided herein are pharmaceutical compositions that include a mammalian cell including any of the sets of vectors described herein. Also provided herein are kits that include any of the pharmaceutical compositions described herein.

Also provided herein are methods of treating a cancer in a subject in need thereof that include administering a therapeutically effective amount of any of the mammalian cells described herein to the subject. In some embodiments of any of the methods described herein, the subject is a human, and the mammalian cell is human. In some embodiments of any of the methods described herein, the mammalian cell was previously obtained from the subject or is a daughter cell of a cell previously obtained from the subject.

Also provided herein are methods of reducing the volume of a solid tumor in a subject in need thereof that include administering a therapeutically effective amount of any of the mammalian cells described herein to the subject. In some embodiments of any of the methods described herein, the subject is a human, and the mammalian cell is human. In some embodiments of any of the methods described herein, the mammalian cell was previously obtained from the subject or is a daughter cell of a cell previously obtained from the subject.

Also provided herein are methods of inducing cell death in a cancer cell in a subject in need thereof that include administering a therapeutically effective amount of any of the mammalian cells described herein to the subject. In some embodiments of any of the methods described herein, the subject is a human, and the mammalian cell is human. In some embodiments of any of the methods described herein, the mammalian cell was previously obtained from the subject or is a daughter cell of a cell previously obtained from the subject.

Also provided herein are methods of decreasing the risk of developing a metastasis or an additional metastasis in a subject having a cancer that include administering a therapeutically effective amount of any of the mammalian cells described herein to the subject. In some embodiments of any of the methods described herein, the subject is a human, and the mammalian cell is human. In some embodiments of any of the methods described herein, the mammalian cell was previously obtained from the subject or is a daughter cell of a cell previously obtained from the subject.

The use of the term "a" before a noun is meant "one or more" of the particular noun. For example, the phrase "a mammalian cell" means "one or more mammalian cell."

The terms "chimeric antigen receptor" and "CAR" are used interchangeably herein, and refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. CAR molecules and derivatives thereof (e.g., CAR variants) are described, e.g., in PCT Application No. US2014/016527; Fedorov et al. *Sci Transl Med* (2013); 5(215):215ra172; Glienke et al. *Front Pharmacol* (2015) 6:21; Kakarla & Gottschalk 52 *Cancer J* (2014) 20(2):151-5; Riddell et al. *Cancer J* (2014) 20(2): 141-4; Pegram et al. *Cancer J* (2014) 20(2):127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety. A CAR can be a single-chain chimeric antigen receptor or a multi-chain chimeric antigen receptor.

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein, including, without limitation, scFvs, or LBDs of growth factors. Additional examples of antigen-binding domains are known in the art.

As used herein, the term "antigen" refers generally to a binding partner specifically recognized by an antigen-binding domain described herein. Exemplary antigens include different classes of molecules, such as, but not limited to, polypeptides and peptide fragments thereof, small molecules, lipids, carbohydrates, and nucleic acids. Non-limiting examples of antigen or antigens that can be specifically bound by any of the antigen-binding domains are described herein. Additional examples of antigen or antigens that can be specifically bound by any of the antigen-binding domains are known in the art.

The term "intracellular signaling domain" means an intracellular signaling domain from an endogenous signaling transmembrane polypeptide expressed in an immune cell (e.g., a T lymphocyte) that promotes downstream immune cell signaling (e.g., T-cell receptor signaling) and/or immune cell activation (e.g., T cell activation). Non-limiting examples of intracellular signaling domains are described herein. Additional examples of intracellular signaling domains are known in the art. See, e.g., Chen et al., *Nature Reviews Immunol.* 13:227-242, 2013.

The term "immunoreceptor tyrosine-based activation motif" or "ITAM)" means an amino acid motif that includes a four amino-acid consensus sequence of a tyrosine separated from a leucine or an isoleucine by two other amino acids (YxxL/I). The tyrosine residue in the four-amino acid consensus sequence becomes phosphorylated following interaction of a signaling pathway kinase (e.g., a lymphocyte signaling pathway kinase). Non-limiting examples of ITAMs are described herein. Additional examples of ITAMs are known in the art.

The phrase "treatment of cancer" means a reduction in the number, frequency, or severity of one or more (e.g., two, three, four, or five) symptoms of a cancer in a subject having a cancer.

As used herein, "extracellular domain" describes a portion of a polypeptide (e.g., a domain) that is present in the extracellular space when the polypeptide is expressed in a mammalian cell (e.g., a human cell).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
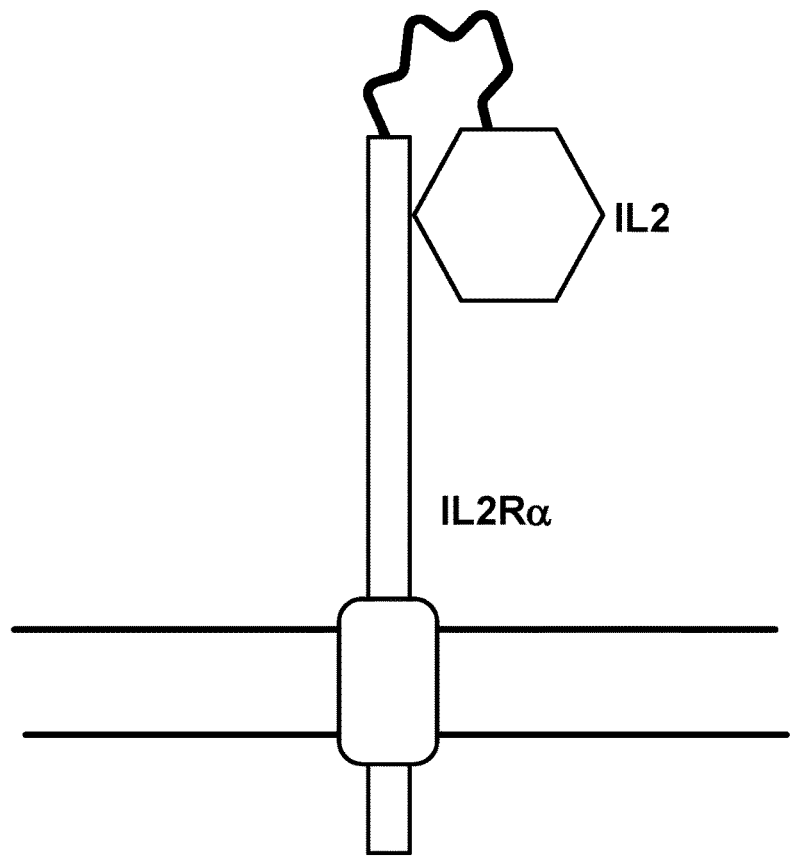
FIG. 1 is a schematic drawing of an exemplary chimeric transmembrane protein comprising an extracellular interleukin-2 (IL-2) domain, an extracellular sushi domain from the alpha chain of interleukin-2 receptor (IL-2Rα), a transmembrane domain of an alpha chain of interleukin-2 receptor, and a linker sequence positioned between the extracellular IL-2 domain and the extracellular sushi domain.

Provided herein are chimeric antigen receptors that include an extracellular IL-2 domain, an extracellular sushi domain from an alpha chain of interleukin-2 receptor, and a transmembrane domain of an alpha chain of interleukin-2 receptor. Also provided are nucleic acids encoding these chimeric transmembrane proteins, vectors including any of these nucleic acids, and mammalian cells that include any of these nucleic acids or vectors. Also provided herein are methods of treating a cancer, methods of inducing cell death in a cancer cell (e.g., apoptosis and/or necrosis), and methods of decreasing the risk of developing a metastasis or an additional metastasis in a subject in need thereof that include administering any of the mammalian cells described herein to the subject.

The chimeric transmembrane proteins provided herein can be used to maintain CAR T-cells in the absence of exogenous cytokine support or antigen stimulation, thus providing for the T-cell stimulatory effects of IL-2 without the dose-limiting toxicities associated with prolonged administration of soluble, recombinant IL-2.

Non-limiting aspects of the chimeric transmembrane proteins, nucleic acids, vectors, mammalian cells, and methods provided herein are described below, and can be used in any combination without limitation. Additional aspects of these chimeric transmembrane proteins, nucleic acids, vectors, mammalian cells, and methods are known in the art.

Chimeric Transmembrane Proteins

Provided herein are chimeric transmembrane proteins that include an extracellular IL-2 domain (e.g., any of the exemplary extracellular IL-2 domains described herein or known in the art), an extracellular sushi domain from an alpha chain of interleukin-2 receptor (e.g., one or more of any of the exemplary extracellular sushi domains from an alpha chain of interleukin-2 receptor described herein or known in the art), and a transmembrane domain of an alpha chain of interleukin-2 receptor (e.g., any of the exemplary transmembrane domains of an alpha chain of interleukin-2 receptor described herein or known in the art). In some embodiments, the chimeric transmembrane protein comprises a linker sequence positioned between the extracecullar IL-2 domain and the extracecullar sushi domain (e.g., any of the exemplary linker sequences described herein or known in the art). In some embodiments, the chimeric transmembrane protein further comprises an additional linker positioned between the extracecullar sushi domain and the transmembrane domain of the alpha chain of the interleukin-2 receptor (e.g., any of the exemplary linker sequences described herein or known in the art). In some embodiments, the chimeric transmembrane protein can further include an intracellular domain of an alpha chain of interleukin-2 receptor (e.g., any of the exemplary intracellular domains of an alpha chain of interleukin-2 receptor described herein or known in the art).

In some embodiments, the chimeric transmembrane protein comprises or is SEQ ID NO: 7 (shown below).

```
Exemplary Chimeric Transmembrane Protein
                                        (SEQ ID NO: 7)
MLLLVTSLLLCELPHPAFLLIPHHHHHHAPTSSSTKKTQLQLEHLLLDLQ

MILNGINNYKNPKLTRMLTFKFYMPKKATELKHLQCLEEELKPLEEVLNL

AQSKNFHLRPRDLISNINVIVLELKGSETTFMCEYADETATIVEFLNRWI

TFCQSllSTLTSGGGSGGGGSGGGGSGGGGSGGGGSLQELCDDDPPEIPHA

TFKAMAYKEGTMLNCECKRGFRRIKSGSLYMLCTGNSSHSSWDNQCQCTS

SATRNTTKQVTPQPEEQKERKTTEMQSPMQPVDQASLPGHCREPPPWENE

ATERIYHFVVGQMVYYQCVQGYRALHRGPAESVCKMTHGKTRWTQPQLIC

TGEMETSQFPGEEKPQASPEGRPESETSCLVTTTDFQIQTEMAATMETSI

FTTEYQVAVAGCVFLLISVLLLSGLTWQRRQRKSRRTI
```

In some embodiments, the chimeric transmembrane protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 7.

In some embodiments, the chimeric transmembrane protein comprises or is SEQ ID NO: 8 (shown below).

```
Exemplary Chimeric Transmembrane Protein
                                        (SEQ ID NO: 8)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSllSTLTSGGGSGGGGSGGGGSGG

GGSGGGSLQELCDDDPPEIPHATFKAMAYKEGTMLNCECKRGFRRIKSGS

LYMLCTGNSSHSSWDNQCQCTSSATRNTTKQVTPQPEEQKERKTTEMQSP

MQPVDQASLPGHCREPPPWENEATERIYHFVVGQMVYYQCVQGYRALHRG

PAESVCKMTHGKTRWTQPQLICTGEMETSQFPGEEKPQASPEGRPESETS

CLVTTTDFQIQTEMAATMETSIFTTEYQVAVAGCVFLLISVLLLSGLTWQ

RRQRKSRRTI
```

In some embodiments, the chimeric transmembrane protein comprises or is a sequence that is at least 60% identical, at least 65% identical, at least 70% identical, at least 75% identical, at least 80% identical, at least 82% identical, at least 84% identical, at least 86% identical, at least 88% identical, at least 90% identical, at least 91% identical, at least 92% identical, at least 94% identical, at least 95% identical, at least 96% identical, at least 97% identical, at least 98% identical, at least 99% identical, or 100% identical to SEQ ID NO: 8.

In some embodiments, the chimeric transmembrane protein (e.g., mature or precursor protein) can be about 210 amino acids to about 650 amino acids, about 210 amino acids to about 640 amino acids, about 210 amino acids to about 620 amino acids, about 210 amino acids to about 600 amino acids, about 210 amino acids to about 580 amino acids, about 210 amino acids to about 560 amino acids, about 210 amino acids to about 540 amino acids, about 210 amino acids to about 520 amino acids, about 210 amino acids to about 500 amino acids, about 210 amino acids to about 480 amino acids, about 210 amino acids to about 460 amino acids, about 210 amino acids to about 440 amino acids, about 210 amino acids to about 420 amino acids, about 210 amino acids to about 400 amino acids, about 210 amino acids to about 380 amino acids, about 210 amino acids to about 360 amino acids, about 210 amino acids to about 340 amino acids, about 210 amino acids to about 320 amino acids, about 210 amino acids to about 300 amino acids, about 210 amino acids to about 280 amino acids, about 210 amino acids to about 260 amino acids, about 210 amino acids to about 240 amino acids, about 220 amino acids to about 650 amino acids, about 220 amino acids to about 640 amino acids, about 220 amino acids to about 620 amino acids, about 220 amino acids to about 600 amino acids, about 220 amino acids to about 580 amino acids, about 220 amino acids to about 560 amino acids, about 220 amino acids to about 540 amino acids, about 220 amino acids to about 520 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 650 amino acids, about 240 amino acids to about 640 amino acids, about 240 amino acids to about 620 amino acids, about 240 amino acids to about 600 amino acids, about 240 amino acids to about 580 amino acids, about 240 amino acids to about 560 amino acids, about 240 amino acids to about 540 amino acids, about 240 amino acids to about 520 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 650 amino acids, about 260 amino acids to about 640 amino acids, about 260 amino acids to about 620 amino acids, about 260 amino acids to about 600 amino acids, about 260 amino acids to about 580 amino acids, about 260 amino acids to about 560 amino acids, about 260 amino acids to about 540 amino acids, about 260 amino acids to about 520 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 650 amino acids, about 280 amino acids to about 640 amino acids, about 280 amino acids to about 620 amino acids, about 280 amino acids to about 600 amino acids, about 280 amino acids to about 580 amino acids, about 280 amino acids to about 560 amino acids, about 280 amino acids to about 540 amino acids, about 280 amino acids to about 520 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 650 amino acids, about 300 amino acids to about 640 amino acids, about 300 amino acids to about 620 amino acids, about 300 amino acids to about 600 amino acids, about 300 amino acids to about 580 amino acids, about 300 amino acids to about 560 amino acids, about 300 amino acids to about 540 amino acids, about 300 amino acids to about 520 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 650 amino acids, about 320 amino acids to about 640 amino acids, about 320 amino acids to about 620 amino acids, about 320 amino acids to about 600 amino acids, about 320 amino acids to about 580 amino acids, about 320 amino acids to about 560 amino acids, about 320 amino acids to about 540 amino acids, about 320 amino acids to about 520 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 650 amino acids, about 340 amino acids to about 640 amino acids, about 340 amino acids to about 620 amino acids, about 340 amino acids to about 600 amino acids, about 340 amino acids to about 580 amino acids, about 340 amino acids to about 560 amino acids, about 340 amino acids to about 540 amino acids, about 340 amino acids to about 520 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 650 amino acids, about 360 amino acids to about 640 amino acids, about 360 amino acids to about 620 amino acids, about 360 amino acids to about 600 amino acids, about 360 amino acids to about 580 amino acids, about 360 amino acids to about 560 amino acids, about 360 amino acids to about 540 amino acids, about 360 amino acids to about 520 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 650 amino acids, about 380 amino acids to about 640 amino acids, about 380 amino acids to about 620 amino acids, about 380 amino acids to about 600 amino acids, about 380 amino acids to about 580 amino acids, about 380 amino acids to about 560 amino acids, about 380 amino acids to about 540 amino acids, about 380 amino acids to about 520 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 650 amino acids, about 400 amino acids to about 640 amino acids, about 400 amino acids to about 620 amino acids, about 400 amino acids to about 600 amino acids, about 400 amino acids to about 580 amino acids, about 400 amino acids to about 560 amino acids, about 400 amino acids to about 540 amino acids, about 400 amino acids to about 520 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 650 amino acids, about 420 amino acids to about 640 amino acids, about 420 amino acids to about 620 amino acids, about 420 amino acids to about 600 amino acids, about 420 amino acids to about 580 amino acids, about 420 amino acids to about 560 amino acids, about 420 amino acids to about 540 amino acids, about 420 amino acids to about 520 amino acids, about 420 amino acids to about 500 amino acids, about 420 amino acids to about 480 amino acids, about 420 amino acids to about 460 amino acids, about 420 amino acids to about 440 amino acids, about 440 amino acids to about 650 amino acids, about 440 amino acids to about 640 amino acids, about 440 amino acids to about 620 amino acids, about 440 amino acids to about 600 amino acids, about 440 amino acids to about 580 amino acids, about 440 amino acids to about 560 amino acids, about 440 amino acids to about 540 amino acids, about 440 amino acids to about 520 amino acids, about 440 amino acids to about 500 amino acids, about 440 amino acids to about 480 amino acids, about 440 amino acids to about 460 amino acids, about 460 amino acids to about 650 amino acids, about 460 amino acids to about 640 amino acids, about 460 amino acids to about 620 amino acids, about 460 amino acids to about 600 amino acids, about 460 amino acids to about 580 amino acids, about 460 amino acids to about 560 amino acids, about 460 amino acids to about 540 amino acids, about 460 amino acids to about 520 amino acids, about 460 amino acids to about 500 amino acids, about 460 amino acids to about 480 amino acids, about 480 amino acids to about 650 amino acids, about 480 amino acids to about 640 amino acids, about 480 amino acids to about 620 amino acids, about 480 amino acids to about 600 amino acids, about 480 amino acids to about 580 amino acids, about 480 amino acids to about 560 amino acids, about 480 amino acids to about 540 amino acids, about 480 amino acids to about 520 amino acids, about 480 amino acids to about 500 amino acids, about 500 amino acids to about 650 amino acids, about 500 amino acids to about 640 amino acids, about 500 amino acids to about 620 amino acids, about 500 amino acids to about 600 amino acids, about 500 amino acids to about 580 amino acids, about 500 amino acids to about 560 amino acids, about 500 amino acids to about 540 amino acids, about 500 amino acids to about 520 amino acids, about 520 amino acids to about 650 amino acids, about 520 amino acids to about 640 amino acids, about 520 amino acids to about 620 amino acids, about 520 amino acids to about 600 amino acids, about 520 amino acids to about 580 amino acids, about 520 amino acids to about 560 amino acids, about 520 amino acids to about 540 amino acids, about 540 amino acids to about 650 amino acids, about 540 amino acids to about 640 amino acids, about 540 amino acids to about 620 amino acids, about 540 amino acids to about 600 amino acids, about 540 amino acids to about 580 amino acids, about 540 amino acids to about 560 amino acids, about 560 amino acids to about 650 amino acids, about 560 amino acids to about 640 amino acids, about 560 amino acids to about 620 amino acids, about 560 amino acids to about 600 amino acids, about 560 amino acids to about 580 amino acids, about 580 amino acids to about 650 amino acids, about 580 amino acids to about 640 amino acids, about 580 amino acids to about 620 amino acids, about 580 amino acids to about 600 amino acids, about 600 amino acids to about 650 amino acids, about 600 amino acids to about 640 amino acids, about 600 amino acids to about 620 amino acids, about 620 amino acids to about 650 amino acids, about 620 amino acids to about 640 amino acids, or about 630 amino acids to about 650 amino acids, in length.

In some embodiments, the chimeric transmembrane protein further comprises a signal sequence at its N-terminus. In some embodiments, the signal sequence comprises or is the sequence of MLLLVTSLLLCELPHPAFLLIP (SEQ ID NO: 9). Additional examples of signal sequences are known in the art. For example, a signal sequence can be about 5 amino acids to about 30 amino acids, about 5 amino acids to about 28 amino acids, about 5 amino acids to about 26 amino acids, about 5 amino acids to about 24 amino acids, about 5 amino acids to about 22 amino acids, about 5 amino acids to about 20 amino acids, about 5 amino acids to about 18 amino acids, about 5 amino acids to about 16 amino acids, about 5 amino acids to about 14 amino acids, about 5 amino acids to about 12 amino acids, about 5 amino acids to about 10 amino acids, about 5 amino acids to about 8 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 30 amino acids, about 22 amino acids to about 28 amino acids, about 22 amino acids to about 26 amino acids, about 22 amino acids to about 24 amino acids, about 24 amino acids to about 30 amino acids, about 24 amino acids to about 28 amino acids, about 24 amino acids to about 26 amino acids, about 26 amino acids to about 30 amino acids, about 26 amino acids to about 28 amino acids, or about 28 amino acids to about 30 amino acids, in length.

In some embodiments, the chimeric transmembrane protein can further include a peptide tag. For example, a tag can be used to help facilitate purification, production, and/or identification of the chimeric transmembrane protein. In some embodiments, the tag is a histidine tag comprising at least six histidine residues. Additional examples of tags are known in the art.

Non-limiting aspects of any of the chimeric transmembrane proteins provided herein are described below.

Extracellular IL-2 Domains

In some embodiments of any of the chimeric transmembrane proteins described herein, the extracellular IL-2 domain comprises or is a sequence of a wildtype IL-2 protein (e.g., a mature wildtype IL-2 protein). For example, the wildtype IL-2 protein can be a wildtype human IL-2 protein (e.g., a mature wildtype human IL-2 protein), a wildtype mouse IL-2 protein (e.g., a mature wildtype mouse IL-2 protein), a wildtype chimpanzee IL-2 protein (e.g., a mature wildtype chimpanzee IL-2 protein), or a wildtype monkey IL-2 protein (e.g., a mature wildtype monkey IL-2 protein). Non-limiting examples of wildtype IL-2 protein sequences and nucleic acids encoding these exemplary IL-2 protein sequences are provided below.

Mature Wildtype Human IL-2

(SEQ ID NO: 1)

APTSSSTKKTQLQLEHLLLDLQMILNGINNYKNPKLTRMLTFKFYMPKKATELKHLQCL

EEELKPLEEVLNLAQSKNFHLRPRDLISNINVIVLELKGSETTFMCEYADETATIVEFLNR

WITFCQSIISTLTS cDNA encoding Mature Wildtype Human IL-2 Protein (mature protein encoded by nucleotides 116 to 514 of SEQ ID NO: 10)

(SEQ ID NO: 10)

```
  1 agttccctat cactctcttt aatcactact cacagtaacc tcaactcctg ccacaatgta
 61 caggatgcaa ctcctgtctt gcattgcact aagtcttgca cttgtcacaa acagtgcacc
121 tacttcaagt tctacaaaga aaacacagct acaactggag catttactgc tggatttaca
181 gatgattttg aatggaatta ataattacaa gaatcccaaa ctcaccagga tgctcacatt
241 taagttttac atgcccaaga aggccacaga actgaaacat cttcagtgtc tagaagaaga
301 actcaaacct ctggaggaag tgctaaattt agctcaaagc aaaaactttc acttaagacc
361 cagggactta atcagcaata tcaacgtaat agttctggaa ctaaagggat ctgaaacaac
421 attcatgtgt gaatatgctg atgagacagc aaccattgta gaatttctga acagatggat
481 tacctttgt caaagcatca tctcaacact gacttgataa ttaagtgctt cccacttaaa
541 acatatcagg ccttctattt atttaaatat ttaaatttta tatttattgt tgaatgtatg
601 gtttgctacc tattgtaact attattctta atcttaaaac tataaatatg gatcttttat
661 gattcttttt gtaagcccta ggggctctaa aatggtttca cttatttatc ccaaatatt
721 tattattatg ttgaatgtta aatatagtat ctatgtgat tggttagtaa aactatttaa
781 taaatttgat aaatataaaa aaaaaaaaaa aaaaaaaaa aa
```

Mature Wildtype Monkey IL-2 Protein (SEQ ID NO: 11)

aptssstkkt qlqlehlllld lqmilnginn yknpkltrml tfkfympkka telkhlqcle eelkpleevl nlaqsknfhl rdtkdlisni nvivlelkgs ettlmceyad etativefln rwitfcgsli stlt cDNA encoding Mature Wildtype Monkey IL-2 Protein (mature protein encoded by nucleotides 61 to 462 of SEQ ID NO: 12)

(SEQ ID NO: 12)

```
  1 atgtacagga tgcaactcct gtcttgcatt gcactaagtc ttgcacttgt cacaaacagt
 61 gcacctactt caagttctac aaagaaaaca cagctacaac tggagcattt actgctggat
121 ttacagatga ttttgaatgg aattaataat acaagaatc ccaaactcac caggatgctc
181 acatttaagt tttacatgcc caagaaggcc acagaattga acatcttca gtgtctagaa
241 gaagaactca aacctctgga ggaagtgcta aatttagctc aaagcaaaaa ctttcactta
301 agagatacca aggacttaat cagcaatatc aacgtaatag ttctggaact aaagggatct
361 gaaacaacac tgatgtgtga atatgctgat gagacagcaa ccattgtaga atttctgaac
421 agatggatta cctttttgtca aagcatcatc tcaacactga cctgataatt aagtgcttcc
481 cacttaaaac atatcag
```

Mature Wildtype Chicken IL-2 Protein (SEQ ID NO: 13)

aslssekw ktlqtlikdl elleniknki hlelytptet qectqqtlqc ylgevvtlkk eteddtelke efvtaignie knlksltgln htgseckice annkkkfpdf lheltnfvry lqk cDNA encoding Mature Wildtype Chicken IL-2 Protein (mature protein encoded by nucleotides 127 to 489 of SEQ ID NO: 14)

(SEQ ID NO: 14)

```
  1 atcacctcac attgtacatc acaatttgaa taccagcata cagataactg ggacactgcc
 61 atgatgtgca agtactgat ctttggctgt atttcggtag caatgctaat gactacagct
121 tatggagcat ctctatcatc agaaaaatgg aaaactcttc aaacattaat aaaggattta
```

-continued

```
181 gaaatattgg aaaatatcaa gaataagatt catctcgagc tctacacacc aactgagacc 241 caggagtgca cccagcaaac tctgcagtgt tacctgggag aagtggttac tctgaagaaa 301 gaaactgaag atgacactga aattaaagaa gaatttgtaa ctgctattca aaatatcgaa 361 aagaacctca agagtcttac gggtctaaat cacaccggaa gtgaatgcaa gatctgtgaa 421 gctaacaaca agaaaaaatt tcctgatttt ctccatgaac tgaccaactt tgtgagatat 481 ctgcaaaaat aagcaactaa tcattttat tttactgcta tgttatttat ttaattattt 541 aattacagat aatttatata ttttatcccg tggctaacta atctgctgtc cattctggga 601 ccactgtatg ctcttagtct gggtgatatg acgtctgttc taagatcata tttgatcctt 661 tctgtaagcc ctacgggctc aaaatgtacg ttggaaaact gattgattct cactttgtcg 721 gtaaagtgat atgtgtttac tgaaagaatt tttaaaagtc acttctagat gacatttaat 781 aaatttcagt aatatatg
```

Mature Wildtype Mouse IL-2 Protein
(SEQ ID NO: 15)

```
aptssstsss taeaqqqqqq qqqqqqhleq llmdlgells rmenyrnlkl prmltfkfyl pkqatelkdl qcledelgpl rhvldltqsk sfqledaenf isnirvtvvk lkgsdntfec qfddesatvy dflrrwiafc qslistspq
``` cDNA encoding Mature Wildtype Mouse IL-2 Protein (mature protein
encoded by nucleotides 109 to 555 of SEQ ID NO: 16)
(SEQ ID NO: 16)

```
  1 tatcaccctt gctaatcact cctcacagtg acctcaagtc ctgcaggcat gtacagcatg 61 cagctcgcat cctgtgtcac attgacactt gtgctccttg tcaacagcgc acccacttca 121 agctccactt caagctctac agcggaagca cagcagcagc agcagcagca gcagcagcag 181 cagcagcacc tggagcagct gttgatggac ctacaggagc tcctgagcag gatggagaat 241 tacaggaacc tgaaactccc caggatgctc accttcaaat tttacttgcc caagcaggcc 301 acagaattga aagatcttca gtgcctagaa gatgaacttg gacctctgcg gcatgttctg 361 gatttgactc aaagcaaaag ctttcaattg gaagatgctg agaatttcat cagcaatatc 421 agagtaactg ttgtaaaact aaagggctct gacaacacat tgagtgccaa attcgatgat 481 gagtcagcaa ctgtggtgga ctttctgagg agatggatag ccttctgtca aagcatcatc 541 tcaacaagcc ctcaataact atgtacctcc tgcttacaac acataaggct ctctatttat 601 ttaaatattt aactttaatt tatttttgga tgtattgttt actatctttt gtaactacta 661 gtcttcagat gataaatatg gatctttaaa gattcttttt gtaagcccca agggctcaaa 721 aatgttttaa actatttatc tgaaattatt tattatattg aattgttaaa tatcatgtgt 781 aggtagactc attaataaaa gtatttagat gattcaaata taaataagct cagatgtctg 841 tcattttag gacagcacaa agtaagcgct aaaataactt ctcagttatt cctgtgaact 901 ctatgttaat cagtgttttc aagaaataaa gctctcctct aaaaaaaaaa aaaaa
```

In some embodiments, the extracellular IL-2 domain comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a wildtype IL-2 protein sequence (e.g., any of the exemplary wildtype IL-2 protein sequences described herein or known in the art, e.g., SEQ ID NO: 1, 11, 13, or 15). In some embodiments, the wildtype IL-2 protein is a wildtype human IL-2 protein (e.g., a mature wildtype human IL-2 protein, e.g., SEQ ID NO: 1).

As one skilled in the art can appreciate, when amino acids that are not conserved between wildtype IL-2 proteins from different species are mutated (e.g., substituted with a different amino acid) they are less likely to cause a decrease in the level of one or more activities of a IL-2 protein. In contrast, when amino acids that are conserved between wildtype IL-2 proteins from different species are mutated (e.g., substituted with a different amino acid) they are more likely to cause a decrease in the level of one or more activities of a IL-2 protein. In view of this knowledge, one skilled in the art can select which amino acid positions in a to wildtype IL-2 protein (e.g., the non-conserved amino acids) can be substituted without decreasing the activity of the IL-2 protein.

In some embodiments, the extracellular IL-2 domain is a sequence of a wildtype IL-2 protein (e.g., a mature wildtype IL-2 protein, e.g., any of the mature wildtype IL-2 proteins described herein, e.g., mature wildtype human IL-2 protein, e.g., SEQ ID NO: 1) having one to ten (e.g., one, two, three, four, five, six, seven, eight, nine, or ten) amino acids removed from the N-terminus of the sequence of the wildtype IL-2 protein. In some embodiments, the extracellular IL-2 domain is a sequence of a wildtype IL-2 protein (e.g., a mature wildtype IL-2 protein, e.g., any of the mature wildtype IL-2 proteins described herein, e.g., mature wildtype human IL-2 protein, e.g., SEQ ID NO: 1) having one to ten (e.g., one, two, three, four, five, six, seven, eight, nine, or ten) amino acids removed from the C-terminus of the sequence of the wildtype IL-2 protein. In some embodiments, the extracellular IL-2 domain is a sequence of a wildtype IL-2 protein (e.g., a mature wildtype IL-2 protein, e.g., any of the mature wildtype IL-2 proteins described herein, e.g., mature wildtype human IL-2 protein, e.g., SEQ ID NO: 1) having both one to ten amino (e.g., one, two, three, four, five, six, seven, eight, nine, or ten) acids removed from the N-terminus of the sequence of the wildtype IL-2 protein and one to ten (e.g., one, two, three, four, five, six, seven, eight, nine, or ten) amino acids removed from the C-terminus of the sequence of the wildtype IL-2 protein.

Alpha Chain of an IL-2 Receptor

The IL-2 receptor is a heterotrimeric protein generated by different combinations of three different proteins—the alpha chain (IL-2Rα, also known as CD25), the beta chain (IL-2Rβ, also known as CD122), and the gamma chain (IL-2Rγc, also known as CD132).

The alpha chain (IL-2Rα) of human IL-2 receptor is encoded on chromosome 10p14-15 by the gene IL2RA. Non-limiting examples of mature wildtype alpha chains of IL-2 receptor are shown below. In some embodiments of any of the chimeric transmembrane proteins provided herein, the portion of the chimeric transmembrane protein that comprises the extracellular sushi domain and the transmembrane domain comprises or is a sequence of a mature wildtype alpha chain of IL-2 receptor (e.g., any of the exemplary mature wildtype alpha chain of IL-2 receptor protein sequences shown below, e.g., SEQ ID NO: 17).

```
Mature Wildtype Human Alpha Chain of IL-2 Receptor
                                                        (SEQ ID NO: 17)
elcdddppe iphatfkama ykegtmlnce ckrgfrriks gslymlctgn sshsswdnqc qctssatrnt tkqvtpqpee qkerkttemq spmqpvdqas lpghcreppp weneaterly hfvvgqmvyy qcvqgyralh rgpaesvckm thgktrwtqp qlictgemet sqfpgeekpq aspegrpese tsclvtttdf qiqtemaatm etsiftteyq vavagcvfll isvillsglt wqrrqrksrr ti cDNA Encoding Mature Wildtype Human Alpha Chain of IL-2 Receptor
(mature protein encoded by nucleotides 283 to 1035 of SEQ ID NO: 18)
                                                        (SEQ ID NO: 18)
    1 ggcagtttcc tggctgaaca cgccagccca atacttaaag agagcaactc ctgactccga 601 tagagactgg atggacccac aagggtgaca gcccaggcgg accgatcttc ccatcccaca 121 tcctccggcg cgatgccaaa aagaggctga cggcaactgg gccttctgca gagaaagacc 181 tccgcttcac tgccccggct ggtcccaagg gtcaggaaga tggattcata cctgctgatg 241 tggggactgc tcacgttcat catggtgcct ggctgccagg cagagctctg tgacgatgac 301 ccgccagaga tcccacacgc cacattcaaa gccatggcct acaaggaagg aaccatgttg 361 aactgtgaat gcaagagagg tttccgcaga ataaaaagcg ggtcactcta tatgctctgt 421 acaggaaact ctagccactc gtcctgggac aaccaatgtc aatgcacaag ctctgccact 481 cggaacacaa cgaaacaagt gacacctcaa cctgaagaac agaaagaaag gaaaaccaca 541 gaaatgcaaa gtccaatgca gccagtggac aagcgagcc ttccaggtca ctgcagggaa 601 cctccaccat gggaaaatga agccacagag agaatttatc atttcgtggt ggggcagatg 661 gtttattatc agtgcgtcca gggatacagg gctctacaca gaggtcctgc tgagagcgtc 721 tgcaaaatga cccacgggaa gacaaggtgg acccagcccc agctcatatg cacaggtgaa 781 atggagacca gtcagtttcc aggtgaagag aagcctcagg caagcccccga aggccgtcct 841 gagagtgaga cttcctgcct cgtcacaaca acagattttc aaatacagac agaaatggct 901 gcaaccatgg agacgtccat atttacaaca gagtaccagg tagcagtggc cggctgtgtt 961 ttcctgctga tcagcgtcct cctcctgagt gggctcacct ggcagcggag acagaggaag 1021 agtagaagaa caatctagaa aaccaaaaga acaagaattt cttggtaaga agccgggaac 1081 agacaacaga agtcatgaag cccaagtgaa atcaaaggtg ctaaatggtc gcccaggaga 1141 catccgttgt gcttgcctgc gttttggaag ctctgaagtc acatcacagg acacggggca
```

-continued

```
1201 gtggcaacct tgtctctatg ccagctcagt cccatcagag agcgagcgct acccacttct
1261 aaatagcaat ttcgccgttg aagaggaagg gcaaaaccac tagaactctc catcttattt
1321 tcatgtatat gtgttcatta aagcatgaat ggtatggaac tctctccacc ctatatgtag
1381 tataaagaaa agtaggttta cattcatctc attccaactt cccagttcag gagtcccaag
1441 gaaagcccca gcactaacgt aaatacacaa cacacacact ctaccctata caactggaca
1501 ttgtctgcgt ggttcctttc tcagccgctt ctgactgctg attctcccgt tcacgttgcc
1561 taataaacat ccttcaagaa ctctgggctg ctacccagaa atcattttac ccttggctca
1621 atcctctaag ctaaccccct tctactgagc cttcagtctt gaatttctaa aaacagagg
1681 ccatggcaga ataatctttg ggtaacttca aaacggggca gccaaaccca tgaggcaatg
1741 tcaggaacag aaggatgaat gaggtcccag gcagagaatc atacttagca aagttttacc
1801 tgtgcgttac taattggcct ctttaagagt tagtttcttt gggattgcta tgaatgatac
1861 cctgaatttg gcctgcacta atttgatgtt tacaggtgga cacacaaggt gcaaatcaat
1921 gcgtacgttt cctgagaagt gtctaaaaac accaaaaagg gatccgtaca ttcaatgttt
1981 atgcaaggaa ggaaagaaag aaggaagtga agagggagaa gggatggagg tcacactggt
2041 agaacgtaac cacggaaaag agcgcatcag gcctggcacg gtggctcagg cctataaccc
2101 cagctcccta ggagaccaag gcgggagcat ctcttgaggc caggagtttg agaccagcct
2161 gggcagcata gcaagacaca tccctacaaa aaattagaaa ttggctggat gtggtggcat
2221 acgcctgtag tcctagccac tcaggaggct gaggcaggag gattgcttga gcccaggagt
2281 tcgaggctgc agtcagtcat gatggcacca ctgcactcca gcctgggcaa cagagcaaga
2341 tcctgtcttt aaggaaaaaa agacaagatg agcataccag cagtccttga acattatcaa
2401 aaagttcagc atattagaat caccgggagg ccttgttaaa agagttcgct gggcccatct
2461 tcagagtctc tgagttgttg gtctggaata gagccaaatg ttttgtgtgt ctaacaattc
2521 ccaggtgctg ttgctgctgc tactattcca ggaacacact ttgagaacca ttgtgttatt
2581 gctctgcacg cccacccact ctcaactccc acgaaaaaaa tcaacttcca gagctaagat
2641 ttcggtggaa gtcctggttc catatctggt gcaagatctc ccctcacgaa tcagttgagt
2701 caacattcta gctcaacaac atcacacgat taacattaac gaaaattatt catttgggaa
2761 actatcagcc agttttcact tctgaagggg caggagagtg ttatgagaaa tcacggcagt
2821 tttcagcagg gtccagattc agattaaata actattttct gtcatttctg tgaccaacca
2881 catacaaaca gactcatctg tgcactctcc ccctcccct tcaggtatat gttttctgag
2941 taaagttgaa aagaatctca gaccagaaaa tatagatata tatttaaatc ttacttgagt
3001 agaactgatt acgactttg ggtgttgagg ggtctataag atcaaaactt ttccatgata
3061 atactaagat gttatcgacc atttatctgt ccttctctca aaagtgtatg gtggaatttt
3121 ccagaagcta tgtgatacgt gatgatgtca tcactctgct gttaacatat aataaattta
3181 ttgctattgt ttataaaaga ataaatgata tttttt
```

Mature Wildtype Chimpanzee Alpha Chain of IL-2 Receptor (SEQ ID NO: 19)

elcddddppe ithatfkama ykegtmlnce ckrgfrriks gslymlctgn sshsswdnqc qctssatrnt tkqvtpqpee qkerkttemq spmqpvdqas lpghcreppp weneateriy hfvvgqtvyy qcvqgyralh rgpaesvckm thgktrwtqp qlictgemet sqfpgeekpq aspegrpese tsclitttdf qiqtemaatm etfiftteyq vavagcvfll isvlllsglt wqrrq -continued cDNA Encoding Mature Wildtype Chimpanzee Alpha Chain of IL-2 Receptor
(mature protein encoded by nucleotides 64 to 798 of SEQ ID NO: 20)
(SEQ ID NO: 20)

```
  1 atggattcat acctgctgat gtggggactg ctcacgctca tcatggtgcc tggctgcttt 61 gcagagctct gtgacgatga cccgccagag atcacacacg ccacattcaa agccatggcc 121 tacaaggaag aaccatgtt gaactgtgaa tgcaagagag gtttccgcag aataaaaagc 181 gggtcactct atatgctctg tacaggaaac tctagccact cgtcctggga caaccaatgt 241 caatgcacaa gctctgccac tcggaacaca acgaaacaag tgacacctca acctgaagaa 301 cagaaagaaa ggaaaaccac agaaatgcaa agtccaatgc agccagtgga ccaagcgagc 361 cttccaggtc actgcaggga acctccaccg tgggaaaatg aagccacaga gagaatttat 421 catttcgtgg tggggcagac ggtttactac cagtgcgtcc agggatacag ggctctacac 481 agaggtcctg ctgagagcgt ctgcaaaatg acccatggga gacaaggtg acccagccc 541 cagctcatat gcacaggtga atggagacc agtcagtttc caggtgaaga aagcctcag 601 gcaagccccg aaggccgtcc tgagagtgag acttcctgcc tcatcacaac aacagatttt 661 caaatacaga cagaaatggc tgcaaccatg agacgttca tatttacaac agagtaccag 721 gtagcagtgg ccggctgtgt tttcctgctg atcagcgtcc tcctcctgag tgggctcacc 781 tggcagcgga gacagtaa
```

Mature Wildtype Monkey Alpha Chain of IL-2 Receptor
(SEQ ID NO: 21)

elcdddppk ithatfkava ykegtmlnce ckrgfrriks gspymlctgn sshsswdnqc qctssaarnt tkqvtpqpee qkerkttemq sqmqladqvs lpghcreppp weneateriy hfvvgqmvyy qcvqgyralh rgpaesickm thgktrwtqp qlictgetep sqfpgeeepq aspdglpese tsrlvttdf riqtevaatm etfifftteyq vavagcvfll isvllsglt wqrrqrknrr ti cDNA Encoding Mature Wildtype Monkey Alpha Chain of IL-2 Receptor
(mature protein encoded by nucleotides 64 to 816 of SEQ ID NO: 22)
(SEQ ID NO: 22)

```
  1 atggatccat acctgctcat gtggggactg ctcacgttca tcacggtgcc tggctgccag 61 gcagagctct gtgacgatga cccgccaaaa atcacacatg ccacattcaa agccgtggcc 121 tacaaggaag aaccatgtt gaactgtgaa tgcaagagag gtttccgcag aataaaaagc 181 gggtcaccct atatgctctg tacaggaaac tctagccact cgtcctggga caaccaatgt 241 caatgcacaa gctctgctgc tcggaacaca acaaaacaag tgacacctca acctgaagaa 301 cagaaagaaa gaaaaccac agaaatgcaa agtcaaatgc agctggcgga ccaagtgagc 361 cttccaggtc actgcaggga acctccaccg tgggaaaatg aagccacaga aagaatttat 421 catttcgtgg tggggcagat ggtttactac cagtgcgtcc agggatacag ggctctacac 481 agaggtcctg ctgagagcat ctgcaaaatg acccacggga gacaagatg acccagccc 541 cagctcatat gcacaggtga acggagccc agtcagtttc caggtgaaga ggagcctcag 601 gcaagccccg acggccttcc tgagagtgag acttcccgcc tcgtcacaac aacagatttt 661 cgaatacaga cagaagtggc tgcaaccatg gaaacgttca tatttacaac agagtaccaa 721 gtagcagtgg ccggctgtgt tttcctgctg atcagcgtcc tcctgctgag tgggctcacc 781 tggcagcgga gacagaggaa gaatagaaga acaatctaga aaaccaaaag aacaagaact 841 tcttggtaag aagccgagaa cagacaacag aagtcatgaa gcccaagcga aatcaaaggt 901 gctaaatgct tgcccaggag acatccgttg tgct
```

-continued

Mature Wildtype Mouse Alpha Chain of IL-2 Receptor
(SEQ ID NO: 23)

elclydppe vpnatfkals ykngtilnce ckrgfrrlke lvymrclgns wssncqctsn shdksrkqvt aqlehqkeqq tttdmqkptq smhqenltgh crepppwkhe dskriyhfve gqsvhyecip gykalqrgpa isickmkcgk tgwtqpqltc vderehhrfl aseesqgsrn sspesetscp itttdfpqpt ettamtetfv ltmeykvava sclfllisil llsgltwqhr wrksrrti cDNA Encoding Mature Wildtype Mouse Alpha Chain of IL-2 Receptor
(mature protein encoded by nucleotides 273 to 1013 of SEQ ID NO: 24)
(SEQ ID NO: 24)

```
   1 aagttcctgc tgagcagatc agcctaatgc ttaaatagaa caactcctgg ctgtcattga
  61 cattgtctaa aagccaagat gacagactga gaggcctgag cccttgttct ggcattctcc
 121 caggaagatg cagtaaaggg gttgacccaa tatactgcag agaatttcat ccagttccct
 181 cctccatcct gatcccatgt gccaggaaga tggagccacg cttgctgatg ttggggtttc
 241 tctcattaac catagtaccc agttgtcggg cagaactgtg tctgtatgac ccacccgagg
 301 tccccaatgc cacattcaaa gccctctcct acaagaacgg caccatccta aactgtgaat
 361 gcaagagagg tttccgaaga ctaaaggaat tggtctatat gcgttgctta ggaaactcct
 421 ggagcagcaa ctgccagtgc accagcaact cccatgacaa atcgagaaag caagttacag
 481 ctcaacttga acaccagaaa gagcaacaaa ccacaacaga catgcagaag ccaacacagt
 541 ctatgcacca agagaaccct acaggtcact gcagggagcc acctccttgg aaacatgaag
 601 attccaagag aatctatcat ttcgtggaag acagagtgt tcactacgag tgtattccgg
 661 gatacaaggc tctacagaga ggtcctgcta ttagcatctg caagatgaag tgtgggaaaa
 721 cggggtggac tcagccccag ctcacatgtg tagatgaaag agaacaccac cgatttctgg
 781 ctagtgagga atctcaagga agcagaaatt cttctcccga gagtgagact tcctgcccca
 841 taaccaccac agacttccca caacccacag aaacaactgc aatgacggag acatttgtgc
 901 tcacaatgga gtataaggta gcagtggcca gctgcctctt cctgctcatc agcatcctcc
 961 tcctgagcgg gctcacctgg caacacagat ggaggaagag cagaagaacc atctagcaag
1021 ctagaaaagt cagagcccag gcaagcggat gggaatcaca aagctcaagc caaatctgag
1081 acgccaagca ttcacctaac ggctgtttcc ttctgatccc tgggtttcta gaacattctg
1141 aagtcacagg acataacagc aactctatca ctaaactgga ctttgccatt gaagaatagg
1201 atctaaccac ttcagcacag cagttctaaa gctttaatgg gagagagggc ccaacagtgc
1261 tctgtgtgtt ttgttttttgt gtatatctgt tgatgggagc tgagatggtg tggtcacttt
1321 tcatgtaaca tatagtatag aaaaagtagc tttaggttga cttcattgtt acaacccagt
1381 ttggaaagcc caagtaaaac tcagcactaa tgtaaataat tcctcctcct cctcctctct
1441 cttttcatcc tccgctccat cttcctcttc ttcctcctcc ttttccacct cctctgtccc
1501 tacccacccc cacccatcca ctttccttct tcctttctgc tctcacaagc tcatcctagc
1561 tacacgtgca tggctggctc cttttcaac ctctgtttgc ctaactggct cttctgattt
1621 catcacttac tgatcagcct ttaaaactct gagctggcaa agatgactct atctatgttc
1681 ttggctcagt cccagaagga aacccccttt tcatgaagct tcagttttga catcctgaag
1741 aacagaaact gtggcagaac aatcttcaga taacatcaaa acaaagtgga gaagccacgg
1801 gaactgtgga gctctggtat tcagaagcct gtgtctaggg tctgcgccag gagcagaagg
1861 ctgaaggaag tcccaggacg tggacttaga tgctttccca gcaggccact ctaagcgctg
1921 gtttctttgg gacagctgtc aattgtacgc tcaatttagc ctgcactaat ctgatgctta
1981 caggtgaaca ctcaaggcac aggtatggac ttggtacata ccgtgaaaac actggaaaga
```

```
2041 aaagaatact ttcaagttta cagaaggaag gaaggaaaaa ggaagcagag gtggtgatta
2101 tacaaaagat tagctgtaga ctggatatcc caggcatcct cggataatgc ccccgcccca
2161 gcaccctgat ccaggtcacc aaagccttgt gagatcagac tgcagagcca gtctgtctct
2221 gagtcagtaa atgtagaatt tggatttctc acaagttcct ggcggtgtct ttttttttt
2281 taatatttt tattaggtat tttcctcatt tacatttcca atgctatccc aaaagtcccc
2341 catacgctcc cccacactcc cctacccacc cactcccact ttttggccct ggtgttcccc
2401 tgtactgggg catataaagt ttgcaagtcc tggtggtgtc tttatgctga tctctagccc
2461 acactttgtg aggcactggg ctatcccagt gtgctctcct cttccacaga taccaaaagc
2521 acctgggttt gatgctcaga cttctgagca cgttcttgtt caatctcttg cgtaagattt
2581 cctctcagat gagttgagtc agattctcat gtttaacagt gttttagggg attcacagaa
2641 gcccaaacta tcagttttca tttctgaaaa ggctggaaaa ttttatgaaa aactttcaaa
2701 ggtcagacag agccattttg agtcttttat gtgaccaagt atgaaccaga tctttcctat
2761 ctatggtctc ccctttccaa aatatatctt ttgtggggac acggcaagga ggaaagttaa
2821 atagaatctc aagctactaa ttttagaaaa gaaaaaata ttaaactctt actaaagagc
2881 tgtgggtagt ggtacacacc tgtaagccca gctctcagga gactgaggca ggaggattgc
2941 agtgagtcag agatcagctt cacctacaag caaaaccctg ccttacccct caacctttcc
3001 ataaaaacag tcttacttgt gtaaaattaa ttttaatac atatttgtgc acgatgtgtg
3061 tgcctggtgc ccagggaagc caaaaaaata tgttcaatgt ccctggaata ggtggttatg
3121 agctgccatg gaggtgatgg gatttaaacc cctgttctct gaaaaagcag ctagttctct
3181 taaccactga gccatctcta cagccccatt aaattgaatt ttattgtcat tactcaatat
3241 gggagatggg gtaatgataa caattttttt tttataatac taagatgttt agctatttta
3301 ctctccttca caagtgtaga gtagaatttt ctagaagcta catgcatgat attatcgctc
3361 tggtgttaac acataatgga tttatcttgt taataaaaga attagtaaat aatattttaa
3421 attttttctt tgttttagtt ttaagatgat taatatctat agatactagt gtacattaag
3481 aaagcctttg ggatcctcaa tcattttgca tggttttagt aattttttaa taacataaag
3541 aaggtctgac agattatgct aaagagctat tgtggtatgg attagaaatg gcccccacag
3601 gctcctgtgt tcaaacatca gctagcagtg ctgctttggg ttttggaacc tttaagaggt
3661 ggggccttgc ttaaggagat aggtcactgg aggtgaacca gacttgcttc cagtctccct
3721 ctctgctgtc ccaggaagcc atcatatgag gagtttcaca acatacttct gctgccacag
3781 agtccctcca gtaaggcacg tactggccac tgtgtagtgt accctctaaa actgagctag
3841 agctcccctc tcctccctac actatctctg ttgatgcttt gtcacggtga tgaagaacat
3901 aagtaaggca aagacaagac atagtttgga gactcacgtg agcatctcag ccagactcag
3961 gcacagctgc gatgtgggaa ttatcaagca tgagatgcaa agcaatggaa aatgaatcgt
4021 tatgacagaa gcctacatct agtcttccct tcttcccatt agtaataata gcccgtgttt
4081 tagaagaaca catcttttg gtgttctagg tagcttatat tgcaaatgtg gcacaatcta
4141 agagaaatct gggatgaggg aacctcagtg aaagattctc cttgatcaga ttgtcccact
4201 gatgattgat atgggaaggc ccaacccact gtgaaaggca ccacccattg gcaggatgac
4261 tggggttata gaagcaaaca ggctgagcat gagccagtga gcaagccagt aagcagtggc
4321 ttctcttggg aagaagcatg gctttcttcc gtggcttctg tttgatctct ctcaatgata
4381 gattgtgacc tagaagtata agctaaaata aaccatttct tacccata
```

In some embodiments of any of the chimeric transmembrane proteins provided herein, the portion of the chimeric transmembrane protein that comprises the extracellular sushi domain and the transmembrane domain comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a wildtype alpha chain of IL-2 receptor protein sequence (e.g., any of the exemplary mature wildtype alpha chain of IL-2 receptor protein sequences described herein or known in the art, e.g., SEQ ID NO: 17, 19, 21, or 23). In some embodiments of any of the chimeric transmembrane proteins described herein, the portion of the chimeric transmembrane protein that comprises the extracellular sushi domain and the transmembrane domain comprises or is a wildtype human alpha chain of IL-2 receptor protein (e.g., a mature wildtype human alpha chain of IL-2 receptor protein, e.g., SEQ ID NO: 17).

As one skilled in the art can appreciate, when amino acids that are not conserved between wildtype alpha chains of IL-2 receptor protein from different species are mutated (e.g., substituted with a different amino acid) they are less likely to cause a decrease in the level of one or more activities of an alpha chain of IL-2 receptor protein. In contrast, when amino acids that are conserved between wildtype alpha chains of IL-2 receptor protein from different species are mutated (e.g., substituted with a different amino acid) they are more likely to cause a decrease in the level of one or more activities of an alpha chain of IL-2 receptor protein. In view of this knowledge, one skilled in the art can select which amino acid positions in a wildtype alpha chain of an IL-2 receptor protein (e.g., the non-conserved amino acids) can be substituted without decreasing the activity of the alpha chain of an IL-2 receptor protein.

In some embodiments, the portion of the chimeric transmembrane protein that comprises the extracellular sushi domain and the transmembrane domain comprises or is a sequence of a wildtype alpha chain of IL-2 receptor protein (e.g., a mature wildtype alpha chain of IL-2 receptor protein, e.g., any of the mature wildtype alpha chains of IL-2 receptor described herein, e.g., mature wildtype human alpha chain of IL-2 receptor protein, e.g., SEQ ID NO: 17) having one to ten (e.g., one, two, three, four, five, six, seven, eight, nine, or ten) amino acids removed from the N-terminus of the sequence of the wildtype alpha chain of IL-2 receptor protein. In some embodiments, the portion of the chimeric transmembrane protein that comprises the extracellular sushi domain and the transmembrane domain comprises or is a sequence of a wildtype alpha chain of IL-2 receptor protein (e.g., a mature wildtype alpha chain of IL-2 receptor protein, e.g., any of the mature wildtype alpha chains of IL-2 receptor described herein, e.g., mature wildtype human alpha chain of IL-2 receptor protein, e.g., SEQ ID NO: 17) having one to ten (e.g., one, two, three, four, five, six, seven, eight, nine, or ten) amino acids removed from the C-terminus of the sequence of the wildtype alpha chain of IL-2 receptor protein. In some embodiments, the portion of the chimeric transmembrane protein that comprises the extracellular sushi domain and the transmembrane domain comprises or is a sequence of a wildtype alpha chain of IL-2 receptor protein (e.g., a mature wildtype alpha chain of IL-2 receptor protein, e.g., any of the mature wildtype alpha chains of IL-2 receptor described herein, e.g., mature wildtype human alpha chain of IL-2 receptor protein, e.g., SEQ ID NO: 17) having both one to ten amino (e.g., one, two, three, four, five, six, seven, eight, nine, or ten) acids removed from the N-terminus of the sequence of the wildtype alpha chain of IL-2 receptor protein and one to ten (e.g., one, two, three, four, five, six, seven, eight, nine, or ten) amino acids removed from the C-terminus of the sequence of the wildtype alpha chain of IL-2 receptor protein.

Extracellular Sushi Domain of an Alpha Chain of IL-2 Receptor

In some embodiments, the chimeric transmembrane receptors described herein can include one or more (e.g., one, two, three, or four) sushi domains from an alpha chain of IL-2 receptor. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, *Pac. Symp Biocomput.* 2000:155-67). The first cysteine can form a disulfide bond with the third cysteine, and the second cysteine can form a disulfide bridge with the fourth cysteine.

Non-limiting examples of sushi domains are described herein. For example, a sushi domain can be a sushi domain from a wildtype alpha chain of IL-2 receptor (e.g., a sushi domain from a wildtype human alpha chain of IL-2 receptor).

For example, a sushi domain can be about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 90 amino acids, about 70 amino acids to about 85 amino acids, about 70 amino acids to about 80 amino acids, about 70 amino acids to about 75 amino acids, about 75 amino acids to about 90 amino acids, about 75 amino acids to about 85 amino acids, about 75 amino acids to about 80 amino acids, about 80 amino acids to about 90 amino acids, about 80 amino acids to about 85 amino acids, or about 85 amino acids to about 90 amino acids, in length.

For example, an extracellular sushi domain comprises or is an extracellular portion of a mature wildtype alpha chain of IL-2 receptor, e.g., a mature wildtype human alpha chain of IL-2 receptor, e.g., SEQ ID NO: 25 (shown below).

```
Extracellular Portion of Mature Wildtype Human
Alpha Chain of IL-2 Receptor
                                  (SEQ ID NO: 25)
elcdddppe iphatfkama ykegtmlnce ckrgfrriks gslymlctgn sshsswdnqc qctssatrnt tkqvtpqpee qkerkttemq spmqpvdqas lpghcreppp weneateriy hfvvgqmvyy qcvqgyralh rgpaesvckm thgktrwtqp qlictgemet sqfpgeekpq aspegrpese tsclvtttdf qiqtemaatm etsiftteyq
```

In some embodiments, an extracellular sushi domain comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to an extracellular portion of a mature wildtype alpha chain of IL-2 receptor, e.g., a mature wildtype human alpha chain of IL-2 receptor, e.g., SEQ ID NO: 25.

In some embodiments, an extracellular sushi domain is an extracellular portion of a mature wildtype alpha chain of IL-2 receptor (e.g., a mature wildtype human alpha chain of IL-2 receptor, e.g., SEQ ID NO: 25) having one to twenty (e.g., 1, 2, 3, 4, 5, 6, 7, 8, 9, 10, 11, 12, 13, 14, 15, 16, 17, 18, 19, or 20) amino acids removed from the N-terminus of the sequence of the extracellular portion of the mature wildtype alpha chain of IL-2 receptor. In some embodiments, an extracellular sushi domain is an extracellular portion of a mature wildtype alpha chain of IL-2 receptor (e.g., a mature wildtype human alpha chain of IL-2 receptor, e.g., SEQ ID NO: 25) having one to twenty (e.g., 1, 2, 3, 4, 5, 6, 7, 8, 9, 10, 11, 12, 13, 14, 15, 16, 17, 18, 19, or 20) amino acids removed from the C-terminus of the sequence of the extracellular portion of the mature wildtype alpha chain of IL-2 receptor. In some embodiments, an extracellular sushi domain is an extracellular portion of a mature wildtype alpha chain of IL-2 receptor (e.g., a mature wildtype human alpha chain of IL-2 receptor, e.g., SEQ ID NO: 25) having one to twenty (e.g., 1, 2, 3, 4, 5, 6, 7, 8, 9, 10, 11, 12, 13, 14, 15, 16, 17, 18, 19, or 20) amino acids removed from the N-terminus of the sequence of the extracellular portion of the mature wildtype alpha chain of IL-2 receptor and one to twenty (e.g., 1, 2, 3, 4, 5, 6, 7, 8, 9, 10, 11, 12, 13, 14, 15, 16, 17, 18, 19, or 20) amino acids removed from the C-terminus of the sequence of the extracellular portion of the mature wildtype alpha chain of IL-2 receptor.

In some embodiments, an extracellular sushi domain comprises or is a sequence of a sushi domain from a wildtype alpha-chain of IL-2 receptor (e.g., any of the sushi domains from wildtype alpha-chains of IL-2 receptor listed below, e.g., a sushi domain from wildtype human alpha-chain of IL-2 receptor, e.g., a sequence comprising one or both of SEQ ID NO: 3 and 4 below).

```
Exemplary Sushi Domain from Wildtype Human Alpha
Chain of IL-2 Receptor
                                   (SEQ ID NO: 3)
elcdddppeiphatfkamaykegtmlnceckrgfrriksgslymlctgnss hsswdnqc qcts Exemplary Sushi Domain from Wildtype Human Alpha
Chain of IL-2 Receptor
                                   (SEQ ID NO: 4)
ghcrepppweneateriyhfvvgqmvyyqcvqgyralhrgpaesvckmthg ktrwtqpqlictg Exemplary Sushi Domain from Wildtype Chimpanzee
Alpha Chain of IL-2 Receptor
                                  (SEQ ID NO: 26)
elcdddppeithatfkamaykegtmlnceckrgfrriksgslymlctgnss hsswdnqc qcts Exemplary Sushi Domain from Wildtype Chimpanzee
Alpha Chain of IL-2 Receptor
                                  (SEQ ID NO: 27)
ghcrepppweneateriyhfvvgqtvyyqcvqgyralhrgpaesvckmthg ktrwtqpqlictg
```

-continued

Exemplary Sushi Domain from Wildtype Monkey Alpha
Chain of IL-2 Receptor
                                        (SEQ ID NO: 28)
elcdddppkithatfkavaykegtmlnceckrgfrriksgspymlctgnss hsswdnqc qcts Exemplary Sushi Domain from Wildtype Monkey Alpha
Chain of IL-2 Receptor
                                        (SEQ ID NO: 29)
ghcrepppweneateriyhfvvgqmvyyqcvqgyralhrgpaesickmthg ktrwtqpqlictg Exemplary Sushi Domain from Wildtype Mouse Alpha
Chain of IL-2 Receptor
                                        (SEQ ID NO: 30)
elclydppevpnatfkalsykngtilnceckrgfrrlkelvymrclgnsws sncqcts Exemplary Sushi Domain from Wildtype Mouse Alpha
Chain of IL-2 Receptor
                                        (SEQ ID NO: 31)
ghcrepppwkhedskriyhfveggsvhyecipgykalqrgpaisickmkcg ktgwtqpqltcvd In some embodiments, the extracellular sushi domain of the chimeric transmembrane protein comprises a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a sushi domain of a wildtype alpha chain of IL-2 receptor (e.g., SEQ ID NO: 3, 4, 26, 27, 28, 29, 30, or 31).

As one skilled in the art can appreciate, when amino acids that are not conserved between sushi domains from wildtype alpha chains of IL-2 receptor protein from different species are mutated (e.g., substituted with a different amino acid) they are less likely to cause a decrease in the level of IL-2 binding activity of the sushi domain from an alpha chain of IL-2 receptor protein. In contrast, when amino acids that are conserved between the sushi domains from wildtype alpha chains of IL-2 receptor protein from different species are mutated (e.g., substituted with a different amino acid) they are more likely to cause a decrease in the level of IL-2 binding activity of the sushi domain from an alpha chain of IL-2 receptor protein. In view of this knowledge, one skilled in the art can select which amino acid positions in a sushi domain of an alpha chain of an IL-2 receptor protein (e.g., the non-conserved amino acids) can be substituted without decreasing the activity of the sushi domain of the alpha chain of an IL-2 receptor protein.

In some embodiments, the extracellular sushi domain of the chimeric transmembrane protein is a sequence of a sushi domain from a wildtype alpha chain of an IL-2 receptor (e.g., any of SEQ ID NO: 3, 4, 26, 27, 28, 29, 30, or 31) having one to five (e.g., one, two, three, four, or five) amino acids removed from the N-terminus of the sushi domain from the wildtype alpha chain of an IL-2 receptor. In some embodiments, the extracellular sushi domain of the chimeric transmembrane protein is a sequence of a sushi domain from a wildtype alpha chain of an IL-2 receptor (e.g., any of SEQ ID NO: 3, 4, 26, 27, 28, 29, 30, or 31) having one to five (e.g., one, two, three, four, or five) amino acids removed from the C-terminus of the sushi domain from the wildtype alpha chain of an IL-2 receptor. In some embodiments, the extracellular sushi domain of the chimeric transmembrane protein is a sequence of a sushi domain from a wildtype alpha chain of an IL-2 receptor (e.g., any of SEQ ID NO: 3, 4, 26, 27, 28, 29, 30, or 31) having one to five (e.g., one, two, three, four, or five) amino acids removed from the N-terminus of the sushi domain from the wildtype alpha chain of an IL-2 receptor, and one to five (e.g., one, two, three, four, or five) amino acids removed from the C-terminus of the sushi domain from the wildtype alpha chain of an IL-2 receptor.

In some embodiments, the chimeric transmembrane protein comprises two sushi domains. In some embodiments, each of the sushi domains can independently be any of the sushi domains described herein. In some embodiments, one of the two sushi domains comprises or is SEQ ID NO: 3, and the other of the two sushi domains comprises or is SEQ ID NO: 4.

Transmembrane Domains of an Alpha-Chain of an IL-2 Receptor

In some embodiments, the transmembrane domain from an alpha chain of an IL-2 receptor protein can be about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 22 amino acids, about 10 amino acids to about 20 amino acids, about about 10 amino acids to about 18 amino acids, about 10 amino acids to about 15 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 22 amino acids, about 15 amino acids to about 20 amino acids, about about 15 amino acids to about 18 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 22 amino acids, about 18 amino acids to about 20 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 22 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 50 amino acids, about 30 amino acids to about 45 amino acids, about 30 amino acids to about 40 amino acids, about 30 amino acids to about 35 amino acids, about 35 amino acids to about 50 amino acids, about 35 amino acids to about 45 amino acids, about 35 amino acids to about 40 amino acids, about 40 amino acids to about 50 amino acids, about 40 amino acids to about 45 amino acids, or about 45 amino acids to about 50 amino acids, in length.

In some embodiments of any of the chimeric transmembrane proteins described herein, the transmembrane domain of an alpha chain of an IL-2 receptor can be a transmembrane domain from a wildtype alpha chain of an IL-2 receptor (e.g., a transmembrane domain of a wildtype human alpha chain of an IL-2 receptor, e.g., SEQ ID NO: 5) (e.g., any of the exemplary transmembrane domains of a wildtype alpha chain of an IL-2 receptor listed below or known in the art, e.g., SEQ ID NO: 32, 33, or 34).

```
Exemplary Transmembrane Domain of Wildtype Human
Alpha Chain of IL-2 Receptor
                                           (SEQ ID NO: 5)
VAVAGCVFLLISVLLLSGL Exemplary Transmembrane Domain of Wildtype
Chimpanzee Alpha Chain of IL-2 Receptor
                                          (SEQ ID NO: 32)
Vavagcvfllisvillsgl Exemplary Transmembrane Domain of Wildtype Monkey
Alpha Chain of IL-2 Receptor
                                          (SEQ ID NO: 33)
vavagcvfllisvlllsgl Exemplary Transmembrane Domain of Wildtype Mouse
Alpha Chain of IL-2 Receptor
                                          (SEQ ID NO: 34)
vavasclfllisilllsgltw
```

In some embodiments, the transmembrane domain of an alpha chain of IL-2 receptor comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a transmembrane domain of a wildtype alpha chain of IL-2 receptor (e.g., SEQ ID NO: 5, 32, 33, or 34).

As one skilled in the art can appreciate, when amino acids that are not conserved between transmembrane domains from wildtype alpha chains of IL-2 receptor protein from different species are mutated (e.g., substituted with a different amino acid) they are less likely to cause a decrease in the activity of the transmembrane domain from an alpha chain of IL-2 receptor protein. In contrast, when amino acids that are conserved between the transmembrane domains from wildtype alpha chains of IL-2 receptor protein from different species are mutated (e.g., substituted with a different amino acid) they are more likely to cause a decrease in the activity of the transmembrane domain from an alpha chain of IL-2 receptor protein. In view of this knowledge, one skilled in the art can select which amino acid positions in a transmembrane domain of an alpha chain of an IL-2 receptor protein (e.g., the non-conserved amino acids) can be substituted without decreasing the activity of the transmembrane domain from the alpha chain of an IL-2 receptor protein.

In some embodiments, the transmembrane domain of an alpha chain of an IL-2 receptor protein is a sequence of a transmembrane domain of a wildtype alpha chain of IL-2 receptor protein (e.g., a transmembrane domain of a wildtype human alpha chain of IL-2 receptor protein, e.g., SEQ ID NO: 5) (e.g., SEQ ID NO: 32, 33, or 34) having one to five (e.g., one, two, three, four, or five) amino acids removed from the N-terminus of the transmembrane domain of the alpha chain of the IL-2 receptor protein. In some embodiments, the transmembrane domain of an alpha chain of an IL-2 receptor protein is a sequence of a transmembrane domain of a wildtype alpha chain of an IL-2 receptor protein (e.g., a transmembrane domain of a wildtype human alpha chain of IL-2 receptor protein, e.g., SEQ ID NO: 5) (e.g., SEQ ID NO: 32, 33, or 34) having one to five (e.g., one, two, three, four, or five) amino acids removed from the C-terminus of the transmembrane domain of the alpha chain of the IL-2 receptor protein. In some embodiments, the transmembrane domain of an alpha chain of an IL-2 receptor protein is a sequence of a transmembrane domain of a wildtype alpha chain of IL-2 receptor protein (e.g., a transmembrane domain of a wildtype human alpha chain of IL-2 receptor protein, e.g., SEQ ID NO: 5) (e.g., SEQ ID NO: 32, 33, or 34) having one to five (e.g., one, two, three, four, or five) amino acids removed from the N-terminus of the transmembrane domain of the alpha chain of the IL-2 receptor protein, and one to five (e.g., one, two, three, four, or five) amino acids removed from the C-terminus of the transmembrane domain of the alpha chain of the IL-2 receptor protein.

Additional examples of transmembrane domains from an alpha chain of an IL-2 receptor protein are known in the art.

Intracellular Domains of an Alpha-Chain of IL-2 Receptor

Any of the chimeric transmembrane proteins described herein can comprise an intracellular domain of an alpha chain of an interleukin-2 receptor (e.g., any of the alpha chains of an interleukin-2 receptor described herein). In some embodiments, the intracellular domain of an alpha chain of an interleukin-2 receptor can be about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 20 amino acids, about 12 amino acids to about 18 amino acids, about 12 amino acids to about 16 amino acids, about 12 amino acids to about 14 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 20 amino acids, about 14 amino acids to about 18 amino acids, about 14 amino acids to about 16 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 20 amino acids, about 16 amino acids to about 18 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 20 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 50 amino acids, about 30 amino acids to about 45 amino acids, about 30 amino acids to about 40 amino acids, about 30 amino acids to about 35 amino acids, about 35 amino acids to about 50 amino acids, about 35 amino acids to about 45 amino acids, about 35 amino acids to about 40 amino acids, about 40 amino acids to about 50 amino acids, about 40 amino acids to about 45 amino acids, or about 45 amino acids to about 50 amino acids, in length.

Any of the chimeric transmembrane proteins described herein can comprise an intracellular domain of an alpha chain of interleukin-2 receptor (e.g., an intracellular domain of a wildtype alpha chain of interleukin-2 receptor, e.g., an intracellular domain of a wildtype human alpha chain of interleukin-2 receptor, e.g., SEQ ID NO: 6) (e.g., SEQ ID NO: 35, 36, or 37).

```
Exemplary Intracellular Domain of Wildtype Human
Alpha Chain of IL-2 Receptor
                                       (SEQ ID NO: 6)
TWQRRQRKSRRTI Exemplary Intracellular Domain of Wildtype
Chimpanzee Alpha Chain of IL-2 Receptor
                                       (SEQ ID NO: 35)
twqrrq Exemplary Intracellular Domain of Wildtype Monkey
Alpha Chain of IL-2 Receptor
                                       (SEQ ID NO: 36)
twqrrqrknrrti Exemplary Intracellular Domain of Wildtype Mouse
Alpha Chain of IL-2 Receptor
                                       (SEQ ID NO: 37)
qhrwrksrrti
```

In some embodiments, the intracellular domain of an alpha chain of IL-2 receptor comprises or is a sequence that is at least 60% identical, at least 65% identical, at least 70% identical, at least 75% identical, at least 80% identical, at least 82% identical, at least 84% identical, at least 85%, at least 86% identical, at least 88% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to an intracellular domain of a wildtype alpha chain of IL-2 receptor (e.g., an intracellular domain of a wildtype human alpha chain of IL-2 receptor, e.g., SEQ ID NO: 6) (e.g., SEQ ID NO: 35, 36, or 37).

As one skilled in the art can appreciate, when amino acids that are not conserved between intracellular domains from wildtype alpha chains of IL-2 receptor protein from different species are mutated (e.g., substituted with a different amino acid) they are less likely to cause a decrease in the activity of the intracellular domain from an alpha chain of IL-2 receptor protein. In contrast, when amino acids that are conserved between the intracellular domains from wildtype alpha chains of IL-2 receptor protein from different species are mutated (e.g., substituted with a different amino acid) they are more likely to cause a decrease in the activity of the intracellular domain from an alpha chain of IL-2 receptor protein. In view of this knowledge, one skilled in the art can select which amino acid positions in an intracellular domain of an alpha chain of an IL-2 receptor protein (e.g., the non-conserved amino acids) can be substituted without decreasing the activity of the intracellular domain from the alpha chain of an IL-2 receptor protein.

In some embodiments, the intracellular domain of an alpha chain of an IL-2 receptor protein is a sequence of an intracellular domain of a wildtype alpha chain of IL-2 receptor protein (e.g., an intracellular domain of a wildtype human alpha chain of IL-2 receptor protein, e.g., SEQ ID NO: 6) (e.g., SEQ ID NO: 35, 36, or 37) having one to three (e.g., one, two, or three) amino acids removed from the N-terminus of the intracellular domain of the alpha chain of the IL-2 receptor protein. In some embodiments, the intracellular domain of an alpha chain of an IL-2 receptor protein is a sequence of an intracellular domain of a wildtype alpha chain of an IL-2 receptor protein (e.g., an intracellular domain of a wildtype human alpha chain of IL-2 receptor protein, e.g., SEQ ID NO: 5) (e.g., SEQ ID NO: 32, 33, or 34) having one to three (e.g., one, two, or three) amino acids removed from the C-terminus of the intracellular domain of the alpha chain of the IL-2 receptor protein. In some embodiments, the intracellular domain of an alpha chain of an IL-2 receptor protein is a sequence of an intracellular domain of a wildtype alpha chain of IL-2 receptor protein (e.g., an intracellular domain of a wildtype human alpha chain of IL-2 receptor protein, e.g., SEQ ID NO: 6) (e.g., SEQ ID NO: 35, 36, or 37) having one to three (e.g., one, two, or three) amino acids removed from the N-terminus of the intracellular domain of the alpha chain of the IL-2 receptor protein, and one to three (e.g., one, two, or three) amino acids removed from the C-terminus of the intracellular domain of the alpha chain of the IL-2 receptor protein.

Additional examples of intracellular domains from an alpha chain of an IL-2 receptor protein are known in the art.

Linker Sequences

In some embodiments, the chimeric transmembrane protein comprises a linker sequence positioned between the extracellular IL-2 domain and the extracellular sushi domain. In some embodiments, the chimeric transmembrane protein comprises an additional linker sequence positioned between extracellular sushi domain and the transmembrane domain of an alpha chain of an IL-2 receptor. When the chimeric transmembrane protein comprises a linker sequence and an additional linker sequence, each the linker sequences can be the same or different from each other.

In some embodiments, the linker sequence or the additional linker sequence is 1 amino acid to about 50 amino acids, 1 amino acid to about 48 amino acids, 1 amino acid to about 46 amino acids, 1 amino acid to about 44 amino acids, 1 amino acid to about 42 amino acids, 1 amino acid to about 40 amino acids, 1 amino acid to about 38 amino acids, 1 amino acid to about 36 amino acids, 1 amino acid to about 34 amino acids, 1 amino acid to about 32 amino acids, 1 amino acid to about 30 amino acids, 1 amino acid to about 28 amino acids, 1 amino acid to about 26 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, 1 amino acid to about 3 amino acids, about 2 amino acids to about 50 amino acids, about 2 amino acids to about 48 amino acids, about 2 amino acids to about 46 amino acids, about 2 amino acids to about 44 amino acids, about 2 amino acids to about 42 amino acids, about 2 amino acids to about 40 amino acids, about 2 amino acids to about 38 amino acids, about 2 amino acids to about 36 amino acids, about 2 amino acids to about 34 amino acids, about 2 amino acids to about 32 amino acids, about 2 amino acids to about 30 amino acids, about 2 amino acids to about 28 amino acids, about 2 amino acids to about 26 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 50 amino acids, about 4 amino acids to about 48 amino acids, about 4 amino acids to about 46 amino acids, about 4 amino acids to about 44 amino acids, about 4 amino acids to about 42 amino acids, about 4 amino acids to about 40 amino acids, about 4 amino acids to about 38 amino acids, about 4 amino acids to about 36 amino acids, about 4 amino acids to about 34 amino acids, about 4 amino acids to about 32 amino acids, about 4 amino acids to about 30 amino acids, about 4 amino acids to about 28 amino acids, about 4 amino acids to about 26 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 50 amino acids, about 6 amino acids to about 48 amino acids, about 6 amino acids to about 46 amino acids, about 6 amino acids to about 44 amino acids, about 6 amino acids to about 42 amino acids, about 6 amino acids to about 40 amino acids, about 6 amino acids to about 38 amino acids, about 6 amino acids to about 36 amino acids, about 6 amino acids to about 34 amino acids, about 6 amino acids to about 32 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 50 amino acids, about 8 amino acids to about 48 amino acids, about 8 amino acids to about 46 amino acids, about 8 amino acids to about 44 amino acids, about 8 amino acids to about 42 amino acids, about 8 amino acids to about 40 amino acids, about 8 amino acids to about 38 amino acids, about 8 amino acids to about 36 amino acids, about 8 amino acids to about 34 amino acids, about 8 amino acids to about 32 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 50 amino acids, about 10 amino acids to about 48 amino acids, about 10 amino acids to about 46 amino acids, about 10 amino acids to about 44 amino acids, about 10 amino acids to about 42 amino acids, about 10 amino acids to about 40 amino acids, about 10 amino acids to about 38 amino acids, about 10 amino acids to about 36 amino acids, about 10 amino acids to about 34 amino acids, about 10 amino acids to about 32 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 50 amino acids, about 12 amino acids to about 48 amino acids, about 12 amino acids to about 46 amino acids, about 12 amino acids to about 44 amino acids, about 12 amino acids to about 42 amino acids, about 12 amino acids to about 40 amino acids, about 12 amino acids to about 38 amino acids, about 12 amino acids to about 36 amino acids, about 12 amino acids to about 34 amino acids, about 12 amino acids to about 32 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 50 amino acids, about 14 amino acids to about 48 amino acids, about 14 amino acids to about 46 amino acids, about 14 amino acids to about 44 amino acids, about 14 amino acids to about 42 amino acids, about 14 amino acids to about 40 amino acids, about 14 amino acids to about 38 amino acids, about 14 amino acids to about 36 amino acids, about 14 amino acids to about 34 amino acids, about 14 amino acids to about 32 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 50 amino acids, about 16 amino acids to about 48 amino acids, about 16 amino acids to about 46 amino acids, about 16 amino acids to about 44 amino acids, about 16 amino acids to about 42 amino acids, about 16 amino acids to about 40 amino acids, about 16 amino acids to about 38 amino acids, about 16 amino acids to about 36 amino acids, about 16 amino acids to about 34 amino acids, about 16 amino acids to about 32 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 50 amino acids, about 18 amino acids to about 48 amino acids, about 18 amino acids to about 46 amino acids, about 18 amino acids to about 44 amino acids, about 18 amino acids to about 42 amino acids, about 18 amino acids to about 40 amino acids, about 18 amino acids to about 38 amino acids, about 18 amino acids to about 36 amino acids, about 18 amino acids to about 34 amino acids, about 18 amino acids to about 32 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 50 amino acids, about 20 amino acids to about 48 amino acids, about 20 amino acids to about 46 amino acids, about 20 amino acids to about 44 amino acids, about 20 amino acids to about 42 amino acids, about 20 amino acids to about 40 amino acids, about 20 amino acids to about 38 amino acids, about 20 amino acids to about 36 amino acids, about 20 amino acids to about 34 amino acids, about 20 amino acids to about 32 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 50 amino acids, about 22 amino acids to about 48 amino acids, about 22 amino acids to about 46 amino acids, about 22 amino acids to about 44 amino acids, about 22 amino acids to about 42 amino acids, about 22 amino acids to about 40 amino acids, about 22 amino acids to about 38 amino acids, about 22 amino acids to about 36 amino acids, about 22 amino acids to about 34 amino acids, about 22 amino acids to about 32 amino acids, about 22 amino acids to about 30 amino acids, about 22 amino acids to about 28 amino acids, about 22 amino acids to about 26 amino acids, about 22 amino acids to about 24 amino acids, about 24 amino acids to about 50 amino acids, about 24 amino acids to about 48 amino acids, about 24 amino acids to about 46 amino acids, about 24 amino acids to about 44 amino acids, about 24 amino acids to about 42 amino acids, about 24 amino acids to about 40 amino acids, about 24 amino acids to about 38 amino acids, about 24 amino acids to about 36 amino acids, about 24 amino acids to about 34 amino acids, about 24 amino acids to about 32 amino acids, about 24 amino acids to about 30 amino acids, about 24 amino acids to about 28 amino acids, about 24 amino acids to about 26 amino acids, about 26 amino acids to about 50 amino acids, about 26 amino acids to about 48 amino acids, about 26 amino acids to about 46 amino acids, about 26 amino acids to about 44 amino acids, about 26 amino acids to about 42 amino acids, about 26 amino acids to about 40 amino acids, about 26 amino acids to about 38 amino acids, about 26 amino acids to about 36 amino acids, about 26 amino acids to about 34 amino acids, about 26 amino acids to about 32 amino acids, about 26 amino acids to about 30 amino acids, about 26 amino acids to about 28 amino acids, about 28 amino acids to about 50 amino acids, about 28 amino acids to about 48 amino acids, about 28 amino acids to about 46 amino acids, about 28 amino acids to about 44 amino acids, about 28 amino acids to about 42 amino acids, about 28 amino acids to about 40 amino acids, about 28 amino acids to about 38 amino acids, about 28 amino acids to about 36 amino acids, about 28 amino acids to about 34 amino acids, about 28 amino acids to about 32 amino acids, about 28 amino acids to about 30 amino acids, about 30 amino acids to about 50 amino acids, about 30 amino acids to about 48 amino acids, about 30 amino acids to about 46 amino acids, about 30 amino acids to about 44 amino acids, about 30 amino acids to about 42 amino acids, about 30 amino acids to about 40 amino acids, about 30 amino acids to about 38 amino acids, about 30 amino acids to about 36 amino acids, about 30 amino acids to about 34 amino acids, about 30 amino acids to about 32 amino acids, about 32 amino acids to about 50 amino acids, about 32 amino acids to about 48 amino acids, about 32 amino acids to about 46 amino acids, about 32 amino acids to about 44 amino acids, about 32 amino acids to about 42 amino acids, about 32 amino acids to about 40 amino acids, about 32 amino acids to about 38 amino acids, about 32 amino acids to about 36 amino acids, about 32 amino acids to about 34 amino acids, about 34 amino acids to about 50 amino acids, about 34 amino acids to about 48 amino acids, about 34 amino acids to about 46 amino acids, about 34 amino acids to about 44 amino acids, about 34 amino acids to about 42 amino acids, about 34 amino acids to about 40 amino acids, about 34 amino acids to about 38 amino acids, about 34 amino acids to about 36 amino acids, about 36 amino acids to about 50 amino acids, about 36 amino acids to about 48 amino acids, about 36 amino acids to about 46 amino acids, about 36 amino acids to about 44 amino acids, about 36 amino acids to about 42 amino acids, about 36 amino acids to about 40 amino acids, about 36 amino acids to about 38 amino acids, about 38 amino acids to about 50 amino acids, about 38 amino acids to about 48 amino acids, about 38 amino acids to about 46 amino acids, about 38 amino acids to about 44 amino acids, about 38 amino acids to about 42 amino acids, about 38 amino acids to about 40 amino acids, about 40 amino acids to about 50 amino acids, about 40 amino acids to about 48 amino acids, about 40 amino acids to about 46 amino acids, about 40 amino acids to about 44 amino acids, about 40 amino acids to about 42 amino acids, about 42 amino acids to about 50 amino acids, about 42 amino acids to about 48 amino acids, about 42 amino acids to about 46 amino acids, about 42 amino acids to about 44 amino acids, about 44 amino acids to about 50 amino acids, about 44 amino acids to about 48 amino acids, about 44 amino acids to about 46 amino acids, about 46 amino acids to about 50 amino acids, about 46 amino acids to about 48 amino acids, or about 48 amino acids to about 50 amino acids.

In some embodiments, the linker sequence and/or the additional linker sequence comprises a sequence of $(SG)_n$, where n can be 1, 2, 3, 4, 5, 6, 7, 8, 9, 10, 11, 12, 13, 14, 15, 16, 17, 18, 19, 20, 21, 22, 23, 24, or 25. In some embodiments, the linker sequence and/or the additional linker sequence comprises a sequence of $(GS)_n$, where n can be 1, 2, 3, 4, 5, 6, 7, 8, 9, 10, 11, 12, 13, 14, 15, 16, 17, 18, 19, 20, 21, 22, 23, 24, or 25.

In some embodiments, the linker sequence and/or the additional linker sequence comprises a sequence of $(SGGS)_n$, where n can be 1, 2, 3, 4, 5, 6, 7, 8, 9, 10, 11, 12, or 13. In some embodiments, the linker sequence and/or the additional linker sequence comprises a sequence of $(SGGGS)_n$, where n can be 1, 2, 3, 4, 5, 6, 7, 8, 9, or 10. In some embodiments, the linker sequence and/or the additional linker sequence comprises a sequence of $(SGGGGS)_n$, where n can be 1, 2, 3, 4, 5, 6, 7, 8, or 9.

In some embodiments, the linker sequence and/or the additional linker sequence can be or include the sequence of SGGGGSGGGGSGGGG (SEQ ID NO: 38). In some embodiments, the linker sequence and/or the additional linker sequence can be or include the sequence of ASTKGPSVFPLAPSSSGSG (SEQ ID NO: 39). In some embodiments, the linker sequence and/or the additional linker sequence can be or include the sequence of GGGGSGGGGSGGGGS (SEQ ID NO: 40). In some embodiments, the linker sequence and/or the additional linker sequence can be or include the sequence of GGGSGGGGSGGGGSGGGGSGGGS (SEQ ID NO: 2).

In some embodiments, the linker sequence and/or the additional linker sequence can be a Whitlow linker. In some embodiments, the Whitlow linker has the amino acid sequence of GSTSGSGKPGSGEGSTKG (SEQ ID NO: 41) or the nucleotide sequence encoding the Whitlow linker sequence is ggcagcaccagcggcagcggcaaaccgggcagcggcgaa ggcagcaccaaaggc (SEQ ID NO: 42).

In some embodiments, the linker sequence and/or the additional linker sequence can be a $(G_4S)_5$ linker. In some embodiments, the $(G_4S)_5$ linker has the amino acid sequence of GGGGSGGGGSGGGGSGGGGSGGGGS (SEQ ID NO: 43) or the nucleotide sequence encoding the $(G_4S)_5$ linker sequence is ggcggtggtggttctggaggcggtgg cagcggtg-gaggtggctcaggaggaggaggtagcggcggcggagggagt (SEQ ID NO: 44).

In some embodiments, the linker sequence and/or the additional linker sequence can be or can include one or more of an IgG1, IgG2, IgG3, or IgG4 CH1, CH2, and CH3 domain. In some embodiments, the linker sequence and/or the additional linker sequence can be or can include CH2-CH3 human IgG1 domains. In some embodiments, the CH2-CH3 human IgG1 domains have a sequence of:

(SEQ ID NO: 45)
AEPKSPDKTHTCPPCPAPPVAGPSVFLFPPKPKDTLMIARTPEVTCWVDVS

HEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQG

NVFSCSVMHEALHNHYTQKSLSLSPGKKD.

In some embodiments, the linker sequence and/or the additional linker sequence can be or include a portion of the human CD8 extracellular sequence that is proximal to the human CD8 transmembrane domain. For example, the linker sequence and/or the additional linker sequence can be or include human CD8 sequence of:

(SEQ ID NO: 46)
TTTPAPRPPTPAPTIASQPLSLRPEACRPAAGGAVHTRGLDFACDI.

In some embodiments, the linker sequence and/or the additional linker sequence can be or include a human IgG1 hinge sequence. In some embodiments, the human IgG1 hinge sequence is AEPKSPDKTHTCPPCPKDPK (SEQ ID NO: 47).

In some embodiments, the linker sequence and/or the additional linker sequence has an alpha helix structure. In some embodiments, the linker sequence and/or the additional linker sequence is a coiled coil domain.

In some embodiments, the linker sequence and/or the additional linker sequence is a naturally-occurring amino acid sequence. In some embodiments, the linker sequence and/or the additional linker sequence is not a naturally-occurring amino acid sequence. In some embodiments, the linker sequence and/or the additional linker sequence comprises a sequence of SEQ ID NO: 2. In some embodiments, the linker sequence and/or the additional linker sequence consists of a sequence of SEQ ID NO: 2. Additional aspects and examples of linkers are known in the art.

Chimeric Antigen Receptors

A chimeric antigen receptor (CAR) is a protein that includes an extracellular antigen-binding domain (e.g., any of the antigen-binding domains described herein or known in the art), a transmembrane domain (e.g., any of the transmembrane domains described herein or known in the art), a costimulatory domain (e.g., any of the costimulatory domains described herein or known in the art), and an immunoreceptor tyrosine-based activation motif (ITAM). Non-limiting aspects of chimeric antigen receptors are described in, e.g., Kershaw et al., *Nature Reviews Immunol.* 5(12):928-940, 2005; Eshhar et al., *Proc. Natl. Acad. Sci. U.S.A.* 90(2):720-724, 1993; Sadelain et al., *Curr. Opin. Immunol.* 21(2): 215-223, 2009; WO 2015/142675; WO 2015/150526; and WO 2014/134165, the disclosures of each of which are incorporated herein by reference in their entirety.

Some embodiments, a chimeric antigen receptors can include one or more (e.g., two, three, four, or five) costimulatory domain(s) (e.g., any combination of any of the exemplary costimulatory domains described herein or known in the art). Some embodiments of these chimeric antigen receptors include one or both of a 4-1BB costimulatory domain and a CD28 costimulatory domain.

Some embodiments, a chimeric antigen receptor can include one or more (e.g., two, three, four, or five) ITAMs (e.g., any of the ITAMs described herein or known in the art). In some embodiments of these chimeric antigen receptors, the ITAM includes a cytoplasmic signaling sequence from CD3 (e.g., human CD3).

In some embodiments, one or more amino acids between the extracellular antigen-binding domain and the transmembrane domain is a sequence from the same endogenous single-chain polypeptide from which the transmembrane domain is derived. In some embodiments, one or more amino acids between the extracellular antigen-binding domain and the transmembrane domain is or includes a hinge region sequence of an antibody such as, without limitation, a human antibody (e.g., IgG1, IgG2, IgG3, or IgG4). In some embodiments, one or more amino acids between the extracellular antigen-binding domain and the transmembrane domain is or comprises a linker sequence (e.g., a non-naturally occurring linker sequence, e.g., GS or any of the other linker sequences described herein).

In some examples of any of the CARs described herein, going in the N-terminal to the C-terminal direction, the intracellular portion of the CAR includes a co-stimulatory domain and an intracellular signaling domain. In some examples of any of the CARs described herein, going in the N-terminal to the C-terminal direction, the intracellular portion of the CAR includes an intracellular signaling domain and a co-stimulatory domain.

In some examples of any of the CARs described herein, going in the C-terminal to the N-terminal direction, the intracellular portion of the CAR includes a co-stimulatory domain and an intracellular signaling domain. In some examples of any of the CARs described herein, going in the C-terminal to the N-terminal direction, the intracellular portion of the CAR includes an intracellular signaling domain and a co-stimulatory domain.

In some embodiments of any of the CARs described herein, the transmembrane is or includes a transmembrane domain of CD28, CD3 epsilon, CD4, CD5, CD6, CD8a, CD9, CD16, CD22, CD33, CD37, CD 45, CD64, CD80, CD86, CD134, 4-1BB, or CD154. Additional examples and aspects of transmembrane domains are described herein.

In some embodiments of any of the CARs described herein, the co-stimulatory domain is or includes the costimulatory domain of 4-1BB, CD28, CD2, CD4 or CD8. Additional examples and aspects of co-stimulatory domains are described herein.

A variety of methods that can be used to determine the $K_D$ values of any of the CARs described herein are known in the art (e.g., an electrophoretic mobility shift assay, a filter binding assay, surface plasmon resonance, and a biomolecular binding kinetics assay, etc.).

Some embodiments of any of the chimeric antigen receptors described herein can further include a dimerization domain and/or a peptide tag.

Antigen-Binding Domains

In some embodiments of the chimeric antigen receptors, the antigen-binding domain can be selected from a scFv, a scFv-Fc, a VHH domain, a VNAR domain, a (scFv)$_2$, and a BiTE. Additional examples of antigen-binding domains that can be used the chimeric antigen receptors described herein are known in the art.

A single-chain Fv or scFv fragment includes a $V_H$ domain and a $V_L$ domain in a single polypeptide chain. The $V_H$ and $V_L$ are generally linked by a peptide linker. In other examples, the linker can be a single amino acid. In some examples, the linker can be a chemical bond. See, e.g., Pluckthun, Antibodies from E. coli. In Rosenberg M. & Moore GP. (Eds.), The Pharmacology of Monoclonal Antibodies, Vol. 113, pp. 269-315, Spinger-Verlag, New York, 1994.

Sc-Fv-Fc fragments include an scFv attached to an Fc domain. For example, an Fc domain can be attached, e.g., to the C-terminus of the scFv. The Fc domain can follow the $V_L$ or $V_H$, depending on the orientation of the variable domains in the scFv. The Fc domain can be any Fc domain known in the art. In some examples, the Fc domain is an IgG1, IgG2, IgG3, or IgG4 Fc domain (e.g., a human IgG1, IgG2, IgG3, or IgG4 Fc domain).

BiTEs are antigen-binding domains that include two $V_L$ and two $V_H$ in a single polypeptide that together form two scFvs, which can each bind to different epitopes on the same antigen or each bind to different antigens. See, e.g., Baeuerle et al., Curr. Opin. Mol. Ther 11:22-30, 2009; Wolf et al., Drug Discovery Today 10:1237-1244, 2005; and Huehls et al., Immunol. Cell Biol. 93:290-296, 2015.

A $V_H$H domain is a single monomeric variable antibody domain found in camelids, and a $V_{NAR}$ domain is a single monomeric variable antibody domain found in cartilaginous fish. $V_H$H domains and $V_{NAR}$ domains are described in, e.g., Van Audenhove et al., EBioMedicine 8:40-48, 2016; Krah et al., Immunopharmacol. Immunotoxicol. 38:21-28, 2016; Cromie et al., Curr. Top. Med. Chem. 15:2543-2557, 2016; Kijanka et al., Nanomedicine 10:161-174, 2015; Kovaleva et al., Expert. Opin. Biol. Ther. 14:1527-1539, 2014; De Meyer et al., Trends Biotechnol. 32:263-270, 2014; Mujic-Delic et al., Trends Pharmacol. Sci. 35:247-255, 2014; Muyldermans, Ann. Rev. Biochem. 82:775-797, 2013; Vincke et al., Methods Mol. Biol. 911:15-26, 2012; Rahbarizadeh et al., Immunol. Invest. 40:299-338, 2011; Van Bockstaele et al., Curr. Opin. Investig. Drugs 10:1212-1224, 2009; Wesolowski et al., Med. Microbiol. Immunol. 198:157-174, 2009; De Genst et al., Dev. Comp. Immunol. 30:187-198, 2006; Muyldermans, J. Biotechnol. 74:277-302, 2001; and Muyldermans et al., Trends Biochem. Sci. 26:230-235, 2001.

Any of the antigen-binding domains described herein can bind to an antigen with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the antigen-binding protein complexes provided herein can bind to a first and/or second antigen with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive). A variety of different methods known in the art can be used to determine the $K_D$ value of an antigen-binding domain (e.g., an electrophoretic mobility shift assay, a filter binding assay, surface plasmon resonance, and a biomolecular binding kinetics assay, etc.).

Antigens

In some embodiments, a chimeric antigen receptor described herein can bind to a single antigen (e.g., any of the exemplary antigens described herein or known in the art). In some embodiments, an antigen-binding domain described herein can bind to two or more different antigens (e.g., two or more of any of the exemplary antigens described herein or known in the art). Non-limiting examples of antigens include: glypican-3, HER2, A33 antigen, 9-0-acetyl-GD3, CA19-9 marker, BhCG, CA-125 marker, carboanhydrase IX (MN/CA IX), calreticulin, CCR5, CCR8, CD2, CD3, CD5, CD16, CD19, CD20, CD22, CD24, CD25, CD27, CD28, CD30, CD33, CD38, CD40L, CD44, CD44V6, CD63, CD70, CD84, CD96, CD100, CC123, CD133, CD137, CD138, CD150, CD152 (CTLA-4), CD160, CRTAM, CS1 (CD319), DNAM-1 (CD226), CD229, CD244, CD272 (BTLA), CD274 (PDL-1, B7H1), CD279 (PD-1), CD319, CD352, CRTAM (CD355), CD358, DR3, GITR (TNFRSF 18), HVEM, ICOS, LIGHT, LTBR, OX40, activating forms of KIR, NKG2C, NKG2D, NKG2E, one or more natural cytotoxicity receptors, NTB-A, PEN-5, carcinoma embryonic antigen (CEA; CD66e), desmoglein 4, E-cadherin neoepitope, endosialin, ephrin A2 (EphA2), epidermal growth factor receptor (EGFR), epithelial cell adhesion molecule (EpCAM), fucosyl GM1, GD2, GD3, GM2, ganglioside GM3, Globo H, glycoprotein 100, HER2/neu, HER3, HER4, insulin-like growth factor receptor 1, Lewis-Y, LG, Ly-6, melanoma-specific chondroitin-sulfate proteoglycan (MCSCP), mesothelin, MUC1, MUC2, MUC3, MUC4, MUC5AC, MUC5$_b$, MUC7, MUC16, Mullerian inhibitory substance (MIS) receptor type II, plasma cell antigen, poly SA, PSCA, PSMA, sonic hedgehog (SHH), SAS, STEAP, sTn antigen, TNF-α precursor, 2B4 (CD244), β2-integrins, KIR, KIR2DL1, KIR2DL2, KIR2DL3, KIR3DL2, KIR-L, KLRGI, LAIR-1, NKG2A, NKR-P IA, Siglec-3, Siglec-7, Siglec-9, TCRa, TCRB, TCR5y, TIM1, LAG3, LAIR1, PD-1H, TIGIT, TIM2, and TIM3. Additional examples of antigens are known in the art.

CAR Transmembrane Domains

In some embodiments, a chimeric antigen receptor includes a transmembrane domain, or portion thereof, from an endogenous polypeptide, where the endogenous polypeptide is selected from the group g of: an a chain of a T cell receptor, a β chain of the T cell receptor, a ζ chain of to the T cell receptor, CD28 (also known as Tp44), CD3ε, CD3δ, CD3γ, CD33, CD37 (also known as GP52-40 or TSPAN26), CD64 (also known as FCGR1A), CD80 (also known as B7, B7-1, B7.1, BB1, CD28LG, CD28LG1, and LAB7), CD45 (also known as PTPRC, B220, CD45R, GP180, L-CA, LCA, LYS, T200, and protein tyrosine phosphatase, receptor type C), CD4, CD5 (also known as LEU1 and T1), CD8a (also known as Leu2, MAL, and p32), CD9 (also known as BTCC-1, DRAP-27, MIC3, MRP-1, TSPAN-29, and TSPAN29), CD16 (also known as FCGR3 andFCG3), CD22 (also known as SIGLEC-2 and SIGLEC2), CD86 (also known as B7-2, B7.2, B70, CD28LG2, and LAB72), CD134 (also known as TNFRSF4, ACT35, RP5-902P8.3, IMD16, OX40, TXGP1L, and tumor necrosis factor receptor superfamily member 4), CD137 (also known as TNFRSF9, 4-1BB, CDw137, ILA, and tumor necrosis factor receptor superfamily member 9), CD27 (also known as S152, S152.LPFS2, T14, TNFRSF7, and Tp55), CD152 (also known as CTLA4, ALPS5, CELIAC3, CTLA-4, GRD4, GSE, IDDM12, and cytotoxic T-lymphocyte associated protein 4), PD1 (also known as PDCD1, CD279, PD-1, SLEB2, hPD-1, hPD-1, hSLE1, and Programmed cell death 1), ICOS (also known as AILIM, CD278, and CVID1), CD272 (also known as BTLA and BTLA1), CD30 (also known as TNFRSF8, D1S166E, and Ki-1), GITR (also known as TNFRSF18, RP5-902P8.2, AITR, CD357, and GITR-D), HVEM (also known as TNFRSF14, RP3-395M20.6, ATAR, CD270, HVEA, HVEM, LIGHTR, and TR2), DAP10, and CD154 (also known as CD40LG, CD40L, HIGM1, IGM, IMD3, T-BAM, TNFSF5, TRAP, gp39, hCD40L, and CD40 ligand). The letters "CD" is the previous sentence stand for "Cluster of Differentiation." E.g., CD3 stands for "Cluster of Differentiation 3." In some embodiments, a chimeric antigen receptor includes a transmembrane domain, or portion thereof, from an endogenous mammalian (e.g., human) polypeptide (e.g., a mammalian or human homolog of any of the polypeptides listed above).

Any transmembrane domain, or portion thereof, that serves to anchor an endogenous polypeptide in a lipid bilayer (e.g., plasma membrane) of a mammalian cell is suitable for use in accordance with compositions and methods disclosed herein. In some embodiments, a chimeric antigen receptor includes a transmembrane domain, or portion thereof, from human CD28, e.g., Accession No. P01747, e.g., amino acids 153 to 179 of SEQ ID NO: 48. In some embodiments, a chimeric antigen receptor includes a transmembrane domain that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 153 to 179 of SEQ ID NO: 48, or a portion thereof.

```
                                            SEQ ID NO: 48
MLRLLLALNLFPSIQVTGNKILVKQSPMLVAYDNAVNLSCKYSYNLFSREF

RASLHKGLDSAVEVCVVYGNYSQQLQVYSKTGFNCDGKLGNESVTFYLQNL

YVNQTDIYFCKIEVMYPPPYLDNEKSNGTIIHVKGKHLCPSPLFPGPSKPF

WVLVVVGGVLACYSLLVTVAFIIFWVRSKRSRLLHSDYMNMTPRRPGPTRK

HYQPYAPPRDFAAYRS
```

In some embodiments, a chimeric antigen receptor includes a transmembrane domain, or portion thereof, from human CD3, e.g., Accession No. P20963, e.g., amino acids 31 to 51 of SEQ ID NO: 49. In some embodiments, a chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 31 to 51 of SEQ ID NO: 49.

```
                                            SEQ ID NO: 49
MKWKALFTAAILQAQLPITEAQSFGLLDPKLCYLLDGILFIYGVILTALFL

RVKFSRSADAPAYQQGQNQLYNELNLGRREEYDVLDKRRGRDPEMGGKPQR

RKNPQEGLYNELQKDKMAEAYSEIGMKGERRRGKGHDGLYQGLSTATKDTY

DALHMQALPPR
```

In some embodiments, a chimeric antigen receptor includes a transmembrane domain, or portion thereof, of any one of SEQ ID Nos. 50-56.

```
                                            (SEQ ID NO: 50)
LGLLVAGVLVLLVSLGVAIHLCC;

(SEQ ID NO: 51)
VAAILGLGLVLGLLGPLAILLALYLL;

(SEQ ID NO: 52)
ALIVLGGVAGLLLFIGLGIFFCVRC;

(SEQ ID NO: 53)
LCYLLDGILFIYGVILTALFLRV;

(SEQ ID NO: 54)
WVLVVVGGVLACYSLLVTVAFIIFWV;

(SEQ ID NO: 55)
IYIWAPLAGTCGVLLLSLVITLYC;
and (SEQ ID NO: 56)
ALPAALAVISFLLGLGLGVACVLA.
```

In some embodiments, a chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to any one of SEQ ID Nos. 50-56.

As will be appreciated by those of ordinary skill in the art, certain endogenous polypeptides have two or more isoforms that differ at least in their primary polypeptide sequence. A chimeric antigen receptor disclosed herein can include a transmembrane domain that includes a sequence of amino acids from any isoform of an endogenous transmembrane protein (e.g., an endogenous mammalian, e.g., human, transmembrane protein) including, e.g., an isoform (e.g., a human isoform) of: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8a, CD9, CD16, CD22, CD86, CD134, CD137, CD27, CD152, PD1, or CD154.

In some embodiments, a transmembrane domain, or portion thereof, of a chimeric antigen receptor includes a sequence of amino acids that exhibits at least 85%, 86%, 87%, 88%, 89%, 90%, 91%, 92%, 93%, 94%, 95%, 96%, 97%, 98%, 99% or more sequence identity to the transmembrane domains from one or more of the following endogenous mammalian (e.g., human) transmembrane proteins: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8a, CD9, CD16, CD22, CD86, CD134, CD137, CD27, CD152, PD1, or CD154. In some embodiments, a transmembrane domain, or portion thereof, of a chimeric antigen receptor includes a sequence of amino acids having one or more amino acid substitutions, deletions, or additions as compared to the transmembrane domain of an endogenous mammalian (e.g., human) transmembrane protein: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8a, CD9, CD16, CD22, CD86, CD134, CD137, CD27, CD152, PD1, or CD154.

In some embodiments, a chimeric antigen receptor includes a synthetic transmembrane domain. In some cases, a synthetic transmembrane domain can include predominantly hydrophobic residues such as, without limitation, leucine and valine. In some embodiments, a synthetic transmembrane domain includes a triplet of phenylalanine, tryptophan, and valine at each end of the domain.

In some embodiments, a chimeric antigen receptor includes a transmembrane domain that is a chimeric transmembrane domain having portions of a transmembrane domain from two or more endogenous mammalian (e.g., human) transmembrane polypeptides such as, without limitation, an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8a, CD9, CD16, CD22, CD86, CD134, CD137, CD27, CD152, PD1, and CD154, such that the two or more portions of transmembrane domains together constitute a functional transmembrane domain. In some embodiments, such a portion of a chimeric transmembrane domain can include one or more amino acid substitutions, deletions, or additions as compared to a corresponding portion of a wild type transmembrane domain.

A transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Additional examples and features of transmembrane domains are known in the art.

Costimulatory Domains

In normal lymphocytes, T cell activation is mediated by two classes of intracellular signaling domains. Primary signaling is initiated via MHC-mediated antigen-dependent activation via the T cell receptor (e.g., a TCR/CD3 complex). A secondary or costimulatory signal is provided by a different receptor that includes a costimulatory signaling domain, which acts in an antigen-independent manner. Signals generated through the signaling domain of the TCR alone are insufficient for complete T cell activation; a co-stimulatory signal is also required.

In some embodiments, a chimeric antigen receptor includes a costimulatory domain, or portion thereof, from an endogenous mammalian (e.g., human) transmembrane polypeptide selected from the group of: CD27 (also known as 5152, S152.LPFS2, T14, TNFRSF7, and Tp55), CD28 (also known as Tp44), 4-1BB (also known as TNFRSF9, CD137, CDw137, ILA, and tumor necrosis factor receptor superfamily member 9), OX40 (also known as TNFRSF4, ACT35, RP5-902P8.3, IMD16, CD134, TXGP1L, and tumor necrosis factor receptor superfamily member 4), CD30 (also known as TNFRSF8, D1S166E, and Ki-1), CD40L (also known as CD40LG, CD154, HIGM1, IGM, IMD3, T-BAM, TNFSF5, TRAP, gp39, hCD40L, and CD40 ligand), CD40 (also known as Bp50, CDW40, TNFRSF5, p50, CD40 (protein), and CD40 molecule), PD-1 (also known as PDCD1, CD279, PD-1, SLEB2, hPD-1, hPD-1, hSLE1, and Programmed cell death 1), PD-L1 (also known as CD274, B7-H, B7H1, PD-L1, PDCD1L1, PDCD1LG1, PDL1, CD274 molecule, and Programmed cell death 1 ligand 1), ICOS (also known as AILIM, CD278, and CVID1), LFA-1 (also known as Lymphocyte function-associated antigen 1), CD2 (also known as LFA-2, SRBC, T11, and CD2 molecule), CD7 (also known as GP40, LEU-9, TP41, Tp40, and CD7 molecule), CD160 (also known as BY55, NK1, NK28, and CD160 molecule), LIGHT (also known as TNFSF14, CD258, HVEML, LIGHT, LTg, TR2, TNLG1D, and tumor necrosis factor superfamily member 14), BTLA (also known as CD272 and BTLA1), TIM3 (also known as HAVCR2, HAVcr-2, KIM-3, TIM3, TIMD-3, TIMD3, Tim-3, CD366, and hepatitis A virus cellular receptor 2), CD244 (also known as 2B4, NAIL, NKR2B4, Nmrk, SLAMF4, and CD244 molecule), CD80 (also known as B7, B7-1, B7.1, BB1, CD28LG, CD28LG1, LAB7, and CD80 molecule), LAG3 (also known as CD223 and lymphocyte activating 3), NKG2C (also known as CD314, D12S2489E, KLR, NKG2-D, NKG2D, and killer cell lectin like receptor K1), GITR (also known as TNFRSF18, RP5-902P8.2, AITR, CD357, and GITR-D), HVEM (also known as TNFRSF14, RP3-395M20.6, ATAR, CD270, HVEA, HVEM, LIGHTR, and TR2), TLR1, TLR2, TLR3, TLR4, TLR5, TLR6, TLR7, TLR8, TLR9, TLRIO, CARD11, CD54 (ICAM), CD83, DAP10, LAT, SLP76, TRIM, ZAP70, and B7-H3 (also known as CD276, 4Ig-B7-H3, B7H3, B7RP-2, and CD276 molecule). The letters "CD" is the previous sentence stand for "Cluster of Differentiation." For example, CD3 stands for "Cluster of Differentiation 3." In some embodiments, a single-chain chimeric polypeptide, a single-chain chimeric antigen receptor, or a multi-chain chimeric antigen receptor includes a costimulatory domain, or portion thereof, from an endogenous mammalian (e.g., human) transmembrane polypeptide (e.g., a mammalian or human homolog of any of the polypeptides listed above).

Any costimulatory domain, or portion thereof, that serves to provide a costimulatory signal is suitable for use in accordance with compositions and methods disclosed herein. In some embodiments, a chimeric antigen receptor includes a costimulatory domain, or portion thereof, from human CD28 (e.g. Accession No. P01747, e.g., from amino acids 180 to 220 of SEQ ID NO: 57). In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 57, or a fragment thereof.

SEQ ID NO: 57
MLRLLLALNLFPSIQVTGNKILVKQSPMLVAYDNAVNLSCKYSYNLFSREF

RASLHKGLDSAVEVCVVYGNYSQQLQVYSKTGFNCDGKLGNEVTFYLQNLY

VNQTDIYFCKIEVMYPPPYLDNEKSNGTIIHVKGKHLCPSPLFPGPSKPFW

VLVVVGGVLACYSLLVTVAFIIFWVRSKRSRLLHSDYMNMTPRRPGPTRKH

YQPYAPPRDFAAYRS

In some embodiments, a chimeric antigen receptor includes a costimulatory domain, or portion thereof, from human 4-1BB (e.g. Accession No. Q07011, e.g., from amino acids 214 to 255 of SEQ ID NO: 58). In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to amino acids 214 to 255 of SEQ ID NO: 58, or a portion thereof.

SEQ ID NO: 58
MGNSCYNIVATLLLVLNFERTRSLQDPCSNCPAGTFCDNNRNQICSPCPPN

SFSSAGGQRTCDICRQCKGVFRTRKECSSTSNAECDCTPGFHCLGAGCSMC

EQDCKQGQELTKKGCKDCCFGTFNDQKRGICRPWTNCSLDGKSVLVNGTKE

RDVVCGPSPADLSPGASSVTPPAPAREPGHSPQIISFFLALTSTALLFLLF

FLTLRFSVVKRGRKKLLYIFKQPFMRPVQTTQEEDGCSCRFPEEEEGGCEL

A chimeric antigen receptor disclosed herein can include a costimulatory domain that includes a sequence of amino acids from any isoform of an endogenous mammalian (e.g., human) transmembrane polypeptide having a costimulatory domain including, e.g., an isoform of: CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides).

In some embodiments, a costimulatory domain, or portion thereof, of a chimeric antigen receptor includes a sequence of amino acids that exhibits at least 85%, 86%, 87%, 88%, 89%, 90%, 91%, 92%, 93%, 94%, 95%, 96%, 97%, 98%, 99% or more sequence identity to a costimulatory domain from one or more of a mammalian (e.g., human) CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3. In some embodiments, a costimulatory domain, or portion thereof, of a chimeric antigen receptor includes a sequence of amino acids having one or more amino acid substitutions, deletions, or additions as compared to a costimulatory domain of one or more of an endogenous mammalian (e.g., human) transmembrane polypeptide: an α chain of a T cell receptor, a β chain of the T cell receptor, a chain of the T cell receptor, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides).

In some embodiments, a chimeric antigen receptor includes a costimulatory domain that is a chimeric costimulatory domain having portions of a costimulatory domain from two or more endogenous mammalian (e.g., human) transmembrane polypeptides including, without limitation, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides), such that the two or more portions of the transmembrane domains together constitute a functional costimulatory domain. In some embodiments, such a portion of a chimeric costimulatory domain can include one or more amino acid substitutions, deletions, or additions as compared to a corresponding portion of a wildtype costimulatory domain.

A costimulatory domain of a chimeric antigen receptor disclosed herein can be of any suitable length. For example, a costimulatory domain can have a length of about 20 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, or about 25 amino acids (inclusive); about 25 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, or about 30 amino acids (inclusive); about 30 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, or about 35 amino acids (inclusive); about 35 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, or about 40 amino acids (inclusive); about 40 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, or about 45 amino acids (inclusive); about 45 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, or about 50 amino acids (inclusive); about 50 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, or about 55 amino acids (inclusive); about 55 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, or about 60 amino acids (inclusive); about 60 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, or about 65 amino acids (inclusive); about 65 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, or about 70 amino acids (inclusive); about 70 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, or about 80 amino acids (inclusive); about 80 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, or about 90 amino acids (inclusive); about 90 amino acids to about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, or about 100 amino acids (inclusive); about 100 amino acids to about 200 amino acids, about 190 amino acids, about 180 amino acids, about 170 amino acids, about 160 amino acids, about 150 amino acids, about 140 amino acids, about 130 amino acids, about 120 amino acids, or about 110 amino acids (inclusive); about 110 amino acids to about 200 amino acids, about 190 amino acids, about 180 amino acids, about 170 amino acids, about 160 amino acids, about 150 amino acids, about 140 amino acids, about 130 amino acids, or about 120 amino acids (inclusive); about 120 amino acids to about 200 amino acids, about 190 amino acids, about 180 amino acids, about 170 amino acids, about 160 amino acids, about 150 amino acids, about 140 amino acids, or about 130 amino acids (inclusive); about 130 amino acids to about 200 amino acids, about 190 amino acids, about 180 amino acids, about 170 amino acids, about 160 amino acids, about 150 amino acids, or about 140 amino acids (inclusive); about 140 amino acids to about 200 amino acids, about 190 amino acids, about 180 amino acids, about 170 amino acids, about 160 amino acids, or about 150 amino acids (inclusive); about 150 amino acids to about 200 amino acids, about 190 amino acids, about 180 amino acids, about 170 amino acids, or about 160 amino acids (inclusive); about 160 amino acids to about 200 amino acids, about 190 amino acids, about 180 amino acids, or about 170 amino acids (inclusive); about 170 amino acids to about 200 amino acids, about 190 amino acids, or about 180 amino acids (inclusive); about 180 amino acids to about 200 amino acids or about 190 amino acids (inclusive); or about 190 amino acids to about 200 amino acids (inclusive).

In some embodiments, a chimeric antigen receptor includes two or more costimulatory domains, e.g., two, three, four, or five, or more costimulatory domains. In some embodiments, the two or more costimulatory domains are identical (e.g., they have the same amino acid sequence). In some embodiments, the costimulatory domains are not identical. For example, the costimulatory domains can be selected from different endogenous mammalian (e.g., human) transmembrane polypeptides including, without limitation, CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAG3, NKG2C, or B7-H3 (including, without limitation, a mammalian or human homolog of any of these polypeptides). In some embodiments, the two or more costimulatory domains can differ from each other by one or more (e.g., two, three, four, or five) amino acid substitutions, deletions, or additions. In some embodiments, the two or more costimulatory domains exhibit at least 85%, 86%, 87%, 88%, 89%, 90%, 91%, 92%, 93%, 94%, 95%, 96%, 97%, 98%, 99% or more sequence identity to each other.

Immunoreceptor Tyrosine-Based Activation Motifs (ITAMs)

ITAMs include a tyrosine separated from a leucine or isoleucine by any two other amino acids, and can thus be represented as, e.g., Tyr-X-X-Leu/Ile. ITAMs are typically repeated (e.g., two or more times) in the cytoplasmic tails of certain cell surface proteins of the immune system, and are typically separated by between six and eight amino acids.

In some embodiments, a chimeric antigen receptor includes an ITAM, or portion thereof, from an endogenous mammalian (e.g., human) polypeptide, wherein endogenous mammalian (e.g., human) polypeptide is selected from the group of: CD3ζ (also referred to as CD3 zeta), CD3− (CD3 delta), CD3ε (CD3 epsilon), CD3γ (CD3 gamma), DAP12, FCεR1γ (Fc epsilon receptor I gamma chain), FcRy, FcRft, CD35, CD22, CD79A (antigen receptor complex-associated protein alpha chain), CD79B (antigen receptor complex-associated protein beta chain), and CD66d. The letters "CD" is the previous sentence stand for "Cluster of Differentiation." For example, CD3 stands for "Cluster of Differentiation 3."

Any ITAM, or portion thereof, that serves to mediate signaling in an endogenous mammalian (e.g., human) transmembrane protein suitable for use in accordance with compositions and methods disclosed herein. In some embodiments, a chimeric antigen receptor includes an ITAM, or portion thereof, from human CD3 zeta (e.g. Accession No. P20963, e.g., an ITAM present in amino acids 52-164 of SEQ ID NO: 59, or a portion thereof; or SEQ ID NO: 60 or a portion thereof). In some embodiments, an ITAM comprises a sequence that is at least 80% (e.g., at least 82%, at least 84%, at least 86%, at least 88%, at least 90%, at least 92%, at least 94%, at least 96%, at least 98%, at least 99%, or 100% identical to: the sequence of amino acids 52-165 of SEQ ID NO: 59 (or a portion thereof), or the sequence of SEQ ID NO: 60 (or a portion thereof).

SEQ ID NO: 59
MKWKALFTAAILQAQLPITEAQSFGLLDPKLCYLLDGILFIYGVILTALFL

RVKFSRSADAPAYQQGQNQLYNELNLGRREEYDVLDKRRGRDPEMGGKPQR

RKNPQEGLYNELQKDKMAEAYSEIGMKGERRRGKGHDGLYQGLSTATKDTY

DALHMQALPPR

-continued (Human CD3 zeta signaling domain)
SEQ ID NO: 60
LRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTY

DALHMQALPPR (cDNA encoding human CD3 zeta signaling domain of
SEQ ID NO: 60)
SEQ ID NO: 61
ctgagagtgaagttcagcaggagcgcagacgccccgcgtaccagcagggc cagaaccagctctataacgagctcaatctaggacgaagagaggagtacgat gttttggacaagagacgtggccgggaccctgagatgggggaaagccgaga aggaagaaccctcaggaaggcctgtacaatgaactgcagaaagataagatg gcggaggcctacagtgagattgggatgaaaggcgagcgccggaggggcaag gggcacgatggcctttaccagggtctcagtacagccaccaaggacacctac gacgccttcacatgcaggccctgccccctcgc As will be appreciated by those of ordinary skill in the art, certain polypeptides have two or more isoforms that differ at least in their primary polypeptide sequence. For example, different isoforms can be generated as a result of alternative splicing. A chimeric antigen receptor disclosed herein can include an ITAM that includes a sequence of amino acids from any isoform of an endogenous mammalian transmembrane polypeptide having an ITAM including, e.g., a mammalian (e.g., human) isoform of: CD3ζ, CD3D, CD3E, CD3G, DAP12, FCER1G, FcRy, FcRft, CD35, CD22, CD79A, CD79B, or CD66d.

In some embodiments, an ITAM, or portion thereof, of a chimeric antigen receptor includes a sequence of amino acids having one or more (e.g., two, three, four, or five) amino acid substitutions, deletions, or additions as compared to an ITAM of one or more of an ITAM in an endogenous mammalian (e.g., human) transmembrane protein, such as, CD3ζ, CD3D, CD3ε, CD3G, DAP12, FCER1G, FcRy, FcRft, CD35, CD22, CD79A, CD79B, or CD66d. For example, the tyrosine and leucine or isoleucine of an ITAM could be retained, while the two amino acids separating them could be replaced with different amino acids.

In some embodiments, a chimeric antigen receptor includes an ITAM that is a chimeric ITAM having portions of an ITAM from two or more endogenous mammalian (e.g., human) transmembrane polypeptides including, without limitation, CD3ζ, CD3D, CD3E, CD3G, DAP12, FCER1G, FcRy, FcRft, CD35, CD22, CD79A, CD79B, or CD66d (including, without limitation, a mammalian or human homolog of any of these polypeptides), such that the two or more ITAM portions together constitute a functional ITAM. In some embodiments, such a portion of a chimeric ITAM can include one or more amino acid substitutions, deletions, or additions as compared to a corresponding portion of a wild type ITAM.

In some embodiments, a chimeric antigen receptor includes two or more ITAMs, e.g., two, three, four, or five, or more ITAMs. In some embodiments, the two or more ITAMs are identical (e.g., they have the same amino acid sequence). In some embodiments, the two or more ITAMs are not identical. For example, the ITAMs can be selected from different endogenous mammalian (e.g., human) transmembrane polypeptides including, without limitation, CD3ζ, CD3D, CD3E, CD3G, DAP12, FCER1G, FcRy, FcRft, CD35, CD22, CD79A, CD79B (including, without limitation, a mammalian or human homolog of any of these polypeptides). In some embodiments, the two or more ITAMs can differ from each other by one or more amino acid substitutions, deletions, or additions.

CAR-Linker Sequences

Any two neighboring domains of a chimeric antigen receptor can be separated by a linker sequence (e.g., any of the exemplary linker sequences described herein or known in the art).

In some embodiments, the linker sequence between the antigen-binding domain and the transmembrane domain can be 1 amino acid to about 250 amino acids, 1 amino acid to about 240 amino acids, 1 amino acid to about 230 amino acids, 1 amino acid to about 220 amino acids, 1 amino acid to about 210 amino acids, 1 amino acid to about 200 amino acids, 1 amino acid to about 190 amino acids, 1 amino acid to about 180 amino acids, 1 amino acid to about 170 amino acids, 1 amino acid to about 160 amino acids, 1 amino acid to about 150 amino acids, 1 amino acid to about 140 amino acids, 1 amino acid to about 130 amino acids, 1 amino acid to about 120 amino acids, 1 amino acid to about 110 amino acids, 1 amino acid to about 100 amino acids, 1 amino acid to about 95 amino acids, 1 amino acid to about 90 amino acids, 1 amino acid to about 85 amino acids, 1 amino acid to about 80 amino acids, 1 amino acid to about 75 amino acids, 1 amino acid to about 70 amino acids, 1 amino acid to about 65 amino acids, 1 amino acid to about 60 amino acids, 1 amino acid to about 55 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 20 amino acids, 1 amino acid to about 15 amino acids, 1 amino acid to about 10 amino acids, 1 amino acid to about 5 amino acids, about 5 amino acids to about 250 amino acids, about 5 amino acids to about 240 amino acids, about 5 amino acids to about 230 amino acids, about 5 amino acids to about 220 amino acids, about 5 amino acids to about 210 amino acids, about 5 amino acids to about 200 amino acids, about 5 amino acids to about 190 amino acids, about 5 amino acids to about 180 amino acids, about 5 amino acids to about 170 amino acids, about 5 amino acids to about 160 amino acids, about 5 amino acids to about 150 amino acids, about 5 amino acids to about 140 amino acids, about 5 amino acids to about 130 amino acids, about 5 amino acids to about 120 amino acids, about 5 amino acids to about 110 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 250 amino acids, about 10 amino acids to about 240 amino acids, about 10 amino acids to about 230 amino acids, about 10 amino acids to about 220 amino acids, about 10 amino acids to about 210 amino acids, about 10 amino acids to about 200 amino acids, about 10 amino acids to about 190 amino acids, about 10 amino acids to about 180 amino acids, about 10 amino acids to about 170 amino acids, about 10 amino acids to about 160 amino acids, about 10 amino acids to about 150 amino acids, about 10 amino acids to about 140 amino acids, about 10 amino acids to about 130 amino acids, about 10 amino acids to about 120 amino acids, about 10 amino acids to about 110 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 250 amino acids, about 15 amino acids to about 240 amino acids, about 15 amino acids to about 230 amino acids, about 15 amino acids to about 220 amino acids, about 15 amino acids to about 210 amino acids, about 15 amino acids to about 200 amino acids, about 15 amino acids to about 190 amino acids, about 15 amino acids to about 180 amino acids, about 15 amino acids to about 170 amino acids, about 15 amino acids to about 160 amino acids, about 15 amino acids to about 150 amino acids, about 15 amino acids to about 140 amino acids, about 15 amino acids to about 130 amino acids, about 15 amino acids to about 120 amino acids, about 15 amino acids to about 110 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 250 amino acids, about 20 amino acids to about 240 amino acids, about 20 amino acids to about 230 amino acids, about 20 amino acids to 220 amino acids, about 20 amino acids to about 210 amino acids, about 20 amino acids to about 200 amino acids, about 20 amino acids to about 190 amino acids, about 20 amino acids to about 180 amino acids, about 20 amino acids to about 170 amino acids, about 20 amino acids to about 160 amino acids, about 20 amino acids to about 150 amino acids, about 20 amino acids to about 140 amino acids, about 20 amino acids to about 130 amino acids, about 20 amino acids to about 120 amino acids, about 20 amino acids to about 110 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 250 amino acids, about 25 amino acids to about 240 amino acids, about 25 amino acids to about 230 amino acids, about 25 amino acids to about 220 amino acids, about 25 amino acids to about 210 amino acids, about 25 amino acids to about 200 amino acids, about 25 amino acids to about 190 amino acids, about 25 amino acids to about 180 amino acids, about 25 amino acids to about 170 amino acids, about 25 amino acids to about 160 amino acids, about 25 amino acids to about 150 amino acids, about 25 amino acids to about 140 amino acids, about 25 amino acids to about 130 amino acids, about 25 amino acids to about 120 amino acids, about 25 amino acids to about 110 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 250 amino acids, about 30 amino acids to about 240 amino acids, about 30 amino acids to about 230 amino acids, about 30 amino acids to about 220 amino acids, about 30 amino acids to about 210 amino acids, about 30 amino acids to about 200 amino acids, about 30 amino acids to about 190 amino acids, about 30 amino acids to about 180 amino acids, about 30 amino acids to about 170 amino acids, about 30 amino acids to about 160 amino acids, about 30 amino acids to about 150 amino acids, about 30 amino acids to about 140 amino acids, about 30 amino acids to about 130 amino acids, about 30 amino acids to about 120 amino acids, about 30 amino acids to about 110 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 250 amino acids, about 35 amino acids to about 240 amino acids, about 35 amino acids to about 230 amino acids, about 35 amino acids to about 220 amino acids, about 35 amino acids to about 210 amino acids, about 35 amino acids to about 200 amino acids, about 35 amino acids to about 190 amino acids, about 35 amino acids to about 180 amino acids, about 35 amino acids to about 170 amino acids, about 35 amino acids to about 160 amino acids, about 35 amino acids to about 150 amino acids, about 35 amino acids to about 140 amino acids, about 35 amino acids to about 130 amino acids, about 35 amino acids to about 120 amino acids, about 35 amino acids to about 110 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 250 amino acids, about 40 amino acids to about 240 amino acids, about 40 amino acids to about 230 amino acids, about 40 amino acids to about 220 amino acids, about 40 amino acids to about 210 amino acids, about 40 amino acids to about 200 amino acids, about 40 amino acids to about 190 amino acids, about 40 amino acids to about 180 amino acids, about 40 amino acids to about 170 amino acids, about 40 amino acids to about 160 amino acids, about 40 amino acids to about 150 amino acids, about 40 amino acids to about 140 amino acids, about 40 amino acids to about 130 amino acids, about 40 amino acids to about 120 amino acids, about 40 amino acids to about 110 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 250 amino acids, about 45 amino acids to about 240 amino acids, about 45 amino acids to about 230 amino acids, about 45 amino acids to about 220 amino acids, about 45 amino acids to about 210 amino acids, about 45 amino acids to about 200 amino acids, about 45 amino acids to about 190 amino acids, about 45 amino acids to about 180 amino acids, about 45 amino acids to about 170 amino acids, about 45 amino acids to about 160 amino acids, about 45 amino acids to about 150 amino acids, about 45 amino acids to about 140 amino acids, about 45 amino acids to about 130 amino acids, about 45 amino acids to about 120 amino acids, about 45 amino acids to about 110 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 250 amino acids, about 50 amino acids to about 240 amino acids, about 50 amino acids to about 230 amino acids, about 50 amino acids to about 220 amino acids, about 50 amino acids to about 210 amino acids, about 50 amino acids to about 200 amino acids, about 50 amino acids to about 190 amino acids, about 50 amino acids to about 180 amino acids, about 50 amino acids to about 170 amino acids, about 50 amino acids to about 160 amino acids, about 50 amino acids to about 150 amino acids, about 50 amino acids to about 140 amino acids, about 50 amino acids to about 130 amino acids, about 50 amino acids to about 120 amino acids, about 50 amino acids to about 110 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 250 amino acids, about 55 amino acids to about 240 amino acids, about 55 amino acids to about 230 amino acids, about 55 amino acids to about 220 amino acids, about 55 amino acids to about 210 amino acids, about 55 amino acids to about 200 amino acids, about 55 amino acids to about 190 amino acids, about 55 amino acids to about 180 amino acids, about 55 amino acids to about 170 amino acids, about 55 amino acids to about 160 amino acids, about 55 amino acids to about 150 amino acids, about 55 amino acids to about 140 amino acids, about 55 amino acids to about 130 amino acids, about 55 amino acids to about 120 amino acids, about 55 amino acids to about 110 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 250 amino acids, about 60 amino acids to about 240 amino acids, about 60 amino acids to about 230 amino acids, about 60 amino acids to about 220 amino acids, about 60 amino acids to about 210 amino acids, about 60 amino acids to about 200 amino acids, about 60 amino acids to about 190 amino acids, about 60 amino acids to about 180 amino acids, about 60 amino acids to about 170 amino acids, about 60 amino acids to about 160 amino acids, about 60 amino acids to about 150 amino acids, about 60 amino acids to about 140 amino acids, about 60 amino acids to about 130 amino acids, about 60 amino acids to about 120 amino acids, about 60 amino acids to about 110 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 250 amino acids, about 65 amino acids to about 240 amino acids, about 65 amino acids to about 230 amino acids, about 65 amino acids to about 220 amino acids, about 65 amino acids to about 210 amino acids, about 65 amino acids to about 200 amino acids, about 65 amino acids to about 190 amino acids, about 65 amino acids to about 180 amino acids, about 65 amino acids to about 170 amino acids, about 65 amino acids to about 160 amino acids, about 65 amino acids to about 150 amino acids, about 65 amino acids to about 140 amino acids, about 65 amino acids to about 130 amino acids, about 65 amino acids to about 120 amino acids, about 65 amino acids to about 110 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 250 amino acids, about 70 amino acids to about 240 amino acids, about 70 amino acids to about 230 amino acids, about 70 amino acids to about 220 amino acids, about 70 amino acids to about 210 amino acids, about 70 amino acids to about 200 amino acids, about 70 amino acids to about 190 amino acids, about 70 amino acids to about 180 amino acids, about 70 amino acids to about 170 amino acids, about 70 amino acids to about 160 amino acids, about 70 amino acids to about 150 amino acids, about 70 amino acids to about 140 amino acids, about 70 amino acids to about 130 amino acids, about 70 amino acids to about 120 amino acids, about 70 amino acids to about 110 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 250 amino acids, about 75 amino acids to about 240 amino acids, about 75 amino acids to about 230 amino acids, about 75 amino acids to about 220 amino acids, about 75 amino acids to about 210 amino acids, about 75 amino acids to about 200 amino acids, about 75 amino acids to about 190 amino acids, about 75 amino acids to about 180 amino acids, about 75 amino acids to about 170 amino acids, about 75 amino acids to about 160 amino acids, about 75 amino acids to about 150 amino acids, about 75 amino acids to about 140 amino acids, about 75 amino acids to about 130 amino acids, about 75 amino acids to about 120 amino acids, about 75 amino acids to about 110 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 250 amino acids, about 80 amino acids to about 240 amino acids, about 80 amino acids to about 230 amino acids, about 80 amino acids to about 220 amino acids, about 80 amino acids to about 210 amino acids, about 80 amino acids to about 200 amino acids, about 80 amino acids to about 190 amino acids, about 80 amino acids to about 180 amino acids, about 80 amino acids to about 170 amino acids, about 80 amino acids to about 160 amino acids, about 80 amino acids to about 150 amino acids, about 80 amino acids to about 140 amino acids, about 80 amino acids to about 130 amino acids, about 80 amino acids to about 120 amino acids, about 80 amino acids to about 110 amino acids, about 80 amino acids to about 100 amino acids, about 80 amino acids to about 95 amino acids, about 80 amino acids to about 90 amino acids, about 80 amino acids to about 85 amino acids, about 85 amino acids to about 250 amino acids, about 85 amino acids to about 240 amino acids, about 85 amino acids to about 230 amino acids, about 85 amino acids to about 220 amino acids, about 85 amino acids to about 210 amino acids, about 85 amino acids to about 200 amino acids, about 85 amino acids to about 190 amino acids, about 85 amino acids to about 180 amino acids, about 85 amino acids to about 170 amino acids, about 85 amino acids to about 160 amino acids, about 85 amino acids to about 150 amino acids, about 85 amino acids to about 140 amino acids, about 85 amino acids to about 130 amino acids, about 85 amino acids to about 120 amino acids, about 85 amino acids to about 110 amino acids, about 85 amino acids to about 100 amino acids, about 85 amino acids to about 95 amino acids, about 85 amino acids to about 90 amino acids, about 90 amino acids to about 250 amino acids, about 90 amino acids to about 240 amino acids, about 90 amino acids to about 230 amino acids, about 90 amino acids to about 220 amino acids, about 90 amino acids to about 210 amino acids, about 90 amino acids to about 200 amino acids, about 90 amino acids to about 190 amino acids, about 90 amino acids to about 180 amino acids, about 90 amino acids to about 170 amino acids, about 90 amino acids to about 160 amino acids, about 90 amino acids to about 150 amino acids, about 90 amino acids to about 140 amino acids, about 90 amino acids to about 130 amino acids, about 90 amino acids to about 120 amino acids, about 90 amino acids to about 110 amino acids, about 90 amino acids to about 100 amino acids, about 90 amino acids to about 95 amino acids, about 95 amino acids to about 250 amino acids, about 95 amino acids to about 240 amino acids, about 95 amino acids to about 230 amino acids, about 95 amino acids to about 220 amino acids, about 95 amino acids to about 210 amino acids, about 95 amino acids to about 200 amino acids, about 95 amino acids to about 190 amino acids, about 95 amino acids to about 180 amino acids, about 95 amino acids to about 170 amino acids, about 95 amino acids to about 160 amino acids, about 95 amino acids to about 150 amino acids, about 95 amino acids to about 140 amino acids, about 95 amino acids to about 130 amino acids, about 95 amino acids to about 120 amino acids, about 95 amino acids to about 110 amino acids, about 95 amino acids to about 100 amino acids, about 100 amino acids to about 250 amino acids, about 100 amino acids to about 240 amino acids, about 100 amino acids to about 230 amino acids, about 100 amino acids to about 220 amino acids, about 100 amino acids to about 210 amino acids, about 100 amino acids to about 200 amino acids, about 100 amino acids to about 190 amino acids, about 100 amino acids to about 180 amino acids, about 100 amino acids to about 170 amino acids, about 100 amino acids to about 160 amino acids, about 100 amino acids to about 150 amino acids, about 100 amino acids to about 140 amino acids, about 100 amino acids to about 130 amino acids, about 100 amino acids to about 120 amino acids, about 100 amino acids to about 110 amino acids, about 120 amino acids to about 250 amino acids, about 120 amino acids to about 240 amino acids, about 120 amino acids to about 230 amino acids, about 120 amino acids to about 220 amino acids, about 120 amino acids to about 210 amino acids, about 120 amino acids to about 200 amino acids, about 120 amino acids to about 190 amino acids, about 120 amino acids to about 180 amino acids, about 120 amino acids to about 170 amino acids, about 120 amino acids to about 160 amino acids, about 120 amino acids to about 150 amino acids, about 120 amino acids to about 140 amino acids, about 120 amino acids to about 130 amino acids, about 130 amino acids to about 250 amino acids, about 130 amino acids to about 240 amino acids, about 130 amino acids to about 230 amino acids, about 130 amino acids to about 220 amino acids, about 130 amino acids to about 210 amino acids, about 130 amino acids to about 200 amino acids, about 130 amino acids to about 190 amino acids, about 130 amino acids to about 180 amino acids, about 130 amino acids to about 170 amino acids, about 130 amino acids to about 160 amino acids, about 130 amino acids to about 150 amino acids, about 130 amino acids to about 140 amino acids, about 140 amino acids to about 250 amino acids, about 140 amino acids to about 240 amino acids, about 140 amino acids to about 230 amino acids, about 140 amino acids to about 220 amino acids, about 140 amino acids to about 210 amino acids, about 140 amino acids to about 200 amino acids, about 140 amino acids to about 190 amino acids, about 140 amino acids to about 180 amino acids, about 140 amino acids to about 170 amino acids, about 140 amino acids to about 160 amino acids, about 140 amino acids to about 150 amino acids, about 150 amino acids to about 250 amino acids, about 150 amino acids to about 240 amino acids, about 150 amino acids to about 230 amino acids, about 150 amino acids to about 220 amino acids, about 150 amino acids to about 210 amino acids, about 150 amino acids to about 200 amino acids, about 150 amino acids to about 190 amino acids, about 150 amino acids to about 180 amino acids, about 150 amino acids to about 170 amino acids, about 150 amino acids to about 160 amino acids, about 160 amino acids to about 250 amino acids, about 160 amino acids to about 240 amino acids, about 160 amino acids to about 230 amino acids, about 160 amino acids to about 220 amino acids, about 160 amino acids to about 210 amino acids, about 160 amino acids to about 200 amino acids, about 160 amino acids to about 190 amino acids, about 160 amino acids to about 180 amino acids, about 160 amino acids to about 170 amino acids, about 170 amino acids to about 250 amino acids, about 170 amino acids to about 240 amino acids, about 170 amino acids to about 230 amino acids, about 170 amino acids to about 220 amino acids, about 170 amino acids to about 210 amino acids, about 170 amino acids to about 200 amino acids, about 170 amino acids to about 190 amino acids, about 170 amino acids to about 180 amino acids, about 180 amino acids to about 250 amino acids, about 180 amino acids to about 240 amino acids, about 180 amino acids to about 230 amino acids, about 180 amino acids to about 220 amino acids, about 180 amino acids to about 210 amino acids, about 180 amino acids to about 200 amino acids, about 180 amino acids to about 190 amino acids, about 190 amino acids to about 250 amino acids, about 190 amino acids to about 240 amino acids, about 190 amino acids to about 230 amino acids, about 190 amino acids to about 220 amino acids, about 190 amino acids to about 210 amino acids, about 190 amino acids to about 200 amino acids, about 200 amino acids to about 250 amino acids, about 200 amino acids to about 240 amino acids, about 200 amino acids to about 230 amino acids, about 200 amino acids to 220 amino acids, about 200 amino acids to about 210 amino acids, about 210 amino acids to about 250 amino acids, about 210 amino acids to about 240 amino acids, about 210 amino acids to about 230 amino acids, about 210 amino acids to about 220 amino acids, about 220 amino acids to about 250 amino acids, about 220 amino acids to about 240 amino acids, about 220 amino acids to about 230 amino acids, about 230 amino acids to about 250 amino acids, about 230 amino acids to about 240 amino acids, or about 240 amino acids to about 250 amino acids.

In some embodiments, a linker sequence between the antigen-binding domain and the transmembrane domain can be or can include one or more of an IgG1, IgG2, IgG3, or IgG4 CH1, CH2, and CH3 domain. In some embodiments, the linker between the antigen-binding domain and the transmembrane domain can be or can include CH2-CH3 human IgG1 domains. In some embodiments, the CH2-CH3 human IgG1 domains have a sequence of:

```
                                              (SEQ ID NO: 62)
AEPKSPDKTHTCPPCPAPPVAGPSVFLFPPKPKDTLMIARTPEVTCWVDVS

HEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQG

NVFSCSVMHEALHNHYTQKSLSLSPGKKD.
```

In some embodiments, the linker sequence between the antigen-binding domain and the transmembrane domain can be or include a portion of the human CD8 extracellular sequence that is proximal to the human CD8 transmembrane domain. For example, the linker sequence between the antigen-binding domain and the transmembrane domain can be or include human CD8 sequence of TTTPAPRPPTPAPTIASQPLSLRPEACRPAAGGAVHTRGLDFACDI (SEQ ID NO: 63).

In some embodiments, the linker sequence between the antigen-binding domain and the transmembrane domain can be or include a human IgG1 hinge sequence. In some embodiments, the human IgG1 hinge sequence is AEPKSPDKTHTCPPCPKDPK (SEQ ID NO: 64).

In some embodiments, a linker sequence (e.g., any of the linker sequences described herein or known in the art) can be present between the transmembrane domain and a costimulatory domain. In some embodiments, a linker sequence (e.g., any of the linker sequences described herein or known in the art) can be present between the costimulatory domain and the ITAM.

Nucleic Acids

Also provided herein are nucleic acids that encode any of chimeric transmembrane proteins described herein.

Vectors

Provided herein are vectors that include any of the nucleic acids that encode any of the chimeric transmembrane proteins provided herein. A "vector" according to the present disclosure is a polynucleotide capable of inducing the expression of a recombinant protein (e.g., a chimeric transmembrane protein and/or a chimeric antigen receptor) in a mammalian cell. A vector provided herein can be, e.g., in circular or linearized form. Non-limiting examples of vectors include plasmids, SV40 vectors, adenoviral viral vectors, and adeno-associated virus (AAV) vectors. Non-limiting examples of vectors include lentiviral vectors or retroviral vectors, e.g., gamma-retroviral vectors. See, e.g., Carlens et al., *Exp. Hematol.* 28(10:1137-1146, 2000; Park et al., *Trends Biotechnol.* 29(11):550-557, 2011; and Alonso-Camino et al., *Mol. Ther. Nucleic Acids* 2:e93, 2013. Non-limiting examples of retroviral vectors include those derived from Moloney murine leukemia virus, myeloproliferative sarcoma virus, murine embryonic stem cell virus, murine stem cell virus, spleen focus forming virus, or adeno-associated virus. Non-limiting examples of retroviral vectors are described in, e.g., U.S. Pat. Nos. 5,219,740 and 6,207,453; Miller et al., *BioTechniques* 7:980-990, 1989; *Miller, Human Gene Therapy* 1:5-14, 1990; Scarpa et al., *Virology* 180:849-852, 1991; Burns et al., *Proc. Natl. Acad. Sci. U.S.A.* 90:8033-8037, 1993; and Boris-Lawrie et al., *Cur. Opin. Genet. Develop.* 3:102-109, 1993. Exemplary lentiviral vectors are described in, e.g., Wang et al., *J. Immunother.* 35(9):689-701, 2003; Cooper et al., *Blood* 101:1637-1644, 2003; Verhoeyen et al., *Methods Mol. Biol.* 506:97-114, 2009; and Cavalieri et al., *Blood* 102(2):497-505, 2003.

Exemplary vectors, in which any of the nucleic acids provided herein can be inserted, are described in, e.g., Ausubel et al., Eds. "Current Protocols in Molecular Biology" Current Protocols, 1993; and Sambrook et al., Eds. "Molecular Cloning: A Laboratory Manual," 2nd ed., Cold Spring Harbor Press, 1989.

In some embodiments, the vectors further include a promoter sequence and/or enhancer sequence operably linked to any of the nucleic acids described herein. Non-limiting examples of promoters include promoters from human cytomegalovirus (CMV), mouse phosphoglycerate to kinase 1, polyoma adenovirus, thyroid stimulating hormone α, vimentin, simian virus 40 (SV40), tumor necrosis factor, β-globin, α-fetoprotein, γ-globin, β-interferon, γ-glutamyl transferase, human ubiquitin C (UBC), mouse mammary tumor virus (MMTV), Rous sarcoma virus, glyceraldehyde-3-phosphate dehydrogenase, β-actin, metallothionein II (MT II), amylase, human EF1α, cathepsin, MI muscarinic receptor, retroviral LTR (e.g. human T-cell leukemia virus HTLV), AAV ITR, interleukin-2, collagenase, platelet-derived growth factor, adenovirus E2, stromelysin, murine MX, rat insulin, glucose regulated protein 78, human immunodeficiency virus, glucose regulated protein 94, α-2-macroglobulin, MHC class I, HSP70, proliferin, immunoglobulin light chain, T-cell receptor, HLA DQα, HLA DQβ, interleukin-2 receptor, MHC class II, prealbumin (transthyretin), elastase I, albumin, c-fos, neural cell adhesion molecule (NCAM), H2B histone, rat growth hormone, human serum amyloid (SAA), muscle creatinine kinase, troponin I (TN I), and Gibbon Ape Leukemia Virus (GALV). In some embodiments, the promoter may be an inducible promoter or a constitutive promoter. Additional examples of promoters are known in the art.

In some examples, the vectors provided herein further include a poly(A) sequence, which is operably linked and positioned 3' to the sequence encoding the chimeric transmembrane protein or a chimeric antigen receptor. Non-limiting examples of a poly(A) sequence include those derived from bovine growth hormone (Woychik et al., *Proc. Natl. Acad. Sci. U.S.A.* 81(13): 3944-3948, 1984, and U.S. Pat. No. 5,122,458), mouse-β-globin, mouse-α-globin (Orkin et al., *EMBO J.* 4(2): 453-456, 1985), human collagen, polyoma virus (Batt et al., *Mol. Cell Biol.* 15(9):4783-4790, 1995), the Herpes simplex virus thymidine kinase gene (HSV TK), IgG heavy chain gene polyadenylation signal (U.S. Patent Application Publication No. 2006/0040354), human growth hormone (hGH) (Szymanski et al., *Mol. Therapy* 15(7):1340-1347, 2007), SV40 poly(A) site, e.g., SV40 late and early poly(A) site (Schek et al., *Mol. Cell Biol.* 12(12):5386-5393, 1992). In some embodiments, the poly(A) sequence includes a highly conserved upstream element (AATAAA). The this AATAAA sequence can, e.g., be substituted with other hexanucleotide sequences with homology to AATAAA which are capable of signaling polyadenylation, including, e.g., ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, and AATAAG. See, e.g., WO 06012414 A2).

A poly(A) sequence can, e.g., be a synthetic polyadenylation site. See, e.g., Levitt el al, *Genes Dev.* 3(7): 1019-1025, 1989). In some examples, a poly(A) sequence can be the polyadenylation signal of soluble neuropilin-1: AAATAAAATACGAAATG (SEQ ID NO: 88). Additional examples of poly(A) sequences are known in the art. Additional examples and aspects of vectors are also known in the art.

In some embodiments of any of the vectors described herein, the vector can further include a sequence encoding a chimeric antigen receptor. In some embodiments, the chimeric antigen receptor can bind specifically to a tumor antigen (e.g., a tumor antigen selected from the group of glypican-3, BCMA, MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin). In some embodiments, the chimeric antigen receptor comprises one or more co-stimulatory signaling domains selected from the group of 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, B7-H3, DAP-10, and DAP-12. In some examples of any of the vectors described herein, the vector is a lentiviral or an adenoviral vector.

Also provided herein are sets of vectors that include a first vector that includes a sequence that encodes any of the chimeric transmembrane proteins described herein (e.g., any of the vectors that includes a sequence that encodes any of the chimeric transmembrane proteins described herein), and a second vector that includes a sequence that encodes a chimeric antigen receptor (e.g., any of the chimeric antigen receptors described herein). In some embodiments, one or both of the first vector and the second vector is a lentiviral or an adenoviral vector. In some embodiments, the second vector further includes a promoter sequence and/or an enhancer sequence that is operably linked to the sequence encoding the chimeric antigen receptor. In some embodiments, the second vector further includes a poly(A) sequence operably linked to the sequence encoding the chimeric antigen receptor.

Methods of Introducing a Nucleic Acid or Vectors into a Mammalian Cell

A variety of different methods known in the art can be used to introduce any of the nucleic acids and vectors disclosed herein into a mammalian cell (e.g., any of the mammalian cells described herein, e.g., any of the T cells (e.g., human T cells) described herein). Non-limiting examples of methods that can be used to introduce a nucleic acid or vector into a mammalian cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection. Additional methods of introducing a nucleic acid or vector into a mammalian cell are known in the art.

Mammalian Cells

Also provided herein are mammalian cells that include any of the nucleic acids or vectors described herein. Also provided herein are mammalian cells that include any of the sets of vectors described herein.

In some embodiments, the mammalian cell is previously obtained from a subject (e.g., a human subject, e.g., a human subject identified or diagnosed as having a cancer) or is a daughter cell of a mammalian cell that was previously obtained from a subject (e.g., a human subject, e.g., a human subject identified or diagnosed as having a cancer). In some embodiments, the mammalian cell is an immune cell. In some embodiments, the mammalian cell is a human cell.

Non-limiting examples of immune cells include a T cell (e.g., a human T cell). Non limiting examples of T cells (e.g., human T cells) include, e.g., an immature thymocyte, a peripheral blood lymphocyte, a helper T cell, a naïve T cell, a pluripotent TH cell precursor, a lymphoid progenitor cell, a $T_{reg}$ cell, a memory T cell, a $T_H17$ cell, a $T_H22$ cell, a $T_H9$ cell, a $T_H2$ cell, a $T_H1$ cell, a $T_H3$ cell, γδ T cell, an αβ T cell, a regulatory T cell (Treg cell), and a tumor-infiltrating T cell. Additional examples of a T cell (e.g., a human T cell) include a $CD8^+$ T cell, a $CD4^+$ T cell, a memory T cell, a Treg cell, natural killer cell, B cell, and a monocyte. Additional examples of mammalian cells include a mast cell, a macrophage, a neutrophil, a dendritic cell, a basophil, an eosinophil, and a natural killer cell.

Compositions and Kits

Also provided herein are compositions (e.g., pharmaceutical compositions) that include any of the nucleic acids, vectors, sets of nucleic acids, sets of vectors, or mammalian cells described herein. For example, provided herein is a composition that includes any of the nucleic acids or sets of nucleic acids described herein, or any of the vectors or sets of vectors provided herein, and a pharmaceutically acceptable solvent or carrier.

In some embodiments, a composition can be any of the mammalian cells described herein (e.g., any of the mammalian cells described herein previously obtained from a subject, e.g., a subject identified or diagnosed as having a cancer) comprising a nucleic acid encoding any of the chimeric transmembrane proteins and/or any of the chimeric antigen receptors described herein. In a composition including any of the mammalian cells described herein, the composition can further include a cell culture medium or a pharmaceutically acceptable buffer (e.g., phosphate-buffered saline). A composition that includes any of the mammalian cells described herein can be formulated for intravenous or intraarterial administration.

Also provided are kits that include one or more of any of the compositions (e.g., pharmaceutical compositions) described herein. In some embodiments, a kit can further include instructions for performing any of the methods described herein.

Methods of Treating a Cancer in a Subject

Also provided herein are methods of treating a cancer in a subject (e.g., a human, a mouse, a rabbit, a rat, a horse, a dog, a monkey, or an ape) that include administering a therapeutically effective amount of any of the mammalian cells including a nucleic acid encoding any of the chimeric transmembrane proteins described herein (and optionally a nucleic acid including any of the chimeric antigen receptors described herein). In some examples of these methods, the mammalian cell is a T cell (e.g., a CD8+ T cell, a CD4+ T cell, a memory T cell, a Treg cell, and a natural killer T cell). In some examples, the mammalian cell (e.g., any of the mammalian cells described herein) is a mammalian cell previously obtained from a subject (e.g., a subject that has been identified or diagnosed as having a cancer, e.g., any of the cancers described herein). Some embodiments of these methods further include obtaining the mammalian cell from the subject.

Some embodiments of these methods further include introducing a nucleic acid encoding the single-chain chimeric antigen receptor described herein or the multi-chain chimeric antigen receptor described into a mammalian cell (e.g., any of the mammalian cells described herein or known in the art) to generate the mammalian cell that is administered to the subject.

Non-limiting examples of cancer that can be treated using any of the methods provided herein include: hepatocellular carcinoma, acute lymphoblastic leukemia, acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastric cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, gastric cancer, testicular cancer, throat cancer, thyroid cancer, urethral cancer, uterine cancer, vaginal cancer, and vulvar cancer.

In some embodiments of any of these methods, the methods result in a decrease in the tumor burden (e.g., a decrease in tumor mass and/or volume of a solid tumor) in a subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35%

(inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the tumor burden in a subject (e.g., as compared to the tumor burden in the subject prior to treatment).

In some embodiments, the methods result in a decrease in the rate of progression of a cancer in the subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the rate of progression of a cancer in a subject (e.g., as compared to the rate of progression of a cancer in the subject prior to treatment or in a control subject or a control population of subjects having the same cancer and administered no treatment or a different treatment).

In some embodiments of any of these methods, the methods result in an increase in the time of survival of a cancer in a subject. For example, any of the methods described herein can result in an about 1% to about 800% (e.g., about 1% to about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, about 10%, or about 5% (inclusive); about 5% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, or about 10% (inclusive); about 10% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, or about 20% (inclusive); about 20% to about 800%, about 750%, about 700%, about 650%, about 600%, about 550%, about 500%, about 450%, about 400%, about 350%, about 300%, about 250%, about 200%, about 150%, about 100%, about 80%, about 60%, or about 40% (inclusive); about 40% to about 800%, about 750%, about 700%, about 650%, about 600%, about 550%, about 500%, about 450%, about 400%, about 350%, about 300%, about 250%, about 200%, about 150%, about 100%, about 80%, or about 60% (inclusive); about 60% to about 800%, about 750%, about 700%, about 650%, about 600%, about 550%, about 500%, about 450%, about 400%, about 350%, about 300%, about 250%, about 200%, about 150%, about 100%, about 80% (inclusive); about 80% to about 800%, about 750%, about 700%, about 650%, about 600%, about 550%, about 500%, about 450%, about 400%, about 350%, about 300%, about 250%, about 200%, about 150%, or about 100% (inclusive); about 100% to about 800%, about 750%, about 700%, about 650%, about 600%, about 550%, about 500%, about 450%, about 400%, about 350%, about 300%, about 250%, about 200%, or about 150% (inclusive); about 150% to about 800%, about 750%, about 700%, about 650%, about 600%, about 550%, about 500%, about 450%, about 400%, about 350%, about 300%, about 250%, or about 200% (inclusive); about 200% to about 800%, about 750%, about 700%, about 650%, about 600%, about 550%, about 500%, about 450%, about 400%, about 350%, about 300%, or about 250% (inclusive); about 250% to about 800%, about 750%, about 700%, about 650%, about 600%, about 550%, about 500%, about 450%, about 400%, about 350%, or about 300% (inclusive); about 300% to about 800%, about 750%, about 700%, about 650%, about 600%, about 550%, about 500%, about 450%, about 400%, or about 350% (inclusive); about 350% to about 800%, about 750%, about 700%, about 650%, about 600%, about 550%, about 500%, about 450%, or about 400% (inclusive); about 400% to about 800%, about 750%, about 700%, about 650%, about 600%, about 550%, about 500%, or about 450% (inclusive); about 450% to about 800%, about 750%, about 700%, about 650%, about 600%, about 550%, or about 500% (inclusive); about 500% to about 800%, about 750%, about 700%, about 650%, about 600%, or about 550% (inclusive); about 550% to about 800%, about 750%, about 700%, about 650%, or about 600% (inclusive); about 600% to about 800%, about 750%, about 700%, or about 650% (inclusive); about 650% to about 800%, about 750%, or about 700% (inclusive); about 700% to about 800% or about 750% (inclusive); or about 750% to about 800% (inclusive)) increase in the time of survival of a cancer in a subject (e.g., as compared to the time of survival for a control subject or a population of control subjects having the same cancer and receiving no treatment or a different treatment).

Also provided herein are methods of inducing cell death in a cancer cell in a subject in need thereof that include administering to the subject a therapeutically effective amount of any of the mammalian cells described herein.

Also provided herein are methods of decreasing the risk of developing a metastasis or an additional metastasis in a subject having a cancer that include administering to the subject a therapeutically effective amount of any of the mammalian cells described herein. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) decrease in the risk of developing a metastasis or an additional metastasis in the subject (e.g., as compared to the risk of developing a metastasis or an additional metastasis in a control subject or a control population of subjects having the same cancer and administered no treatment or a different treatment).

EXAMPLES

The invention is further described in the following examples, which do not limit the scope of the invention described in the claims.

Figure 2:
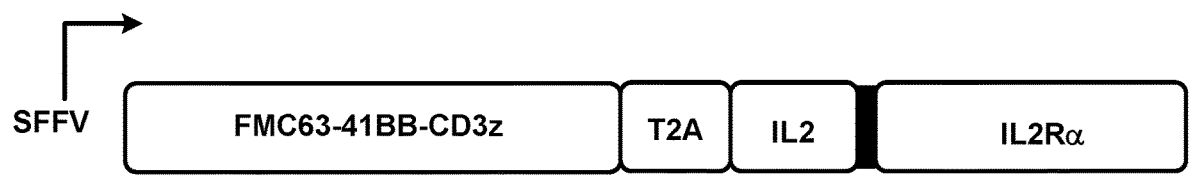
FIG. 2 is a schematic drawing of a vector encoding an exemplary chimeric antigen receptor used to transduce a T cell. The vector contains a SFFV promoter; a sequence encoding an exemplary chimeric antigen receptor comprising a FMC63 antigen-binding domain (anti-CD19), a 4-1BB costimulatory signaling domain, and a CD3ζ ITAM; and a sequence encoding an exemplary chimeric transmembrane shown in FIG. 1.

Example 1. Construction of a Vector Containing a Chimeric Transmembrane Protein and a CAR The vector shown in FIG. 2 was generated. The amino acid and nucleic acid sequences present in the vector in FIG. 2 are provided below.

mbIL2 (Chimeric Transmembrane Protein of SEQ ID NO: 7) (CSF2RA signal peptide underlined, poly-His tag in bold)

<u>MLLLVTSLLLCELPHPAFLLIP</u>HHHHHHAPTSSSTKKTQLQLEHLLLDLQM
ILNGINNYKNPKLTRMLTFKFYMPKKATELKHLQCLEEELKPLEEVNLAQ
SKNFHLRPRDLISNINVIVLELKGSETTFMCEYADETATIVEFLNRWITFC
QSllSTLTSGGGSGGGGSGGGGSGGGGSGGGSLQELCDDDPPEIPHATFKA
MAYKEGTMLNCECKRGFRRIKSGSLYMLCTGNSSHSSWDNQCQCTSSATRN
TTKQVTPQPEEQKERKTTEMQSPMQPVDQASLPGHCREPPPWENEATERIY
HFVVGQMVYYQCVQGYRALHRGPAESVCKMTHGKTRWTQPQLICTGEMETS
QFPGEEKPQASPEGRPESETSCLVTTTDFQIQTEMAATMETSIFTTEYQVA
VAGCVFLLISVLLLSGLTWQRRQRKSRRTI

Nucleic Acid Sequence Encoding mbIL2
(SEQ ID NO: 65)
ATGCTCCTGCTCGTGACTTCACTTCTTCTCTGTGAACTCCCACACCCCGCG
TTTTTGCTTATCCCTcatcatcaccatcaccacGCACCTACTTCAAGTTCT
ACAAAGAAAACACAGCTACAACTGGAGCATTTACTTCTGGATTTACAGATG
ATTTTGAATGGAATTAATAATTACAAGAATCCCAAACTCACCAGGATGCTC
ACATTTAAGTTTTACATGCCCAAGAAGGCCACAGAACTGAAACATCTTCAG
TGTCTAGAAGAAGAACTCAAACCTCTGGAGGAAGTGCTAAATTTAGCTCAA
AGCAAAAACTTTCACTTAAGACCCAGGGACTTAATCAGCAATATCAACGTA
ATAGTTCTGGAACTAAAGGGATCTGAAACAACATTCATGTGTGAATATGCT
GATGAGACAGCAACCATTGTAGAATTTCTGAACAGATGGATTACCTTTTGT
CAAAGCATCATCTCAACACTGACTTCTGGAGGAGGTAGTGGAGGCGGCGGG
AGCGGTGGGGAGGGTCTGGGGGTGGGGGATCCGGAGGTGGGTCACTGCAG
GAGCTCTGTGACGATGACCCGCCAGAGATCCCACACGCCACATTCAAAGCC
ATGGCCTACAAGGAAGGAACCATGTTGAACTGTGAATGCAAGAGAGGTTTC
CGCAGAATAAAAAGCGGGTCACTCTATATGCTCTGTACAGGAAACTCTAGC
CACTCGTCCTGGGACAACCAATGTCAATGCACAAGCTCTGCCACTCGGAAC
ACAACGAAACAAGTGACACCTCAACCTGAAGAACAGAAAGAAAGGAAAACC
ACAGAAATGCAAAGTCCAATGCAGCCAGTGGACCAAGCGAGCCTTCCAGGT
CACTGCAGGGAACCTCCACCATGGGAAAATGAAGCCACAGAGAGAATTTAT
CATTTCGTGGTGGGCAGATGGTTTATTATCAGTGCGTCCAGGGATACAGG
GCTCTACACAGAGGTCCTGCTGAGAGCGTCTGCAAAATGACCCACGGGAAG
ACAAGGTGGACCCAGCCCCAGCTCATATGCACAGGTGAAATGGAGACCAGT
CAGTTTCCAGGTGAAGAGAAGCCTCAGGCAAGCCCCGAAGGCCGTCCTGAG
AGTGAGACTTCCTGCCTCGTCACAACAACAGATTTTCAAATACAGACAGAA
ATGGCTGCAACCATGGAGACGTCCATATTTACAACAGAGTACCAGGTAGCA
GTGGCCGGCTGTGTTTTCCTGCTGATCAGCGTCCTCCTCCTGAGTGGGCTC
ACCTGGCAGCGGAGACAGAGGAAGAGTAGAAGAACAATCTG AA Sequence for T2A and Furin Cleavage site
(SEQ ID NO: 66)
RKRRGKPIPNPLLGLDSTSGSGEGRGSLLTCGDVEENPGPG Nucleic Acid Sequence for T2A and Furin Cleavage site
(SEQ ID NO: 67)
cggaagagaagaggcaagcccatccccaacccactgctgggcctggatagc
acctccggctcaggagagggcagaggctctctgctgacctgcggcgacgtg
gaagagaacccgggcccgggc FMC63-41BB-CD3z CAR Protein Sequence
(SEQ ID NO: 68)
MLLLVTSLLLCELPHPAFLLIPEQKLISEEDLDIQMTQTTSSLSASLGDRV
TISCRASQDISKYLNWYQQKPDGTVKLLIYHTSRLHSGVPSRFSGSGSGTD
YSLTISNLEQEDIATYFCQQGNTLPYTFGGGTKLEITGGGGSGGGGSGGGG
SEVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYYY
GGSYAMDYWGQGTSVTVSSGTTTPAPRPPTPAPTIASQPLSLRPEACRPA
AGGAVHTRGLDFACDIYIWAPLAGTCGVLLLSLVITLYCKRGRKKLLYIFK
QPFMRPVQTTQEEDGCSCRFPEEEEGGCELRVKFSRSADAPAYQQGQNQLY
NELNLGRREEYDVLDKRRGRDPEMGGKPRRKNPQEGLYNELQKDKMAEAYS
EIGMKGERRRGKGHDGLYQGLSTATKDTYDALHMQALPPR FMC63-41BB-CD3z CAR Nucleic Acid Sequence
(SEQ ID NO: 69)
ATGCTTCTCCTGGTGACAAGCCTTCTGCTCTGTGAGTTACCACACCCAGCA
TTCCTCCTGATTCCTGAACAGAAGCTGATAAGTGAGGAGGACTTGGACATC
CAGATGACCCAGACCACCAGCAGCCTGAGCGCCAGCCTGGGCGATAGAGTG
ACCATCAGCTGCAGAGCCAGCCAGGACATCAGCAAGTACCTGAACTGGTAT
CAGCAGAAACCCGACGGCACCGTGAAGCTGCTGATCTACCACACCAGCAGA
CTGCACAGCGGCGTGCCCAGCAGATTTTCTGGCAGCGGCTCCGGCACCGAC
TACAGCCTGACCATCTCCAACCTGGAACAGGAAGATATCGCTACCTACTTC
TGTCAGCAAGGCAACACCCTGCCCTACACCTTCGGCGGAGGCACCAAGCTG
GAAATCACAGGCGGCGGAGGATCTGGCGGAGGCGGAAGTGGCGGAGGGGGA
TCTGAAGTGAAACTGCAGGAAAGCGGCCCTGGCCTGGTGGCCCCATCTCAG
TCTCTGAGCGTGACCTGTACCGTGTCCGGCGTGTCCCTGCCTGACTATGGC
GTGTCCTGGATCAGACAGCCCCCCAGAAAGGGCCTGGAATGGCTGGGAGTG
ATCTGGGGCAGCGAGACAACCTACTACAACAGCGCCCTGAAGTCCCGGCTG
ACCATCATCAAGGACAACTCCAAGAGCCAGGTGTTCCTGAAGATGAACAGC
CTGCAGACCGACGACACCGCCATCTACTACTGCGCCAAGCACTACTACTAC
GGCGGCAGCTACGCCATGGACTACTGGGGCCAGGGCACAAGCGTGACCGTG
TCTAGCGGATCCACCACGACGCCAGCGCCGCGACCACCAACACCGGCGCCC
ACCATCGCGTCGCAGCCCCTGTCCCTGCGCCCAGAGGCGTGCCGGCCAGCG
GCGGGGGGCGCAGTGCACACGAGGGGGCTGGACTTCGCCTGTGATATCTAC
ATCTGGGCGCCCTTGGCCGGGACTTGTGGGGTCCTTCTCCTGTCACTGGTT
ATCACCCTTTACTGCAAACGGGGCAGAAAGAAACTCCTGTATATATTCAAA
CAACCATTTATGAGACCAGTACAAACTACTCAAGAGGAAGATGGCTGTAGC
TGCCGATTTCCAGAAGAAGAAGAAGGAGGATGTGAACTGAGAGTGAAGTTC
AGCAGGAGCGCAGACGCCCCCGCGTACCAGCAGGGCCAGAACCAGCTCTAT

```
AACGAGCTCAATCTAGGACGAAGAGAGGAGTACGATGTTTTGGACAAGAGA

CGTGGCCGGGACCCTGAGATGGGGGGAAAGCCGAGAAGGAAGAACCCTCAG

GAAGGCCTGTACAATGAACTGCAGAAAGATAAGATGGCGGAGGCCTACAGT

GAGATTGGGATGAAAGGCGAGCGCCGGAGGGGCAAGGGGCACGATGGCCTT

TACCAGGGTCTCAGTACAGCCACCAAGGACACCTACGACGCCCTTCACATG

CAGGCCCTGCCCCCTCGC
```

CAR Signal Peptide- Amino Acid Sequence
(SEQ ID NO: 70)
MLLLVTSLLLCELPHPAFLLIP

CAR Signal Peptide- Nucleic Acid Sequence
(SEQ ID NO: 71)
```
ATGCTTCTCCTGGTGACAAGCCTTCTGCTCTGTGAGTTACCACACCCAGCA

TTCCTCCTGATTCCT
```

CAR Myc Tag- Amino Acid Sequences
(SEQ ID NO: 72)
EQKLISEEDL

CAR Myc Tag- Nucleic Acid Sequences
(SEQ ID NO: 73)
GAACAGAAGCTGATAAGTGAGGAGGACTTG FMC63 scFv- Amino Acid Sequence
(SEQ ID NO: 74)
DIQMTQTTSSLSASLGDRVTISCRASQDISKYLNWYQQKPDGTVKLLIYHT
SRLHSGVPSRFSGSGSGTDYSLTISNLEQEDIATYFCQQGNTLPYTFGGGT
KLEITGGGGSGGGGSGGGGSEVKLQESGPGLVAPSQSLSVTCTVSGVSLPD
YGVSWIRQPPRKGLEWLGVIWGSETTYYNSALKSRLTIIKDNSKSQVFLKM
NSLQTDDTAIYYCAKHYYYGGSYAMDYWGQGTSVTVSS FMC63 scFv- Nucleic Acid Sequence
(SEQ ID NO: 75)
```
GACATCCAGATGACCCAGACCACCAGCAGCCTGAGCGCCAGCCTGGGCGAT

AGAGTGACCATCAGCTGCAGAGCCAGCCAGGACATCAGCAAGTACCTGAAC

TGGTATCAGCAGAAACCCGACGGCACCGTGAAGCTGCTGATCTACCACACC

AGCAGACTGCACAGCGGCGTGCCCAGCAGATTTTCTGGCAGCGGCTCCGGC

ACCGACTACAGCCTGACCATCTCCAACCTGGAACAGGAAGATATCGCTACC

TACTTCTGTCAGCAAGGCAACACCCTGCCCTACACCTTCGGCGGAGGCACC

AAGCTGGAAATCACAGGCGGCGGAGGATCTGGCGGAGGCGGAAGTGGCGGA

GGGGGATCTGAAGTGAAACTGCAGGAAAGCGGCCCTGGCCTGGTGGCCCCA

TCTCAGTCTCTGAGCGTGACCTGTACCGTGTCCGGCGTGTCCCTGCCTGAC

TATGGCGTGTCCTGGATCAGACAGCCCCCAGAAAGGGCCTGGAATGGCTG

GGAGTGATCTGGGGCAGCGAGACAACCTACTACAACAGCGCCCTGAAGTCC

CGGCTGACCATCATCAAGGACAACTCCAAGAGCCAGGTGTTCCTGAAGATG

AACAGCCTGCAGACCGACGACACCGCCATCTACTACTGCGCCAAGCACTAC

TACTACGGCGGCAGCTACGCCATGGACTACTGGGGCCAGGGCACAAGCGTG

ACCGTGTCTAGC
```

CAR CD8 Hinge and Transmembrane Domain- Amino Acid Sequence
(SEQ ID NO: 76)
GSTTTPAPRPPTPAPTIASQPLSLRPEACRPAAGGAVHTRGLDFACDIYIW
APLAGTCGVLLLSLVITLYC CAR CD8 Hinge and Transmembrane Domain- Nucleic Acid Sequence
(SEQ ID NO: 77)
```
GGATCCACCACGACGCCAGCGCCGCGACCACCAACACCGGCGCCCACCATC

GCGTCGCAGCCCCTGTCCCTGCGCCCAGAGGCGTGCCGGCCAGCGGCGGGG

GGCGCAGTGCACACGAGGGGGCTGGACTTCGCCTGTGATATCTACATCTGG

GCGCCCTTGGCCGGGACTTGTGGGGTCCTTCTCCTGTCACTGGTTATCACC

CTTTACTGC
```

CAR 4-1BB Costimulatory Domain- Amino Acid Sequence
(SEQ ID NO: 78)
KRGRKKLLYIFKQPFMRPVQTTQEEDGCSCRFPEEEEGGCE CAR 4-1BB Costimulatory Domain- Nucleic Acid Sequence
(SEQ ID NO: 79)
```
AAACGGGGCAGAAAGAAACTCCTGTATATATTCAAACAACCATTTATGAGA

CCAGTACAAACTACTCAAGAGGAAGATGGCTGTAGCTGCCGATTTCCAGAA

GAAGAAGAAGGAGGATGTGAA
```

CAR CD3z Domain- Amino Acid Sequence
(SEQ ID NO: 80)
LRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTY
DALHMQALPPR CAR CD3z Domain- Nucleic Acid Sequence
(SEQ ID NO: 81)
```
CTGAGAGTGAAGTTCAGCAGGAGCGCAGACGCCCCCGCGTACCAGCAGGGC

CAGAACCAGCTCTATAACGAGCTCAATCTAGGACGAAGAGAGGAGTACGAT

GTTTTGGACAAGAGACGTGGCCGGGACCCTGAGATGGGGGGAAAGCCGAGA

AGGAAGAACCCTCAGGAAGGCCTGTACAATGAACTGCAGAAAGATAAGATG

GCGGAGGCCTACAGTGAGATTGGGATGAAAGGCGAGCGCCGGAGGGGCAAG

GGGCACGATGGCCTTTACCAGGGTCTCAGTACAGCCACCAAGGACACCTAC

GACGCCCTTCACATGCAGGCCCTGCCCCCTCGC
```

Figure 3:
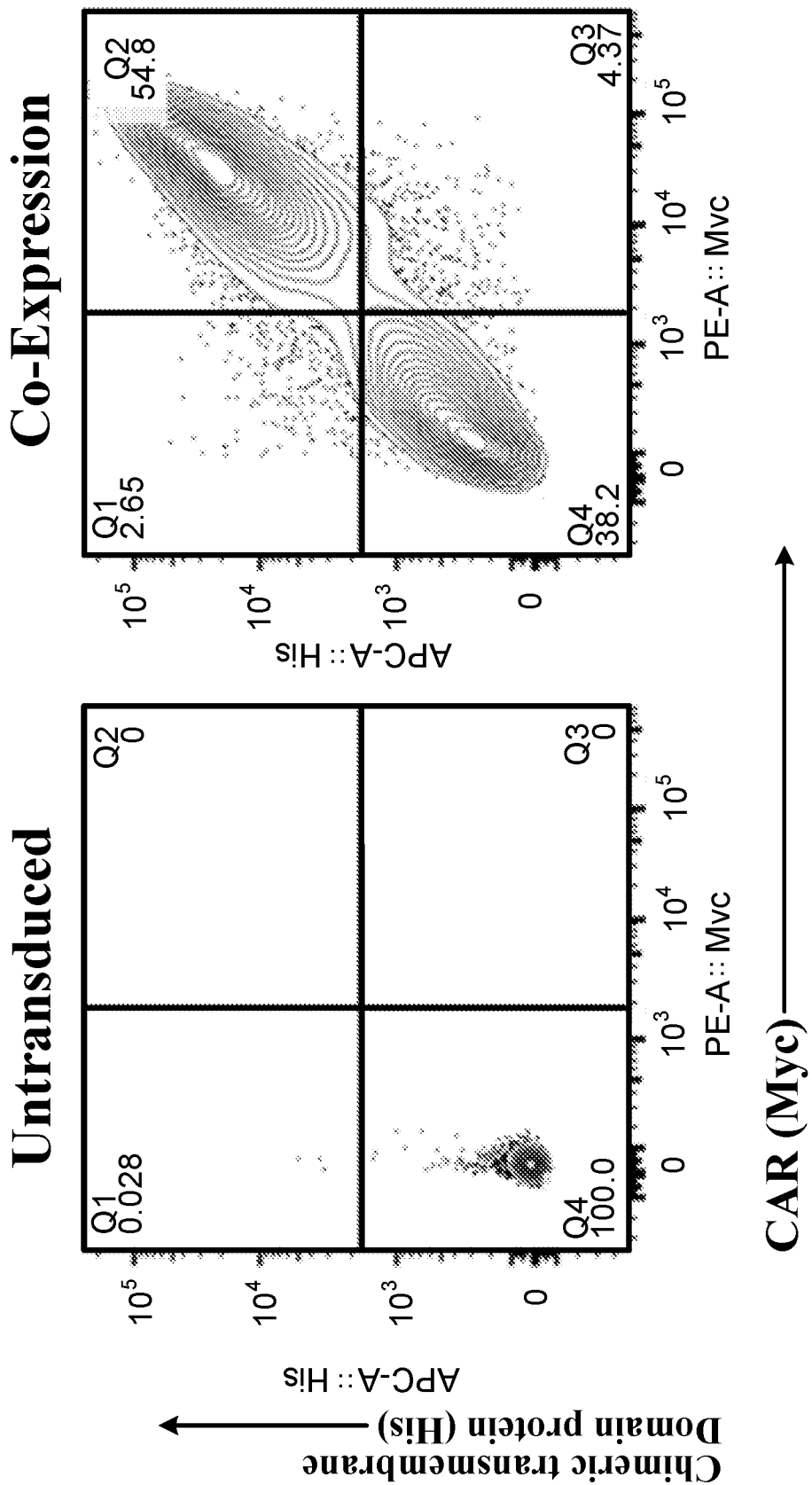
FIG. 3 shows results from flow cytometry experiments using primary human T cells transduced with the vector as shown in FIG. 2. An antibody against His-tag (APC-A::HIS) was used to detect the His-tagged chimeric transmembrane protein of SEQ ID NO: 7. An antibody against c-Myc (PE-A::Myc) was used to detect the chimeric antigen receptor (FMC63-41BB-CD3z CAR). Upon transduction of the vector, primary human T cells expressing both the CAR molecule and the chimeric transmembrane protein were detected.

Example 2. Transduced T-Cells Expressing Both a Chimeric Transmembrane Protein and CAR To determine correct cell surface expression of both chimeric proteins (mbIL2 and FMC63-41BB-CD3z CAR) by flow cytometry, T-cells were stained with fluorochrome conjugated antibodies against the His and Myc tags present at the N-terminus of the mbIL2 chimeric transmembrane protein and FMC63-41BB-CD3z CAR, respectively. Briefly, up to $1 \times 10^6$ primary T-cells were harvested 72 hours post-transduction with the lentiviral vector shown in FIG. 2 and incubated with anti-His (APC; 1:100) and anti-Myc (PE; 1:100) antibodies in PBS+2% FBS (FACS Buffer) for 30 minutes at 4° C. Flow cytometry was performed using BD LSRII Fortessa instruments and analyzed using FlowJo V10 software. The double positive (Myc-PE+, His-APC) population demonstrates co-expression of both chimeric proteins (mbIL2 and FMC63-41BB-CD3z CAR) in primary human T-cells (FIG. 3).

Example 3. Co-Expression of a Chimeric Transmembrane Protein and a CAR Promotes Maintenance of CD62L+ Memory T-Cell Populations IL-2 signaling through JAK3 and STAT5 will cause changes to the phenotype of primary human T-cells, including skewing the CD4 to CD8 ratio toward CD8$^+$ effector cells during ex vivo culture. In addition, IL-2 signaling is typically associated with CD8$^+$ T cell differentiation toward terminal effector T cells and augments the cytotoxic response against target cells. To determine the effect of the chimeric transmembrane protein and CAR expression on the phenotype of primary human T-cells, primary human T-cells expressing none, one, or both of mbIL2 and FMC63-41BB-CD3z CAR were stained with fluorchrome-conjugated antibodies against multiple cell surface markers. Briefly, up to 1×10$^6$ primary human T-cells were harvested 14 days post activation and incubated with anti-Myc (FITC; 1:100), anti-CD4 (BV785; 1:200), anti-CD8 (PE; 1:200), anti-CD45RO (APC; 1:200), and anti CD62L (BV605; 1:200) antibodies in PBS+2% FBS (FACS Buffer) for 30 minutes at 4° C. Flow cytometry was performed using BD LSRII Fortessa instruments and analyzed using FlowJo V10 software. The CD4$^+$ and CD8$^+$ T-cell populations shown are gated on Myc$^+$ populations, while T-cell memory subset populations (CD62L vs CD45RO) are gated on Myc$^+$, CD8$^+$ populations.

Figure 4:
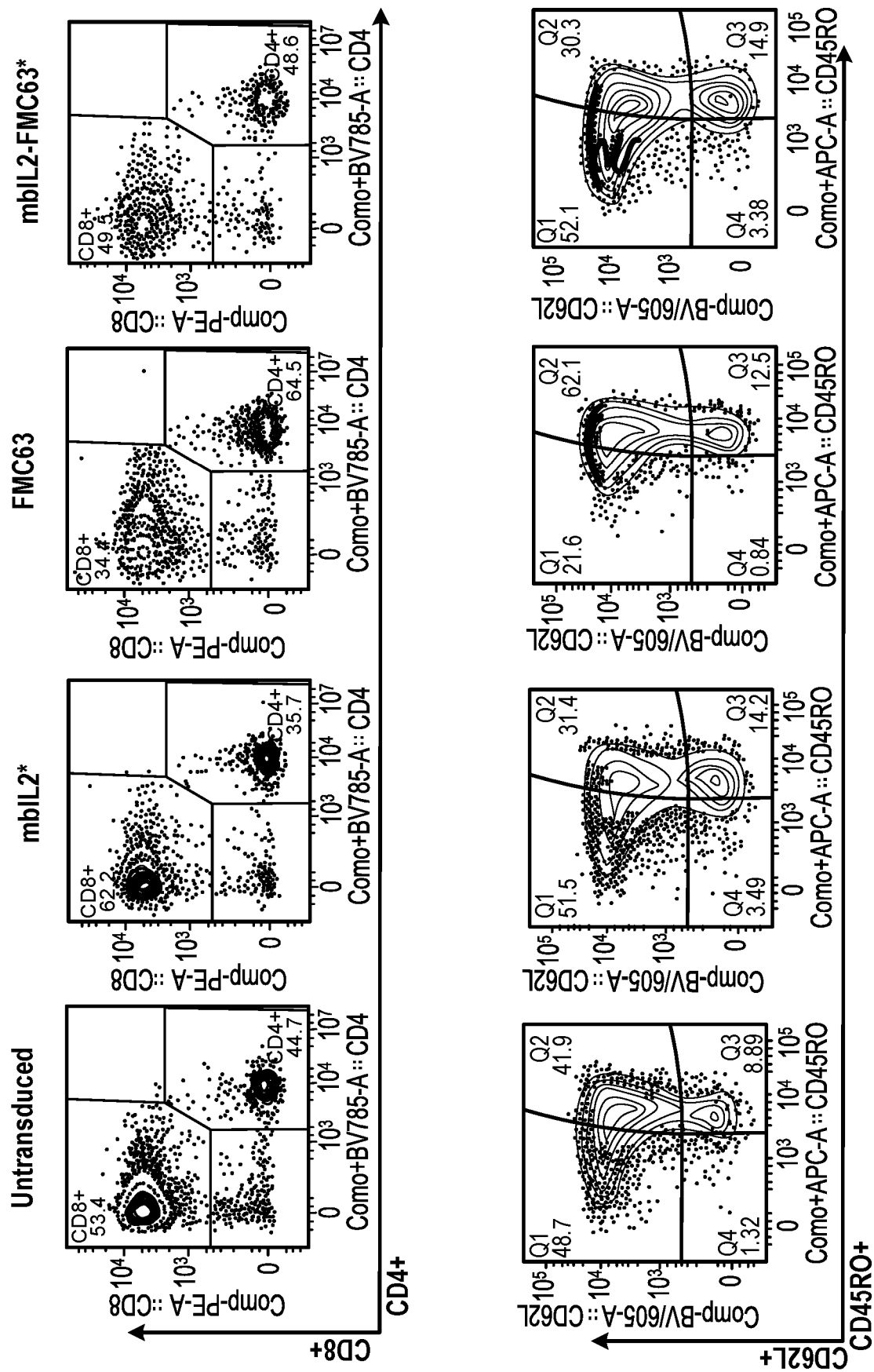
FIG. 4 shows results from flow cytometry experiments using primary human T cells untransduced, or transduced with the chimeric transmembrane protein of SEQ ID NO: 7 alone ("mbIL2"), the chimeric antigen receptor including a FMC63 antigen-binding domain, a 4-1BB costimulatory signaling domain, and a CD3 ITAM alone (FMC63-41BB-CD3z CAR)("FMC63"), or the vector shown in FIG. 2 encoding both FMC63-41BB-CD3z CAR and the chimeric transmembrane protein of SEQ ID NO: 7 ("mbIL2-FMC63"). The antibodies used include an antibody against CD4 (Comp-BV785-A::CD4), an antibody against CD8 (Comp-PE-A::CD8), an antibody against CD45RO (Comp-APC-A::C45R0), and an antibody against CD62L (Comp-BV605-A::CD62L). An asterisk indicates that the cells were cultured in absence of soluble IL-2.

Expression of the mbIL2 and FMC63-41BB-CD3z CAR drives expansion of CD8$^+$ T-cells and preserves stem cell memory populations (CD62L$^+$, CD45RO$^-$), while increasing effector memory populations (CD62L$^-$, CD45RO$^+$), relative to T-cells that express FMC63-41BB-CD3z CAR alone (FIG. 4).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A chimeric transmembrane protein comprising:
   an extracellular IL-2 domain;
   an extracellular sushi domain from an alpha chain of interleukin-2 receptor;
   a transmembrane domain of an alpha chain of interleukin-2 receptor; and
   an intracellular domain capable of signaling.

2. The chimeric transmembrane protein of claim 1, wherein the extracellular IL-2 domain comprises an amino acid sequence that is at least 80% identical to the amino acid sequence of a wildtype IL-2 protein.

3. The chimeric transmembrane protein of claim 1, wherein the chimeric transmembrane protein further comprises a linker sequence positioned between the extracellular IL-2 domain and the extracellular sushi domain.

4. The chimeric transmembrane protein of claim 1, further comprising an additional linker sequence positioned between the extracellular sushi domain and the transmembrane domain.

5. The chimeric transmembrane protein of claim 1, wherein the extracellular sushi domain comprises an amino acid sequence that is at least 80% identical to the amino acid sequence of an extracellular sushi domain of a wildtype alpha chain of interleukin-2 receptor.

6. The chimeric transmembrane protein of claim 1, wherein the transmembrane domain comprises an amino acid sequence that is at least 80% identical to the amino acid sequence of a transmembrane domain of a wildtype alpha chain of interleukin-2 receptor.

7. The chimeric transmembrane protein of claim 1, wherein the chimeric transmembrane protein further comprises an intracellular domain of an alpha chain of interleukin-2 receptor.

* * * * *

```
                        SEQUENCE LISTING

<160> NUMBER OF SEQ ID NOS: 81

<210> SEQ ID NO 1
<211> LENGTH: 134
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser
    130

<210> SEQ ID NO 2
<211> LENGTH: 23
<212> TYPE: PRT
<213> ORGANISM: Artificial Sequence
<220> FEATURE:
<223> OTHER INFORMATION: synthetic linker sequence

<400> SEQUENCE: 2

Gly Gly Gly Ser Gly Gly Gly Gly Ser Gly Gly Gly Ser Gly Gly
1               5                   10                  15

Gly Gly Ser Gly Gly Gly Ser
```

```
                       20

<210> SEQ ID NO 3
<211> LENGTH: 63
<212> TYPE: PRT
<213> ORGANISM: Homo sapiens

<400> SEQUENCE: 3

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser
    50                  55                  60

<210> SEQ ID NO 4
<211> LENGTH: 64
<212> TYPE: PRT
<213> ORGANISM: Homo sapiens

<400> SEQUENCE: 4

Gly His Cys Arg Glu Pro Pro Trp Glu Asn Glu Ala Thr Glu Arg
1               5                   10                  15

Ile Tyr His Phe Val Val Gly Gln Met Val Tyr Gln Cys Val Gln
                20                  25                  30

Gly Tyr Arg Ala Leu His Arg Gly Pro Ala Glu Ser Val Cys Lys Met
            35                  40                  45

Thr His Gly Lys Thr Arg Trp Thr Gln Pro Gln Leu Ile Cys Thr Gly
    50                  55                  60

<210> SEQ ID NO 5
<211> LENGTH: 19
<212> TYPE: PRT
<213> ORGANISM: Homo sapiens

<400> SEQUENCE: 5

Val Ala Val Ala Gly Cys Val Phe Leu Leu Ile Ser Val Leu Leu
1               5                   10                  15

Ser Gly Leu

<210> SEQ ID NO 6
<211> LENGTH: 13
<212> TYPE: PRT
<213> ORGANISM: Homo sapiens

<400> SEQUENCE: 6

Thr Trp Gln Arg Arg Gln Arg Lys Ser Arg Arg Thr Ile
1               5                   10

<210> SEQ ID NO 7
<211> LENGTH: 438
<212> TYPE: PRT
<213> ORGANISM: Artificial Sequence
<220> FEATURE:
<223> OTHER INFORMATION: synthetic mbIL2 sequence

<400> SEQUENCE: 7

Met Leu Leu Leu Val Thr Ser Leu Leu Leu Cys Glu Leu Pro His Pro
1               5                   10                  15
```

```
Ala Phe Leu Leu Ile Pro His His His His His Ala Pro Thr Ser
             20                  25                  30

Ser Ser Thr Lys Lys Thr Gln Leu Gln Leu Glu His Leu Leu Leu Asp
         35                  40                  45

Leu Gln Met Ile Leu Asn Gly Ile Asn Asn Tyr Lys Asn Pro Lys Leu
     50                  55                  60

Thr Arg Met Leu Thr Phe Lys Phe Tyr Met Pro Lys Lys Ala Thr Glu
65                  70                  75                  80

Leu Lys His Leu Gln Cys Leu Glu Glu Glu Leu Lys Pro Leu Glu Glu
                 85                  90                  95

Val Leu Asn Leu Ala Gln Ser Lys Asn Phe His Leu Arg Pro Arg Asp
            100                 105                 110

Leu Ile Ser Asn Ile Asn Val Ile Val Leu Glu Leu Lys Gly Ser Glu
        115                 120                 125

Thr Thr Phe Met Cys Glu Tyr Ala Asp Glu Thr Ala Thr Ile Val Glu
    130                 135                 140

Phe Leu Asn Arg Trp Ile Thr Phe Cys Gln Ser Leu Leu Ser Thr Leu
145                 150                 155                 160

Thr Ser Gly Gly Gly Ser Gly Gly Gly Ser Gly Gly Gly Gly Gly Ser
                165                 170                 175

Gly Gly Gly Gly Ser Gly Gly Gly Ser Leu Gln Glu Leu Cys Asp Asp
            180                 185                 190

Asp Pro Pro Glu Ile Pro His Ala Thr Phe Lys Ala Met Ala Tyr Lys
        195                 200                 205

Glu Gly Thr Met Leu Asn Cys Glu Cys Lys Arg Gly Phe Arg Arg Ile
    210                 215                 220

Lys Ser Gly Ser Leu Tyr Met Leu Cys Thr Gly Asn Ser Ser His Ser
225                 230                 235                 240

Ser Trp Asp Asn Gln Cys Gln Cys Thr Ser Ser Ala Thr Arg Asn Thr
                245                 250                 255

Thr Lys Gln Val Thr Pro Gln Pro Glu Glu Gln Lys Glu Arg Lys Thr
            260                 265                 270

Thr Glu Met Gln Ser Pro Met Gln Pro Val Asp Gln Ala Ser Leu Pro
        275                 280                 285

Gly His Cys Arg Glu Pro Pro Pro Trp Glu Asn Glu Ala Thr Glu Arg
    290                 295                 300

Ile Tyr His Phe Val Val Gly Gln Met Val Tyr Tyr Gln Cys Val Gln
305                 310                 315                 320

Gly Tyr Arg Ala Leu His Arg Gly Pro Ala Glu Ser Val Cys Lys Met
                325                 330                 335

Thr His Gly Lys Thr Arg Trp Thr Gln Pro Gln Leu Ile Cys Thr Gly
            340                 345                 350

Glu Met Glu Thr Ser Gln Phe Pro Gly Glu Glu Lys Pro Gln Ala Ser
        355                 360                 365

Pro Glu Gly Arg Pro Glu Ser Glu Thr Ser Cys Leu Val Thr Thr Thr
    370                 375                 380

Asp Phe Gln Ile Gln Thr Glu Met Ala Ala Thr Met Glu Thr Ser Ile
385                 390                 395                 400

Phe Thr Thr Glu Tyr Gln Val Ala Val Ala Gly Cys Val Phe Leu Leu
                405                 410                 415

Ile Ser Val Leu Leu Leu Ser Gly Leu Thr Trp Gln Arg Arg Gln Arg
            420                 425                 430

Lys Ser Arg Arg Thr Ile
```

```
                    435

<210> SEQ ID NO 8
<211> LENGTH: 410
<212> TYPE: PRT
<213> ORGANISM: Artificial Sequence
<220> FEATURE:
<223> OTHER INFORMATION: synthetic chimeric transmembrane protein

<400> SEQUENCE: 8

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Leu
            115                 120                 125

Leu Ser Thr Leu Thr Ser Gly Gly Gly Ser Gly Gly Gly Ser Gly
130                 135                 140

Gly Gly Ser Gly Gly Gly Ser Gly Gly Gly Ser Leu Gln Glu
145                 150                 155                 160

Leu Cys Asp Asp Asp Pro Pro Glu Ile Pro His Ala Thr Phe Lys Ala
                165                 170                 175

Met Ala Tyr Lys Glu Gly Thr Met Leu Asn Cys Glu Cys Lys Arg Gly
            180                 185                 190

Phe Arg Arg Ile Lys Ser Gly Ser Leu Tyr Met Leu Cys Thr Gly Asn
            195                 200                 205

Ser Ser His Ser Ser Trp Asp Asn Gln Cys Gln Cys Thr Ser Ser Ala
210                 215                 220

Thr Arg Asn Thr Thr Lys Gln Val Thr Pro Gln Pro Glu Glu Gln Lys
225                 230                 235                 240

Glu Arg Lys Thr Thr Glu Met Gln Ser Pro Met Gln Pro Val Asp Gln
                245                 250                 255

Ala Ser Leu Pro Gly His Cys Arg Glu Pro Pro Pro Trp Glu Asn Glu
            260                 265                 270

Ala Thr Glu Arg Ile Tyr His Phe Val Val Gly Gln Met Val Tyr Tyr
            275                 280                 285

Gln Cys Val Gln Gly Tyr Arg Ala Leu His Arg Gly Pro Ala Glu Ser
            290                 295                 300

Val Cys Lys Met Thr His Gly Lys Thr Arg Trp Thr Gln Pro Gln Leu
305                 310                 315                 320

Ile Cys Thr Gly Glu Met Glu Thr Ser Gln Phe Pro Gly Glu Glu Lys
                325                 330                 335

Pro Gln Ala Ser Pro Glu Gly Arg Pro Glu Ser Glu Thr Ser Cys Leu
            340                 345                 350

Val Thr Thr Thr Asp Phe Gln Ile Gln Thr Glu Met Ala Ala Thr Met
```

```
              355                 360                 365
Glu Thr Ser Ile Phe Thr Thr Glu Tyr Gln Val Ala Val Ala Gly Cys
            370                 375                 380
Val Phe Leu Leu Ile Ser Val Leu Leu Leu Ser Gly Leu Thr Trp Gln
385                 390                 395                 400
Arg Arg Gln Arg Lys Ser Arg Arg Thr Ile
                405                 410

<210> SEQ ID NO 9
<211> LENGTH: 22
<212> TYPE: PRT
<213> ORGANISM: Artificial Sequence
<220> FEATURE:
<223> OTHER INFORMATION: synthetic signal sequence

<400> SEQUENCE: 9

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 10
<211> LENGTH: 822
<212> TYPE: DNA
<213> ORGANISM: Homo sapiens

<400> SEQUENCE: 10
agttccctat cactctcttt aatcactact cacagtaacc tcaactcctg ccacaatgta      60
caggatgcaa ctcctgtctt gcattgcact aagtcttgca cttgtcacaa acagtgcacc     120
tacttcaagt tctacaaaga aaacacagct acaactggag catttactgc tggatttaca     180
gatgattttg aatggaatta ataattacaa gaatcccaaa ctcaccagga tgctcacatt     240
taagttttac atgcccaaga aggccacaga actgaaacat cttcagtgtc tagaagaaga     300
actcaaacct ctggaggaag tgctaaattt agctcaaagc aaaaactttc acttaagacc     360
cagggactta atcagcaata tcaacgtaat agttctggaa ctaaagggat ctgaaacaac     420
attcatgtgt gaatatgctg atgagacagc aaccattgta gaatttctga acagatggat     480
taccttttgt caaagcatca tctcaacact gacttgataa ttaagtgctt cccacttaaa     540
acatatcagg ccttctattt atttaaatat ttaaatttta tatttattgt tgaatgtatg     600
gtttgctacc tattgtaact attattctta atcttaaaac tataaatatg gatcttttat     660
gattcttttt gtaagcccta ggggctctaa aatggtttca cttatttatc ccaaaatatt     720
tattattatg ttgaatgtta aatatagtat ctatgtagat tggttagtaa aactatttaa     780
taaatttgat aaatataaaa aaaaaaaaaa aaaaaaaaa aa                         822

<210> SEQ ID NO 11
<211> LENGTH: 134
<212> TYPE: PRT
<213> ORGANISM: Macaca mulatta

<400> SEQUENCE: 11

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
 65                  70                  75                  80

Arg Asp Thr Lys Asp Leu Ile Ser Asn Ile Asn Val Ile Val Leu Glu
                85                  90                  95

Leu Lys Gly Ser Glu Thr Thr Leu Met Cys Glu Tyr Ala Asp Glu Thr
            100                 105                 110

Ala Thr Ile Val Glu Phe Leu Asn Arg Trp Ile Thr Phe Cys Gln Ser
                115                 120                 125

Ile Ile Ser Thr Leu Thr
            130

<210> SEQ ID NO 12
<211> LENGTH: 497
<212> TYPE: DNA
<213> ORGANISM: Macaca mulatta

<400> SEQUENCE: 12
atgtacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaattga acatcttca gtgtctagaa     240 gaagaactca aacctctgga ggaagtgcta aatttagctc aaagcaaaaa ctttcactta    300
agagatacca aggacttaat cagcaatatc aacgtaatag ttctggaact aaagggatct    360
gaaacaacac tgatgtgtga atatgctgat gagacagcaa ccattgtaga atttctgaac    420
agatggatta ccttttgtca agcatcatc tcaacactga cctgataatt aagtgcttcc     480
cacttaaaac atatcag                                                   497

<210> SEQ ID NO 13
<211> LENGTH: 121
<212> TYPE: PRT
<213> ORGANISM: Gallus gallus

<400> SEQUENCE: 13

Ala Ser Leu Ser Ser Glu Lys Trp Lys Thr Leu Gln Thr Leu Ile Lys
 1               5                  10                  15

Asp Leu Glu Ile Leu Glu Asn Ile Lys Asn Lys Ile His Leu Glu Leu
                20                  25                  30

Tyr Thr Pro Thr Glu Thr Gln Glu Cys Thr Gln Gln Thr Leu Gln Cys
            35                  40                  45

Tyr Leu Gly Glu Val Val Thr Leu Lys Lys Glu Thr Glu Asp Asp Thr
 50                  55                  60

Glu Ile Lys Glu Glu Phe Val Thr Ala Ile Gln Asn Ile Glu Lys Asn
 65                  70                  75                  80

Leu Lys Ser Leu Thr Gly Leu Asn His Thr Gly Ser Glu Cys Lys Ile
                85                  90                  95

Cys Glu Ala Asn Asn Lys Lys Phe Pro Asp Phe Leu His Glu Leu
            100                 105                 110

Thr Asn Phe Val Arg Tyr Leu Gln Lys
            115                 120

<210> SEQ ID NO 14

<211> LENGTH: 798
<212> TYPE: DNA
<213> ORGANISM: Gallus gallus

<400> SEQUENCE: 14

```
atcacctcac attgtacatc acaatttgaa taccagcata cagataactg ggacactgcc    60
atgatgtgca agtactgat ctttggctgt atttcggtag caatgctaat gactacagct    120
tatggagcat ctctatcatc agaaaaatgg aaaactcttc aaacattaat aaaggattta   180
gaaatattgg aaatatcaa gaataagatt catctcgagc tctacacacc aactgagacc    240
caggagtgca cccagcaaac tctgcagtgt tacctgggag aagtggttac tctgaagaaa   300
gaaactgaag atgacactga aattaaagaa gaatttgtaa ctgctattca aaatatcgaa   360
aagaacctca gagtcttac gggtctaaat cacaccggaa gtgaatgcaa gatctgtgaa    420
gctaacaaca gaaaaaatt tcctgatttt ctccatgaac tgaccaactt tgtgagatat    480
ctgcaaaaat aagcaactaa tcatttttat tttactgcta tgttatttat ttaattattt   540
aattacagat aatttatata ttttatcccg tggctaacta atctgctgtc cattctggga   600
ccactgtatg ctcttagtct gggtgatatg acgtctgttc taagatcata tttgatcctt   660
tctgtaagcc ctacgggctc aaaatgtacg ttggaaaact gattgattct cactttgtcg   720
gtaaagtgat atgtgtttac tgaaagaatt tttaaaagtc acttctagat gacatttaat   780
aaatttcagt aatatatg                                                 798
```

<210> SEQ ID NO 15
<211> LENGTH: 149
<212> TYPE: PRT
<213> ORGANISM: Mus musculus

<400> SEQUENCE: 15

```
Ala Pro Thr Ser Ser Thr Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 16
<211> LENGTH: 955
<212> TYPE: DNA
<213> ORGANISM: Mus musculus

<400> SEQUENCE: 16

```
tatcaccctt gctaatcact cctcacagtg acctcaagtc ctgcaggcat gtacagcatg      60
cagctcgcat cctgtgtcac attgacactt gtgctccttg tcaacagcgc acccacttca     120
agctccactt caagctctac agcggaagca cagcagcagc agcagcagca gcagcagcag     180
cagcagcacc tggagcagct gttgatggac ctacaggagc tcctgagcag gatggagaat     240
tacaggaacc tgaaactccc caggatgctc accttcaaat tttacttgcc caagcaggcc     300
acagaattga agatcttca gtgcctagaa gatgaacttg acctctgcg gcatgttctg       360 gatttgactc aaagcaaaag ctttcaattg gaagatgctg agaatttcat cagcaatatc     420
agagtaactg ttgtaaaact aaagggctct gacaacacat ttgagtgcca attcgatgat     480
gagtcagcaa ctgtggtgga ctttctgagg agatggatag ccttctgtca agcatcatc     540 tcaacaagcc ctcaataact atgtacctcc tgcttacaac acataaggct ctctatttat     600
ttaaatattt aactttaatt tattttttgga tgtattgttt actatctttt gtaactacta     660
gtcttcagat gataaatatg gatctttaaa gattcttttt gtaagcccca agggctcaaa     720
aatgttttaa actatttatc tgaaattatt tattatattg aattgttaaa tatcatgtgt     780
aggtagactc attaataaaa gtatttagat gattcaaata taaataagct cagatgtctg     840
tcatttttag gacagcacaa agtaagcgct aaaataactt ctcagttatt cctgtgaact     900
ctatgttaat cagtgttttc aagaaataaa gctctcctct aaaaaaaaaa aaaaa          955
```

```
<210> SEQ ID NO 17
<211> LENGTH: 251
<212> TYPE: PRT
<213> ORGANISM: Homo sapiens

<400> SEQUENCE: 17

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205
```

```
Met Glu Thr Ser Ile Phe Thr Thr Glu Tyr Gln Val Ala Val Ala Gly
        210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250

<210> SEQ ID NO 18
<211> LENGTH: 3216
<212> TYPE: DNA
<213> ORGANISM: Homo sapiens

<400> SEQUENCE: 18
```

| | | | | | |
|---|---|---|---|---|---|
| ggcagtttcc | tggctgaaca | cgccagccca | atacttaaag | agagcaactc | ctgactccga | 60 |
| tagagactgg | atggacccac | aagggtgaca | gcccaggcgg | accgatcttc | ccatcccaca | 120 |
| tcctccggcg | cgatgccaaa | agaggctga | cggcaactgg | gccttctgca | gagaaagacc | 180 |
| tccgcttcac | tgccccggct | ggtcccaagg | gtcaggaaga | tggattcata | cctgctgatg | 240 |
| tggggactgc | tcacgttcat | catggtgcct | ggctgccagg | cagagctctg | tgacgatgac | 300 |
| ccgccagaga | tcccacacgc | cacattcaaa | gccatggcct | acaaggaagg | aaccatgttg | 360 |
| aactgtgaat | gcaagagagg | tttccgcaga | ataaaaagcg | ggtcactcta | tatgctctgt | 420 |
| acaggaaact | ctagccactc | gtcctgggac | aaccaatgtc | aatgcacaag | ctctgccact | 480 |
| cggaacacaa | cgaaacaagt | gacacctcaa | cctgaagaac | agaaagaaag | gaaaaccaca | 540 |
| gaaatgcaaa | gtccaatgca | gccagtggac | caagcgagcc | ttccaggtca | ctgcagggaa | 600 |
| cctccaccat | gggaaaatga | agccacagag | agaatttatc | atttcgtggt | ggggcagatg | 660 |
| gtttattatc | agtgcgtcca | gggatacagg | gctctacaca | gaggtcctgc | tgagagcgtc | 720 |
| tgcaaaatga | cccacgggaa | gacaaggtgg | acccagcccc | agctcatatg | cacaggtgaa | 780 |
| atggagacca | gtcagtttcc | aggtgaagag | aagcctcagg | caagcccga | aggccgtcct | 840 |
| gagagtgaga | cttcctgcct | cgtcacaaca | acagattttc | aaatacagac | agaaatggct | 900 |
| gcaaccatgg | agacgtccat | atttacaaca | gagtaccagg | tagcagtggc | cggctgtgtt | 960 |
| ttcctgctga | tcagcgtcct | cctcctgagt | gggctcacct | ggcagcggag | acagaggaag | 1020 |
| agtagaagaa | caatctagaa | aaccaaaaga | acaagaattt | cttggtaaga | gccgggaac | 1080 |
| agacaacaga | agtcatgaag | cccaagtgaa | atcaaaggtg | ctaaatggtc | gcccaggaga | 1140 |
| catccgttgt | gcttgcctgc | gttttggaag | ctctgaagtc | acatcacagg | acacggggca | 1200 |
| gtggcaacct | tgtctctatg | ccagctcagt | cccatcagag | agcgagcgct | acccacttct | 1260 |
| aaatagcaat | ttcgccgttg | aagaggaagg | gcaaaaccac | tagaactctc | catcttattt | 1320 |
| tcatgtatat | gtgttcatta | aagcatgaat | ggtatggaac | tctctccacc | ctatatgtag | 1380 |
| tataaagaaa | agtaggttta | cattcatctc | attccaactt | cccagttcag | gagtcccaag | 1440 |
| gaaagcccca | gcactaacgt | aaatacacaa | cacacacact | ctaccctata | caactggaca | 1500 |
| ttgtctgcgt | ggttcctttc | tcagccgctt | ctgactgctg | attctcccgt | tcacgttgcc | 1560 |
| taataaacat | ccttcaagaa | ctctgggctg | ctacccagaa | atcattttac | ccttggctca | 1620 |
| atcctctaag | ctaaccccct | tctactgagc | cttcagtctt | gaatttctaa | aaacagagg | 1680 |
| ccatggcaga | ataatctttg | ggtaacttca | aaacggggca | gccaaaccca | tgaggcaatg | 1740 |
| tcaggaacag | aaggatgaat | gaggtcccag | gcagagaatc | atacttagca | aagttttacc | 1800 |
| tgtgcgttac | taattggcct | ctttaagagt | tagtttcttt | gggattgcta | tgaatgatac | 1860 |

```
cctgaatttg gcctgcacta atttgatgtt tacaggtgga cacacaaggt gcaaatcaat    1920
gcgtacgttt cctgagaagt gtctaaaaac accaaaaagg gatccgtaca ttcaatgttt    1980
atgcaaggaa ggaaagaaag aaggaagtga agagggagaa gggatggagg tcacactggt    2040
agaacgtaac cacggaaaag agcgcatcag gcctggcacg gtggctcagg cctataaccc    2100
cagctcccta ggagaccaag gcgggagcat ctcttgaggc caggagtttg agaccagcct    2160
gggcagcata gcaagacaca tccctacaaa aaattagaaa ttggctggat gtggtggcat    2220
acgcctgtag tcctagccac tcaggaggct gaggcaggag gattgcttga gcccaggagt    2280
tcgaggctgc agtcagtcat gatggcacca ctgcactcca gcctgggcaa cagagcaaga    2340
tcctgtcttt aaggaaaaaa agacaagatg agcataccag cagtccttga acattatcaa    2400
aaagttcagc atattagaat caccgggagg ccttgttaaa agagttcgct gggcccatct    2460
tcagagtctc tgagttgttg gtctggaata gagccaaatg ttttgtgtgt ctaacaattc    2520
ccaggtgctg ttgctgctgc tactattcca ggaacacact ttgagaacca ttgtgttatt    2580
gctctgcacg cccaccccact ctcaactccc acgaaaaaaa tcaacttcca gagctaagat    2640
ttcggtggaa gtcctggttc catatctggt gcaagatctc ccctcacgaa tcagttgagt    2700
caacattcta gctcaacaac atcacacgat taacattaac gaaaattatt catttgggaa    2760
actatcagcc agtttcact tctgaagggg caggagagtg ttatgagaaa tcacggcagt    2820
tttcagcagg gtccagattc agattaaata actattttct gtcatttctg tgaccaacca    2880
catacaaaca gactcatctg tgcactctcc ccctcccct tcaggtatat gttttctgag    2940
taaagttgaa aagaatctca gaccagaaaa tatagatata tatttaaatc ttacttgagt    3000
agaactgatt acgactttttg ggtgttgagg ggtctataag atcaaaactt ttccatgata    3060
atactaagat gttatcgacc atttatctgt ccttctctca aaagtgtatg gtggaatttt    3120
ccagaagcta tgtgatacgt gatgatgtca tcactctgct gttaacatat aataaattta    3180
ttgctattgt ttataaaaga ataaatgata ttttttt                              3216
```

<210> SEQ ID NO 19
<211> LENGTH: 244
<212> TYPE: PRT
<213> ORGANISM: Pan troglodytes

<400> SEQUENCE: 19

```
Glu Leu Cys Asp Asp Pro Pro Glu Ile Thr His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Thr Val Tyr
        115                 120                 125
```

Tyr Gln Cys Val Gln Gly Tyr Arg Ala Leu His Arg Gly Pro Ala Glu
130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
                180                 185                 190

Leu Ile Thr Thr Thr Asp Phe Gln Ile Gln Thr Glu Met Ala Ala Thr
                195                 200                 205

Met Glu Thr Phe Ile Phe Thr Thr Glu Tyr Gln Val Ala Val Ala Gly
210                 215                 220

Cys Val Phe Leu Leu Ile Ser Val Leu Leu Leu Ser Gly Leu Thr Trp
225                 230                 235                 240

Gln Arg Arg Gln

<210> SEQ ID NO 20
<211> LENGTH: 798
<212> TYPE: DNA
<213> ORGANISM: Pan troglodytes

<400> SEQUENCE: 20
atggattcat acctgctgat gtggggactg ctcacgctca tcatggtgcc tggctgcttt       60
gcagagctct gtgacgatga cccgccagag atcacacacg ccacattcaa agccatggcc      120
tacaaggaag gaaccatgtt gaactgtgaa tgcaagagag gtttccgcag aataaaaagc      180
gggtcactct atatgctctg tacaggaaac tctagccact cgtcctggga caaccaatgt      240
caatgcacaa gctctgccac tcggaacaca acgaaacaag tgacacctca acctgaagaa      300
cagaaagaaa ggaaaaccac agaaatgcaa agtccaatgc agccagtgga ccaagcgagc      360
cttccaggtc actgcaggga acctccaccg tgggaaaatg aagccacaga gagaatttat      420
catttcgtgg tggggcagac ggtttactac cagtgcgtcc agggatacag ggctctacac      480
agaggtcctg ctgagagcgt ctgcaaaatg acccatggga agacaaggtg gacccagccc      540
cagctcatat gcacaggtga aatggagacc agtcagtttc aggtgaagaa gaagcctcag      600
gcaagccccg aaggccgtcc tgagagtgag acttcctgcc tcatcacaac aacagatttt      660
caaatacaga cagaaatggc tgcaaccatg gagacgttca tatttacaac agagtaccag      720
gtagcagtgg ccggctgtgt tttcctgctg atcagcgtcc tcctcctgag tgggctcacc      780
tggcagcgga gacagtaa                                                   798

<210> SEQ ID NO 21
<211> LENGTH: 251
<212> TYPE: PRT
<213> ORGANISM: Macaca mulatta

<400> SEQUENCE: 21

Glu Leu Cys Asp Asp Asp Pro Pro Lys Ile Thr His Ala Thr Phe Lys
1               5                   10                  15

Ala Val Ala Tyr Lys Glu Gly Thr Met Leu Asn Cys Glu Cys Lys Arg
                20                  25                  30

Gly Phe Arg Arg Ile Lys Ser Gly Ser Pro Tyr Met Leu Cys Thr Gly
                35                  40                  45

Asn Ser Ser His Ser Ser Trp Asp Asn Gln Cys Gln Cys Thr Ser Ser
            50                  55                  60

Ala Ala Arg Asn Thr Thr Lys Gln Val Thr Pro Gln Pro Glu Glu Gln
65                  70                  75                  80

Lys Glu Arg Lys Thr Thr Glu Met Gln Ser Gln Met Gln Leu Ala Asp
                85                  90                  95

Gln Val Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135                 140

Ser Ile Cys Lys Met Thr His Gly Lys Thr Arg Trp Thr Gln Pro Gln
145                 150                 155                 160

Leu Ile Cys Thr Gly Glu Thr Glu Pro Ser Gln Phe Pro Gly Glu Glu
                165                 170                 175

Glu Pro Gln Ala Ser Pro Asp Gly Leu Pro Glu Ser Glu Thr Ser Arg
            180                 185                 190

Leu Val Thr Thr Thr Asp Phe Arg Ile Gln Thr Glu Val Ala Ala Thr
            195                 200                 205

Met Glu Thr Phe Ile Phe Thr Thr Glu Tyr Gln Val Ala Val Ala Gly
210                 215                 220

Cys Val Phe Leu Leu Ile Ser Val Leu Leu Leu Ser Gly Leu Thr Trp
225                 230                 235                 240

Gln Arg Arg Gln Arg Lys Asn Arg Arg Thr Ile
            245                 250

<210> SEQ ID NO 22
<211> LENGTH: 934
<212> TYPE: DNA
<213> ORGANISM: Macaca mulatta

<400> SEQUENCE: 22
atggatccat acctgctcat gtggggactg ctcacgttca tcacggtgcc tggctgccag      60
gcagagctct gtgacgatga cccgccaaaa atcacacatg ccacattcaa agccgtggcc     120
tacaaggaag gaaccatgtt gaactgtgaa tgcaagagag gtttccgcag aataaaaagc     180
gggtcaccct atatgctctg tacaggaaac tctagccact cgtcctggga caaccaatgt     240
caatgcacaa gctctgctgc tcggaacaca acaaaacaag tgacacctca acctgaagaa     300
cagaaagaaa gaaaaaccac agaaatgcaa agtcaaatgc agctggcgga ccaagtgagc     360
cttccaggtc actgcaggga acctccaccg tgggaaaatg aagccacaga agaatttat      420
catttcgtgg tggggcagat ggtttactac cagtgcgtcc agggatacag ggctctacac     480
agaggtcctg ctgagagcat ctgcaaaatg acccacggga gacaagatg acccagccc      540
cagctcatat gcacaggtga acggagccc agtcagtttc caggtgaaga ggagcctcag     600
gcaagccccg acggccttcc tgagagtgag acttcccgcc tcgtcacaac aacagatttt     660
cgaatacaga cagaagtggc tgcaaccatg gaaacgttca tatttacaac agagtaccaa     720
gtagcagtgg ccggctgtgt tttcctgctg atcagcgtcc tcctgctgag tgggctcacc     780
tggcagcgga gacagaggaa gaatagaaga acaatctaga aaaccaaaag aacaagaact     840
tcttggtaag aagccgagaa cagacaacag aagtcatgaa gcccaagcga aatcaaaggt     900
gctaaatgct tgcccaggag acatccgttg tgct                                934

<210> SEQ ID NO 23
<211> LENGTH: 247

<212> TYPE: PRT
<213> ORGANISM: Mus musculus

<400> SEQUENCE: 23

```
Glu Leu Cys Leu Tyr Asp Pro Pro Glu Val Pro Asn Ala Thr Phe Lys
1               5                   10                  15

Ala Leu Ser Tyr Lys Asn Gly Thr Ile Leu Asn Cys Glu Cys Lys Arg
            20                  25                  30

Gly Phe Arg Arg Leu Lys Glu Leu Val Tyr Met Arg Cys Leu Gly Asn
        35                  40                  45

Ser Trp Ser Ser Asn Cys Gln Cys Thr Ser Asn Ser His Asp Lys Ser
    50                  55                  60

Arg Lys Gln Val Thr Ala Gln Leu Glu His Gln Lys Glu Gln Gln Thr
65                  70                  75                  80

Thr Thr Asp Met Gln Lys Pro Thr Gln Ser Met His Gln Glu Asn Leu
                85                  90                  95

Thr Gly His Cys Arg Glu Pro Pro Trp Lys His Glu Asp Ser Lys
            100                 105                 110

Arg Ile Tyr His Phe Val Glu Gly Gln Ser Val His Tyr Glu Cys Ile
            115                 120                 125

Pro Gly Tyr Lys Ala Leu Gln Arg Gly Pro Ala Ile Ser Ile Cys Lys
    130                 135                 140

Met Lys Cys Gly Lys Thr Gly Trp Thr Gln Pro Gln Leu Thr Cys Val
145                 150                 155                 160

Asp Glu Arg Glu His His Arg Phe Leu Ala Ser Glu Ser Gln Gly
                165                 170                 175

Ser Arg Asn Ser Ser Pro Glu Ser Glu Thr Ser Cys Pro Ile Thr Thr
            180                 185                 190

Thr Asp Phe Pro Gln Pro Thr Glu Thr Thr Ala Met Thr Glu Thr Phe
        195                 200                 205

Val Leu Thr Met Glu Tyr Lys Val Ala Val Ala Ser Cys Leu Phe Leu
    210                 215                 220

Leu Ile Ser Ile Leu Leu Leu Ser Gly Leu Thr Trp Gln His Arg Trp
225                 230                 235                 240

Arg Lys Ser Arg Arg Thr Ile
                245
```

<210> SEQ ID NO 24
<211> LENGTH: 4428
<212> TYPE: DNA
<213> ORGANISM: Mus musculus

<400> SEQUENCE: 24

```
aagttcctgc tgagcagatc agcctaatgc ttaaatagaa caactcctgg ctgtcattga    60
cattgtctaa aagccaagat gacagactga gaggcctgag cccttgttct ggcattctcc   120
caggaagatg cagtaaaggg gttgacccaa tatactgcag agaatttcat ccagttccct   180
cctccatcct gatcccatgt gccaggaaga tggagccacg cttgctgatg ttggggtttc   240
tctcattaac catagtaccc agttgtcggg cagaactgtg tctgtatgac ccacccgagg   300
tccccaatgc cacattcaaa gccctctcct acaagaacgg caccatccta aactgtgaat   360
gcaagagagg tttccgaaga ctaaaggaat tggtctatat gcgttgctta ggaaactcct   420
ggagcagcaa ctgccagtgc accagcaact cccatgacaa atcgagaaag caagttacag   480
ctcaacttga acaccagaaa gagcaacaaa ccacaacaga catgcagaag ccaacacagt   540
```

```
ctatgcacca agagaacctt acaggtcact gcagggagcc acctccttgg aaacatgaag    600
attccaagag aatctatcat ttcgtggaag gacagagtgt tcactacgag tgtattccgg    660
gatacaaggc tctacagaga ggtcctgcta ttagcatctg caagatgaag tgtgggaaaa    720
cggggtggac tcagcccag ctcacatgtg tagatgaaag agaacaccac cgatttctgg     780
ctagtgagga atctcaagga agcagaaatt cttctcccga gagtgagact tcctgcccca   840
taaccaccac agacttccca caacccacag aaacaactgc aatgacggag acatttgtgc   900
tcacaatgga gtataaggta gcagtggcca gctgcctctt cctgctcatc agcatcctcc   960
tcctgagcgg gctcacctgg caacacagat ggaggaagag cagaagaacc atctagcaag  1020
ctagaaaagt cagagcccag gcaagcggat gggaatcaca aagctcaagc caaatctgag  1080
acgccaagca ttcacctaac ggctgtttcc ttctgatccc tgggtttcta aacattctg    1140 aagtcacagg acataacagc aactctatca ctaaactgga ctttgccatt gaagaatagg  1200
atctaaccac ttcagcacag cagttctaaa gctttaatgg gagagagggc ccaacagtgc  1260
tctgtgtgtt ttgttttgt gtatatctgt tgatgggagc tgagatggtg tggtcacttt    1320
tcatgtaaca tatagtatag aaaaagtagc tttaggttga cttcattgtt acaacccagt    1380
ttggaaagcc caagtaaaac tcagcactaa tgtaaataat tcctcctcct cctcctctct   1440
cttttcatcc tccgctccat cttcctcttc ttcctcctcc ttttccacct cctctgtccc    1500
tacccacccc cacccatcca cttttccttct tcctttctgc tctcacaagc tcatcctagc    1560
tacacgtgca tggctggctc ctttttcaac ctctgtttgc ctaactggct cttctgattt    1620
catcacttac tgatcagcct ttaaaactct gagctggcaa agatgactct atctatgttc    1680
ttggctcagt cccagaagga aaccccttt tcatgaagct tcagttttga catcctgaag    1740
aacagaaact gtggcagaac aatcttcaga taacatcaaa acaaagtgga gaagccacgg    1800
gaactgtgga gctctggtat tcagaagcct gtgtctaggg tctgcgccag gagcagaagg   1860
ctgaaggaag tccaggacg tggacttaga tgctttccca gcaggccact ctaagcgctg    1920
gtttctttgg gacagctgtc aattgtacgc tcaatttagc ctgcactaat ctgatgctta   1980
caggtgaaca ctcaaggcac aggtatggac ttggtacata ccgtgaaaac actggaaaga   2040
aaagaatact ttcaagttta cagaaggaag gaaggaaaaa ggaagcagag gtggtgatta   2100
tacaaaagat tagctgtaga ctggatatcc caggcatcct cggataatgc ccccgccca   2160 gcaccctgat ccaggtcacc aaagccttgt gagatcagac tgcagagcca gtctgtctct   2220
gagtcagtaa atgtagaatt tggatttctc acaagttcct ggcggtgtct ttttttttt   2280 taatattttt tattaggtat tttcctcatt tacatttcca atgctatccc aaaagtcccc   2340 catacctcc cccacactcc cctacccacc cactcccact ttttggccct ggtgttcccc   2400
tgtactgggg catataaagt ttgcaagtcc tggtggtgtc tttatgctga tctctagccc   2460
acactttgtg aggcactggg ctatcccagt gtgctctcct cttccacaga taccaaaagc   2520
acctgggttt gatgctcaga cttctgagca cgttcttgtt caatctcttg cgtaagattt    2580
cctctcagat gagttgagtc agattctcat gtttaacagt gttttagggg attcacagaa    2640
gcccaaacta tcagttttca tttctgaaaa ggctggaaaa ttttatgaaa aactttcaaa    2700
ggtcagacag agccattttg agtcttttat gtgaccaagt atgaaccaga tctttcctat    2760
ctatggtctc ccctttccaa aatatatctt ttgtggggac acggcaagga ggaaagttaa   2820
atagaatctc aagctactaa ttttagaaaa gaaaaaaata ttaaactctt actaagagc    2880 tgtgggtagt ggtacacacc tgtaagccca gctctcagga gactgaggca ggaggattgc   2940
```

```
agtgagtcag agatcagctt cacctacaag caaaaccctg ccttacccct caacctttcc    3000
ataaaaacag tcttacttgt gtaaaattaa tttttaatac atatttgtgc acgatgtgtg    3060
tgcctggtgc ccagggaagc caaaaaaata tgttcaatgt ccctggaata ggtggttatg    3120
agctgccatg gaggtgatgg gatttaaacc cctgttctct gaaaaagcag ctagttctct    3180
taaccactga gccatctcta cagccccatt aaattgaatt ttattgtcat tactcaatat    3240
gggagatggg gtaatgataa caattttttt tttataatac taagatgttt agctatttta    3300
ctctccttca caagtgtaga gtagaatttt ctagaagcta catgcatgat attatcgctc    3360
tggtgttaac acataatgga tttatcttgt taataaaaga attagtaaat aatattttaa    3420
attttttctt tgttttagtt ttaagatgat taatatctat agatactagt gtacattaag    3480
aaagcctttg ggatcctcaa tcattttgca tggttttagt aattttttaa taacataaag    3540
aaggtctgac agattatgct aaagagctat tgtggtatgg attagaaatg gcccccacag    3600
gctcctgtgt tcaaacatca gctagcagtg ctgctttggg ttttggaacc tttaagaggt    3660
ggggccttgc ttaaggagat aggtcactgg aggtgaacca gacttgcttc cagtctccct    3720
ctctgctgtc ccaggaagcc atcatatgag gagtttcaca acatacttct gctgccacag    3780
agtccctcca gtaaggcacg tactggccac tgtgtagtgt accctctaaa actgagctag    3840
agctcccctc tcctccctac actatctctg ttgatgcttt gtcacggtga tgaagaacat    3900
aagtaaggca aagacaagac atagtttgga gactcacgtg agcatctcag ccagactcag    3960
gcacagctgc gatgtgggaa ttatcaagca tgagatgcaa agcaatggaa atgaatcgt     4020
tatgacagaa gcctacatct agtcttccct tcttcccatt agtaataata gcccgtgttt    4080
tagaagaaca catctttttg gtgttctagg tagcttatat tgcaaatgtg cacaatcta    4140
agagaaatct gggatgaggg aacctcagtg aaagattctc cttgatcaga ttgtcccact    4200
gatgattgat atgggaaggc ccaacccact gtgaaaggca ccacccattg gcaggatgac    4260
tggggttata gaagcaaaca ggctgagcat gagccagtga gcaagccagt aagcagtggc    4320
ttctctttgg aagaagcatg gctttcttcc gtggcttctg tttgatctct ctcaatgata    4380
gattgtgacc tagaagtata agctaaaata aaccatttct tacccata               4428
```

<210> SEQ ID NO 25
<211> LENGTH: 219
<212> TYPE: PRT
<213> ORGANISM: Homo sapiens

<400> SEQUENCE: 25

```
Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
                35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
                100                 105                 110
```

-continued

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln
    210                 215

<210> SEQ ID NO 26
<211> LENGTH: 63
<212> TYPE: PRT
<213> ORGANISM: Pan troglodytes

<400> SEQUENCE: 26

Glu Leu Cys Asp Asp Pro Pro Glu Ile Thr His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser
    50                  55                  60

<210> SEQ ID NO 27
<211> LENGTH: 64
<212> TYPE: PRT
<213> ORGANISM: Pan troglodytes

<400> SEQUENCE: 27

Gly His Cys Arg Glu Pro Pro Trp Glu Asn Glu Ala Thr Glu Arg
1               5                   10                  15

Ile Tyr His Phe Val Val Gly Gln Thr Val Tyr Gln Cys Val Gln
            20                  25                  30

Gly Tyr Arg Ala Leu His Arg Gly Pro Ala Glu Ser Val Cys Lys Met
        35                  40                  45

Thr His Gly Lys Thr Arg Trp Thr Gln Pro Gln Leu Ile Cys Thr Gly
    50                  55                  60

<210> SEQ ID NO 28
<211> LENGTH: 63
<212> TYPE: PRT
<213> ORGANISM: Macaca mulatta

<400> SEQUENCE: 28

Glu Leu Cys Asp Asp Pro Pro Lys Ile Thr His Ala Thr Phe Lys
1               5                   10                  15

Ala Val Ala Tyr Lys Glu Gly Thr Met Leu Asn Cys Glu Cys Lys Arg
            20                  25                  30

Gly Phe Arg Arg Ile Lys Ser Gly Ser Pro Tyr Met Leu Cys Thr Gly
        35                  40                  45

```
Asn Ser Ser His Ser Ser Trp Asp Asn Gln Cys Gln Cys Thr Ser
    50                  55                  60
```

<210> SEQ ID NO 29
<211> LENGTH: 64
<212> TYPE: PRT
<213> ORGANISM: Macaca mulatta

<400> SEQUENCE: 29

```
Gly His Cys Arg Glu Pro Pro Trp Glu Asn Glu Ala Thr Glu Arg
1               5                   10                  15

Ile Tyr His Phe Val Val Gly Gln Met Val Tyr Tyr Gln Cys Val Gln
                20                  25                  30

Gly Tyr Arg Ala Leu His Arg Gly Pro Ala Glu Ser Ile Cys Lys Met
            35                  40                  45

Thr His Gly Lys Thr Arg Trp Thr Gln Pro Gln Leu Ile Cys Thr Gly
    50                  55                  60
```

<210> SEQ ID NO 30
<211> LENGTH: 58
<212> TYPE: PRT
<213> ORGANISM: Mus musculus

<400> SEQUENCE: 30

```
Glu Leu Cys Leu Tyr Asp Pro Pro Glu Val Pro Asn Ala Thr Phe Lys
1               5                   10                  15

Ala Leu Ser Tyr Lys Asn Gly Thr Ile Leu Asn Cys Glu Cys Lys Arg
                20                  25                  30

Gly Phe Arg Arg Leu Lys Glu Leu Val Tyr Met Arg Cys Leu Gly Asn
            35                  40                  45

Ser Trp Ser Ser Asn Cys Gln Cys Thr Ser
    50                  55
```

<210> SEQ ID NO 31
<211> LENGTH: 64
<212> TYPE: PRT
<213> ORGANISM: Mus musculus

<400> SEQUENCE: 31

```
Gly His Cys Arg Glu Pro Pro Trp Lys His Glu Asp Ser Lys Arg
1               5                   10                  15

Ile Tyr His Phe Val Glu Gly Gln Ser Val His Tyr Glu Cys Ile Pro
                20                  25                  30

Gly Tyr Lys Ala Leu Gln Arg Gly Pro Ala Ile Ser Ile Cys Lys Met
            35                  40                  45

Lys Cys Gly Lys Thr Gly Trp Thr Gln Pro Gln Leu Thr Cys Val Asp
    50                  55                  60
```

<210> SEQ ID NO 32
<211> LENGTH: 19
<212> TYPE: PRT
<213> ORGANISM: Pan troglodytes

<400> SEQUENCE: 32

```
Val Ala Val Ala Gly Cys Val Phe Leu Leu Ile Ser Val Leu Leu Leu
1               5                   10                  15

Ser Gly Leu
```

<210> SEQ ID NO 33
<211> LENGTH: 19

```
<212> TYPE: PRT
<213> ORGANISM: Macaca mulatta

<400> SEQUENCE: 33

Val Ala Val Ala Gly Cys Val Phe Leu Leu Ile Ser Val Leu Leu Leu
1               5                   10                  15

Ser Gly Leu

<210> SEQ ID NO 34
<211> LENGTH: 21
<212> TYPE: PRT
<213> ORGANISM: Mus musculus

<400> SEQUENCE: 34

Val Ala Val Ala Ser Cys Leu Phe Leu Leu Ile Ser Ile Leu Leu Leu
1               5                   10                  15

Ser Gly Leu Thr Trp
            20

<210> SEQ ID NO 35
<211> LENGTH: 6
<212> TYPE: PRT
<213> ORGANISM: Pan troglodytes

<400> SEQUENCE: 35

Thr Trp Gln Arg Arg Gln
1               5

<210> SEQ ID NO 36
<211> LENGTH: 13
<212> TYPE: PRT
<213> ORGANISM: Macaca mulatta

<400> SEQUENCE: 36

Thr Trp Gln Arg Arg Gln Arg Lys Asn Arg Arg Thr Ile
1               5                   10

<210> SEQ ID NO 37
<211> LENGTH: 11
<212> TYPE: PRT
<213> ORGANISM: Mus musculus

<400> SEQUENCE: 37

Gln His Arg Trp Arg Lys Ser Arg Arg Thr Ile
1               5                   10

<210> SEQ ID NO 38
<211> LENGTH: 15
<212> TYPE: PRT
<213> ORGANISM: Artificial Sequence
<220> FEATURE:
<223> OTHER INFORMATION: synthetic linker sequence

<400> SEQUENCE: 38

Ser Gly Gly Gly Gly Ser Gly Gly Gly Ser Gly Gly Gly Gly
1               5                   10                  15

<210> SEQ ID NO 39
<211> LENGTH: 19
<212> TYPE: PRT
<213> ORGANISM: Artificial Sequence
<220> FEATURE:
<223> OTHER INFORMATION: synthetic linker sequence

<400> SEQUENCE: 39
```

-continued

Ala Ser Thr Lys Gly Pro Ser Val Phe Pro Leu Ala Pro Ser Ser Ser
1               5                   10                  15

Gly Ser Gly

<210> SEQ ID NO 40
<211> LENGTH: 15
<212> TYPE: PRT
<213> ORGANISM: Artificial Sequence
<220> FEATURE:
<223> OTHER INFORMATION: synthetic linker sequence

<400> SEQUENCE: 40

Gly Gly Gly Gly Ser Gly Gly Gly Gly Ser Gly Gly Gly Gly Ser
1               5                   10                  15

<210> SEQ ID NO 41
<211> LENGTH: 18
<212> TYPE: PRT
<213> ORGANISM: Artificial Sequence
<220> FEATURE:
<223> OTHER INFORMATION: synthetic whitlow linker sequence

<400> SEQUENCE: 41

Gly Ser Thr Ser Gly Ser Gly Lys Pro Gly Ser Gly Glu Gly Ser Thr
1               5                   10                  15

Lys Gly

<210> SEQ ID NO 42
<211> LENGTH: 54
<212> TYPE: DNA
<213> ORGANISM: Artificial Sequence
<220> FEATURE:
<223> OTHER INFORMATION: synthetic whitlow linker sequence

<400> SEQUENCE: 42
ggcagcacca gcggcagcgg caaaccgggc agcggcgaag cagcaccaa aggc         54

<210> SEQ ID NO 43
<211> LENGTH: 25
<212> TYPE: PRT
<213> ORGANISM: Artificial Sequence
<220> FEATURE:
<223> OTHER INFORMATION: synthetic linker sequence

<400> SEQUENCE: 43

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 44
<211> LENGTH: 75
<212> TYPE: DNA
<213> ORGANISM: Artificial Sequence
<220> FEATURE:
<223> OTHER INFORMATION: synthetic linker sequence

<400> SEQUENCE: 44
ggcggtggtg gttctggagg cggtggcagc ggtggaggtg gctcaggagg aggaggtagc    60
ggcggcggag ggagt                                                    75

<210> SEQ ID NO 45
<211> LENGTH: 233

<212> TYPE: PRT
<213> ORGANISM: Homo sapiens

<400> SEQUENCE: 45

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Trp Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Lys Asp
225                 230

<210> SEQ ID NO 46
<211> LENGTH: 46
<212> TYPE: PRT
<213> ORGANISM: Homo sapiens

<400> SEQUENCE: 46

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 47
<211> LENGTH: 20
<212> TYPE: PRT
<213> ORGANISM: Homo sapiens

<400> SEQUENCE: 47

Ala Glu Pro Lys Ser Pro Asp Lys Thr His Thr Cys Pro Pro Cys Pro
1               5                   10                  15

Lys Asp Pro Lys

<210> SEQ ID NO 48
<211> LENGTH: 220
<212> TYPE: PRT
<213> ORGANISM: Homo sapiens

<400> SEQUENCE: 48

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 49
<211> LENGTH: 164
<212> TYPE: PRT
<213> ORGANISM: Homo sapiens

<400> SEQUENCE: 49

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn

```
               100                 105                 110

Glu Leu Gln Lys Asp Lys Met Ala Glu Ala Tyr Ser Glu Ile Gly Met
        115                 120                 125

Lys Gly Glu Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 50
<211> LENGTH: 23
<212> TYPE: PRT
<213> ORGANISM: Homo sapiens

<400> SEQUENCE: 50

Leu Gly Leu Leu Val Ala Gly Val Leu Val Leu Val Ser Leu Gly
1               5                   10                  15

Val Ala Ile His Leu Cys Cys
            20

<210> SEQ ID NO 51
<211> LENGTH: 26
<212> TYPE: PRT
<213> ORGANISM: Homo sapiens

<400> SEQUENCE: 51

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 52
<211> LENGTH: 25
<212> TYPE: PRT
<213> ORGANISM: Homo sapiens

<400> SEQUENCE: 52

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25

<210> SEQ ID NO 53
<211> LENGTH: 23
<212> TYPE: PRT
<213> ORGANISM: Homo sapiens

<400> SEQUENCE: 53

Leu Cys Tyr Leu Leu Asp Gly Ile Leu Phe Ile Tyr Gly Val Ile Leu
1               5                   10                  15

Thr Ala Leu Phe Leu Arg Val
            20

<210> SEQ ID NO 54
<211> LENGTH: 26
<212> TYPE: PRT
<213> ORGANISM: Homo sapiens

<400> SEQUENCE: 54

Trp Val Leu Val Val Val Gly Gly Val Leu Ala Cys Tyr Ser Leu Leu
1               5                   10                  15
```

Val Thr Val Ala Phe Ile Ile Phe Trp Val
            20                  25

<210> SEQ ID NO 55
<211> LENGTH: 24
<212> TYPE: PRT
<213> ORGANISM: Homo sapiens

<400> SEQUENCE: 55

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 56
<211> LENGTH: 24
<212> TYPE: PRT
<213> ORGANISM: Homo sapiens

<400> SEQUENCE: 56

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 57
<211> LENGTH: 220
<212> TYPE: PRT
<213> ORGANISM: Homo sapiens

<400> SEQUENCE: 57

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210             215             220

<210> SEQ ID NO 58
<211> LENGTH: 255
<212> TYPE: PRT
<213> ORGANISM: Homo sapiens

<400> SEQUENCE: 58

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 59
<211> LENGTH: 164
<212> TYPE: PRT
<213> ORGANISM: Homo sapiens

<400> SEQUENCE: 59

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

-continued

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
            85                  90                  95

Gly Gly Lys Pro Gln Arg Arg Lys Asn Pro Gln Glu Gly Leu Tyr Asn
        100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 60
<211> LENGTH: 113
<212> TYPE: PRT
<213> ORGANISM: Homo sapiens

<400> SEQUENCE: 60

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
            85                  90                  95

Ala Thr Lys Asp Thr Tyr Asp Ala Leu His Met Gln Ala Leu Pro Pro
        100                 105                 110

Arg

<210> SEQ ID NO 61
<211> LENGTH: 339
<212> TYPE: DNA
<213> ORGANISM: Homo sapiens

<400> SEQUENCE: 61
ctgagagtga agttcagcag gagcgcagac gcccccgcgt accagcaggg ccagaaccag      60
ctctataacg agctcaatct aggacgaaga gaggagtacg atgttttgga caagagacgt     120
ggccgggacc ctgagatggg gggaaagccg agaaggaaga accctcagga aggcctgtac     180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaggccctg ccccctcgc                            339

<210> SEQ ID NO 62
<211> LENGTH: 233
<212> TYPE: PRT
<213> ORGANISM: Homo sapiens

<400> SEQUENCE: 62

```
Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ala Arg Thr Pro Glu Val Thr Cys Trp Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
210                 215                 220

Leu Ser Leu Ser Pro Gly Lys Lys Asp
225                 230

<210> SEQ ID NO 63
<211> LENGTH: 46
<212> TYPE: PRT
<213> ORGANISM: Homo sapiens

<400> SEQUENCE: 63

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 64
<211> LENGTH: 20
<212> TYPE: PRT
<213> ORGANISM: Homo sapiens

<400> SEQUENCE: 64

Ala Glu Pro Lys Ser Pro Asp Lys Thr His Thr Cys Pro Pro Cys Pro
1               5                   10                  15

Lys Asp Pro Lys
            20

<210> SEQ ID NO 65
<211> LENGTH: 1316
```

```
<212> TYPE: DNA
<213> ORGANISM: Artificial Sequence
<220> FEATURE:
<223> OTHER INFORMATION: synthetic mbIL2 sequence

<400> SEQUENCE: 65
atgctcctgc tcgtgacttc acttcttctc tgtgaactcc cacacccccgc gttttttgctt      60 atccctcatc atcaccatca ccacgcacct acttcaagtt ctacaaagaa aacacagcta     120
caactggagc atttacttct ggatttacag atgattttga atggaattaa taattacaag     180
aatcccaaac tcaccaggat gctcacattt aagttttaca tgcccaagaa ggccacagaa     240
ctgaaacatc ttcagtgtct agaagaagaa ctcaaacctc tggaggaagt gctaaattta     300
gctcaaagca aaaactttca cttaagaccc agggacttaa tcagcaatat caacgtaata     360
gttctggaac taaagggatc tgaaacaaca ttcatgtgtg aatatgctga tgagacagca     420
accattgtag aatttctgaa cagatggatt acctttttgtc aaagcatcat ctcaacactg     480
acttctggag gaggtagtgg aggcggcggg agcggtgggg gagggtctgg gggtggggga     540
tccggaggtg ggtcactgca ggagctctgt gacgatgacc cgccagagat cccacacgcc     600
acattcaaag ccatggccta caggaagga accatgttga actgtgaatg caagagaggt     660
ttccgcagaa taaaaagcgg gtcactctat atgctctgta caggaaactc tagccactcg     720
tcctgggaca ccaatgtca atgcacaagc tctgccactc ggaacacaac gaaacaagtg     780
acacctcaac ctgaagaaca gaaagaaagg aaaaccacag aaatgcaaag tccaatgcag     840
ccagtggacc aagcgagcct tccaggtcac tgcagggaac ctccaccatg ggaaaatgaa     900
gccacagaga gaatttatca tttcgtggtg gggcagatgg tttattatca gtgcgtccag     960
ggatacaggg ctctacacag aggtcctgct gagagcgtct gcaaaatgac ccacgggaag    1020
acaaggtgga cccagcccca gctcatatgc acaggtaaaa tggagaccag tcagtttcca    1080
ggtgaagaga agcctcaggc aagcccccgaa ggccgtcctg agagtgagac ttcctgcctc    1140
gtcacaacaa cagatttttca aatacagaca gaaatggctg caaccatgga gacgtccata    1200
tttacaacag agtaccaggt agcagtggcc ggctgtgttt tcctgctgat cagcgtcctc    1260
ctcctgagtg ggctcacctg gcagcggaga cagaggaaga gtagaagaac aatctg       1316

<210> SEQ ID NO 66
<211> LENGTH: 41
<212> TYPE: PRT
<213> ORGANISM: Artificial Sequence
<220> FEATURE:
<223> OTHER INFORMATION: synthetic T2A and purin cleavage site sequence

<400> SEQUENCE: 66

Arg Lys Arg Arg Gly Lys Pro Ile Pro Asn Pro Leu Leu Gly Leu Asp
1               5                   10                  15

Ser Thr Ser Gly Ser Gly Glu Gly Arg Gly Ser Leu Leu Thr Cys Gly
            20                  25                  30

Asp Val Glu Glu Asn Pro Gly Pro Gly
        35                  40

<210> SEQ ID NO 67
<211> LENGTH: 123
<212> TYPE: DNA
<213> ORGANISM: Artificial Sequence
<220> FEATURE:
<223> OTHER INFORMATION: synthetic T2A and purin cleavage site sequence

<400> SEQUENCE: 67
```

```
cggaagagaa gaggcaagcc catccccaac ccactgctgg gcctggatag cacctccggc    60
tcaggagagg gcagaggctc tctgctgacc tgcggcgacg tggaagagaa cccgggcccg   120
ggc                                                                 123
```

```
<210> SEQ ID NO 68
<211> LENGTH: 499
<212> TYPE: PRT
<213> ORGANISM: Artificial Sequence
<220> FEATURE:
<223> OTHER INFORMATION: Synthetic FMC63-41BB-CD3z CAR sequence

<400> SEQUENCE: 68

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Asp Ile Gln Met Thr Gln Thr Thr Ser Ser Leu Ser Ala Ser Leu Gly
        35                  40                  45

Asp Arg Val Thr Ile Ser Cys Arg Ala Ser Gln Asp Ile Ser Lys Tyr
    50                  55                  60

Leu Asn Trp Tyr Gln Gln Lys Pro Asp Gly Thr Val Lys Leu Leu Ile
65                  70                  75                  80

Tyr His Thr Ser Arg Leu His Ser Gly Val Pro Ser Arg Phe Ser Gly
                85                  90                  95

Ser Gly Ser Gly Thr Asp Tyr Ser Leu Thr Ile Ser Asn Leu Glu Gln
            100                 105                 110

Glu Asp Ile Ala Thr Tyr Phe Cys Gln Gln Gly Asn Thr Leu Pro Tyr
        115                 120                 125

Thr Phe Gly Gly Gly Thr Lys Leu Glu Ile Thr Gly Gly Gly Gly Ser
    130                 135                 140

Gly Gly Gly Gly Ser Gly Gly Gly Ser Glu Val Lys Leu Gln Glu
145                 150                 155                 160

Ser Gly Pro Gly Leu Val Ala Pro Ser Gln Ser Leu Ser Val Thr Cys
                165                 170                 175

Thr Val Ser Gly Val Ser Leu Pro Asp Tyr Gly Val Ser Trp Ile Arg
            180                 185                 190

Gln Pro Pro Arg Lys Gly Leu Glu Trp Leu Gly Val Ile Trp Gly Ser
        195                 200                 205

Glu Thr Thr Tyr Tyr Asn Ser Ala Leu Lys Ser Arg Leu Thr Ile Ile
    210                 215                 220

Lys Asp Asn Ser Lys Ser Gln Val Phe Leu Lys Met Asn Ser Leu Gln
225                 230                 235                 240

Thr Asp Asp Thr Ala Ile Tyr Tyr Cys Ala Lys His Tyr Tyr Tyr Gly
                245                 250                 255

Gly Ser Tyr Ala Met Asp Tyr Trp Gly Gln Gly Thr Ser Val Thr Val
            260                 265                 270

Ser Ser Gly Ser Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335
```

Leu Ser Leu Val Ile Thr Leu Tyr Cys Lys Arg Gly Arg Lys Lys Leu
            340                 345                 350

Leu Tyr Ile Phe Lys Gln Pro Phe Met Arg Pro Val Gln Thr Thr Gln
            355                 360                 365

Glu Glu Asp Gly Cys Ser Cys Arg Phe Pro Glu Glu Glu Gly Gly
370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
            435                 440                 445

Leu Gln Lys Asp Lys Met Ala Glu Ala Tyr Ser Glu Ile Gly Met Lys
            450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 69
<211> LENGTH: 1497
<212> TYPE: DNA
<213> ORGANISM: Artificial Sequence
<220> FEATURE:
<223> OTHER INFORMATION: synthetic FMC63-41BB-CD3z CAR sequence

<400> SEQUENCE: 69

```
atgcttctcc tggtgacaag ccttctgctc tgtgagttac cacacccagc attcctcctg      60
attcctgaac agaagctgat aagtgaggag gacttggaca tccagatgac ccagaccacc     120
agcagcctga gcgccagcct gggcgataga gtgaccatca gctgcagagc cagccaggac     180
atcagcaagt acctgaactg gtatcagcag aaacccgacg gcaccgtgaa gctgctgatc     240
taccacacca gcagactgca cagcggcgtg cccagcagat ttctggcag cggctccggc      300 accgactaca gcctgaccat ctccaacctg aacaggaag atatcgctac ctacttctgt     360
cagcaaggca cacccctgcc ctacaccttc ggcggaggca ccaagctgga aatcacaggc     420
ggcggaggat ctggcggagg cggaagtggc ggaggggat ctgaagtgaa actgcaggaa     480
agcggccctg gcctggtggc ccatctcag tctctgagcg tgacctgtac cgtgtccggc      540
gtgtccctgc ctgactatgg cgtgtcctgg atcagacagc cccccagaaa gggcctggaa     600
tggctgggag tgatctgggg cagcgagaca acctactaca acagcgccct gaagtcccgg     660
ctgaccatca tcaaggacaa ctccaagagc caggtgttcc tgaagatgaa cagcctgcag     720
accgacgaca ccgccatcta ctactgcgcc aagcactact actacggcgg cagctacgcc     780
atggactact ggggccaggg cacaagcgtg accgtgtcta gcggatccac cacgacgcca     840
gcgccgcgac caccaacacc ggcgcccacc atcgcgtcgc agcccctgtc cctgcgccca     900
gaggcgtgcc ggccagcggc ggggggcgca gtgcacacga gggggctgga cttcgcctgt     960
gatatctaca tctgggcgcc cttggccggg acttgtgggg tccttctcct gtcactggtt    1020
atcacccttt actgcaaacg gggcagaaag aaactcctgt atatattcaa acaaccattt    1080
```

```
atgagaccag tacaaactac tcaagaggaa gatggctgta gctgccgatt ccagaagaa    1140 gaagaaggag gatgtgaact gagagtgaag ttcagcagga gcgcagacgc ccccgcgtac    1200
cagcagggcc agaaccagct ctataacgag ctcaatctag gacgaagaga ggagtacgat    1260
gttttggaca agagacgtgg ccgggaccct gagatggggg gaaagccgag aaggaagaac    1320
cctcaggaag gcctgtacaa tgaactgcag aaagataaga tggcggaggc ctacagtgag    1380
attgggatga aggcgagcg ccggagggc aagggcacg atggccttta ccagggtctc    1440
agtacagcca ccaaggacac ctacgacgcc cttcacatgc aggccctgcc ccctcgc    1497
```

```
<210> SEQ ID NO 70
<211> LENGTH: 22
<212> TYPE: PRT
<213> ORGANISM: Artificial Sequence
<220> FEATURE:
<223> OTHER INFORMATION: Synthetic signal peptide sequence

<400> SEQUENCE: 70

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 71
<211> LENGTH: 66
<212> TYPE: DNA
<213> ORGANISM: Artificial Sequence
<220> FEATURE:
<223> OTHER INFORMATION: Synthetic signal peptide sequence

<400> SEQUENCE: 71
atgcttctcc tggtgacaag ccttctgctc tgtgagttac cacacccagc attcctcctg    60
attcct                                                               66

<210> SEQ ID NO 72
<211> LENGTH: 10
<212> TYPE: PRT
<213> ORGANISM: Artificial Sequence
<220> FEATURE:
<223> OTHER INFORMATION: synthetic Myc tag sequence

<400> SEQUENCE: 72

Glu Gln Lys Leu Ile Ser Glu Glu Asp Leu
1               5                   10

<210> SEQ ID NO 73
<211> LENGTH: 30
<212> TYPE: DNA
<213> ORGANISM: Artificial Sequence
<220> FEATURE:
<223> OTHER INFORMATION: synthetic Myc tag sequence

<400> SEQUENCE: 73
gaacagaagc tgataagtga ggaggacttg                                     30

<210> SEQ ID NO 74
<211> LENGTH: 242
<212> TYPE: PRT
<213> ORGANISM: Artificial Sequence
<220> FEATURE:
<223> OTHER INFORMATION: synthetic FMC63 scFv sequence

<400> SEQUENCE: 74
```

-continued

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
            165                 170                 175

Glu Thr Thr Tyr Tyr Asn Ser Ala Leu Lys Ser Arg Leu Thr Ile Ile
                180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 75
<211> LENGTH: 726
<212> TYPE: DNA
<213> ORGANISM: Artificial Sequence
<220> FEATURE:
<223> OTHER INFORMATION: synthetic FMC63 scFv sequence

<400> SEQUENCE: 75

```
gacatccaga tgacccagac caccagcagc ctgagcgcca gcctgggcga tagagtgacc    60
atcagctgca gagccagcca ggacatcagc aagtacctga actggtatca gcagaaaccc   120
gacggcaccg tgaagctgct gatctaccac accagcagac tgcacagcgg cgtgcccagc   180
agatttctg gcagcggctc cggcaccgac tacagcctga ccatctccaa cctggaacag   240
gaagatatcg ctacctactt ctgtcagcaa ggcaacaccc tgccctacac cttcggcgga   300
ggcaccaagc tggaaatcac aggcggcgga ggatctggcg gaggcggaag tggcggaggg   360
ggatctgaag tgaaactgca ggaaagcggc cctggcctgg tggcccccatc tcagtctctg   420
agcgtgacct gtaccgtgtc cggcgtgtcc ctgcctgact atggcgtgtc ctggatcaga   480
cagccccca gaaagggcct ggaatggctg ggagtgatct ggggcagcga gacaacctac   540
tacaacagcg ccctgaagtc ccggctgacc atcatcaagg acaactccaa gagccaggtg   600
ttcctgaaga tgaacagcct gcagaccgac gacaccgcca tctactactg cgccaagcac   660
```

```
tactactacg gcggcagcta cgccatggac tactggggcc agggcacaag cgtgaccgtg    720
tctagc                                                                726
```

<210> SEQ ID NO 76
<211> LENGTH: 71
<212> TYPE: PRT
<213> ORGANISM: Artificial Sequence
<220> FEATURE:
<223> OTHER INFORMATION: synthetic hinge and transmembrane domain
      sequence

<400> SEQUENCE: 76

```
Gly Ser Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
    50                  55                  60

Leu Val Ile Thr Leu Tyr Cys
65                  70
```

<210> SEQ ID NO 77
<211> LENGTH: 213
<212> TYPE: DNA
<213> ORGANISM: Artificial Sequence
<220> FEATURE:
<223> OTHER INFORMATION: synthetic hinge and transmembrane domain
      sequence

<400> SEQUENCE: 77

```
ggatccacca cgacgccagc gccgcgacca ccaacaccgg cgcccaccat cgcgtcgcag    60
cccctgtccc tgcgcccaga ggcgtgccgg ccagcggcgg ggggcgcagt gcacacgagg   120
gggctggact cgcctgtga tatctacatc tgggcgccct ggccgggac ttgtggggtc    180 cttctcctgt cactggttat cacccttac tgc                                 213
```

<210> SEQ ID NO 78
<211> LENGTH: 41
<212> TYPE: PRT
<213> ORGANISM: Artificial Sequence
<220> FEATURE:
<223> OTHER INFORMATION: synthetic costimulatory domain sequence

<400> SEQUENCE: 78

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu
            35                  40
```

<210> SEQ ID NO 79
<211> LENGTH: 123
<212> TYPE: DNA
<213> ORGANISM: Artificial Sequence
<220> FEATURE:
<223> OTHER INFORMATION: synthetic costimulatory domain sequence

<400> SEQUENCE: 79

```
aaacgggca gaaagaaact cctgtatata ttcaaacaac catttatgag accagtacaa    60
```

-continued

```
actactcaag aggaagatgg ctgtagctgc cgatttccag aagaagaaga aggaggatgt    120
gaa                                                                 123

<210> SEQ ID NO 80
<211> LENGTH: 113
<212> TYPE: PRT
<213> ORGANISM: Artificial Sequence
<220> FEATURE:
<223> OTHER INFORMATION: synthetic CAR CD3z domain sequence

<400> SEQUENCE: 80

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 81
<211> LENGTH: 339
<212> TYPE: DNA
<213> ORGANISM: Artificial Sequence
<220> FEATURE:
<223> OTHER INFORMATION: synthetic CAR CD3z domain sequence

<400> SEQUENCE: 81
ctgagagtga agttcagcag gagcgcagac gcccccgcgt accagcaggg ccagaaccag    60
ctctataacg agctcaatct aggacgaaga gaggagtacg atgttttgga caagagacgt   120
ggccgggacc ctgagatggg gggaaagccg agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg ccccctcgc                         339
```